United States Patent [19]

Bell et al.

[11] Patent Number: 4,937,232
[45] Date of Patent: Jun. 26, 1990

[54] INHIBITION OF PROTEIN KINASE C BY LONG-CHAIN BASES

[75] Inventors: Robert M. Bell; Carson Loomis; Yusuf Hannun, all of Durham, N.C.

[73] Assignee: Duke University, Durham, N.C.

[21] Appl. No.: 195,664

[22] Filed: May 17, 1988

Related U.S. Application Data

[63] Continuation of Ser. No. 906,951, Sep. 15, 1986, Pat. No. 4,816,450.

[51] Int. Cl.$^5$ .............................................. A61K 31/70
[52] U.S. Cl. ........................................ 514/26; 514/28; 536/5
[58] Field of Search ......................... 536/5; 514/26, 28

[56] References Cited

U.S. PATENT DOCUMENTS

| | | | |
|---|---|---|---|
| 4,476,119 | 10/1984 | Della Valle et al. | 514/25 |
| 4,544,552 | 10/1985 | Fraefel et al. | 536/53 |
| 4,582,821 | 4/1986 | Kettner et al. | 514/18 |
| 4,614,796 | 9/1986 | Kawamata et al. | 536/5 |
| 4,639,437 | 1/1987 | Della Valle et al. | 514/54 |
| 4,673,667 | 6/1987 | Catsimpoolas | 514/25 |
| 4,707,469 | 11/1987 | Della Valle et al. | 514/26 |
| 4,710,490 | 12/1987 | Catsimpoolas et al. | 514/25 |

*Primary Examiner*—Ronald W. Griffin
*Attorney, Agent, or Firm*—Oblon, Spivak, McClelland, Maier & Neustadt

[57] ABSTRACT

Compositions for inhibiting protein kinase C, comprising an inhibitory amount of a compound having the formula:

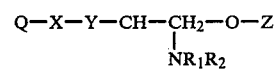

wherein Q is a hydrophobic group;
wherein X is —CH$_2$—CH$_2$— or —CH=CH—, which may be substituted by one or more halogens or C$_1$-C$_3$ alkyl groups,
wherein Y is

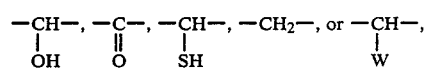

wherein W is a halogen;
wherein R$_1$ and R$_2$ may be the same or different and are selected from hydrogen, lower alkyl groups having from 1 to 7 carbon atoms, aralkyl, and aryl groups, and
wherein Z is a phosphate or an organic group, and a pharmaceutically acceptable carrier material; and a method for inhibiting protein kinase C using such compositions.

11 Claims, 35 Drawing Sheets

Sphingosine  X = H
Psychosine  X = Galactose
(Galactosylsphingosine)
Lysosulfatide  X = Sulfogalactose
(Sulfogalactosylsphingosine)
Lyso GM₂  X = Gal-NAc—Gal-Glc
                    \Sia

INHIBITION OF PROTEIN KINASE C BY LONG-CHAIN BASES

This invention was made with Government support under AM 20205 awarded by the Department of Health and Human Services. The Government has certain rights to this invention.

This is a continuation of application Ser. No. 06/906,951, filed Sept. 15, 1986, now U.S. Pat. No. 4,816,450, issued Mar. 28, 1989.

BACKGROUND OF THE INVENTION

1. Field of the Invention

The present invention relates to a method for inhibiting the enzyme protein kinase C by amphipathic long-chain bases such as sphingosine and sphinganine The invention further relates to compositions capable of producing inhibition of protein kinase C. Inhibition of protein kinase C is useful in a variety of ways. Such inhibition can lead to inhibition of the oxidative burst in neutrophils, whereby an anti-inflammatory effect is achieved. Inhibition of protein kinase C can also lead to inhibition of differentiation and growth of cells and can thereby produce an anti-tumor effect.

2. Description of the Related Art

Phospholipid/$Ca^{+2}$-dependent protein kinase (protein kinase C) is a major protein phosphorylation system which was first found in brain (Takai et al, *J. Biol. Chem.* 252, 3692, 1977) and subsequently shown to occur widely in tissues and phyla of the animal kingdom (Kuo et al, *Proc. Natl Acad. Sci. U.S.A.* 77, 7039, 1980). Protein kinase C plays an important role in signal transduction, cellular differentiation, tumor promotion and neurotransmission. The central function of protein kinase C in transducing intracellularly extracellular signals has recently been recognized (Nishizuka, *Nature* 308, 693, 1984). Extracellular agents including neurotransmitters, hormones, and growth factors are bound by specific cell surface receptors and elicit, by transmembrane signalling, the generation of two second messengers by stimulating the degradation of phosphatidylinositols (Nishizuka, *Philos. Trans. R. Soc. Lond. B. Biol. Sci.* 302, 101, 1983; Michel, *Trends Biochem. Sci.* 4, 128, 1979; and Berridge, *Biochem. J.* 220, 345, 1984). In particular, the inositol phospholipid phosphatidylinositol-4-5-bisphosphate ($PIP_2$) is hydrolyzed to inositol triphosphate ($IP_3$) and sn-1,2-diacylglycerol (DAG) (Nishizuka, *Science,* 225, 1365, 1984). DAG activates protein kinase C. Phorbol-diesters, which are potent tumor promoters, also activate protein kinase C (Castagna et al, *J. Biol. Chem.* 257, 7847, 1982). In fact, it appears that protein kinase C is the phorbol-diester receptor (Niedel et al, *Proc. Natl. Acad. Sci. U.S.A.* 80, 36, 1983) and mediates most, if not all, of the biological effects of the phorbol-diesters.

Recently, protein kinase C has been shown to be inhibited by a lipoidal amine, 4-aminomethyl-1-[2,3-(di-n-decyloxy)n-propyl]-4-ohenylpiperidine dihydrochloride (CP-46, 665-1) in human leukemic cells (Shoji et al, *Biochem. Biophys. Research Comm.,* 590, 1985). This amine has also been shown to have anti-metastatic properties in rodent tumor models (Wolff et al, *Cancer Immunol. Immunother.,* 12, 97, 1982). This study supports the connection between inhibition of protein kinase C and anti-cancer activity, such as in human chronic myelogenous leukemia and other similar types of cancer, and is hereby incorporated by reference in this application.

Dyson and Montano have reported an anti-tumor agent which is a sphingosine derivative (*J. Am. Chem. Soc.,* 100, 7441, 1978), but protein kinase C was not implicated.

Several other types of inhibitors of protein kinase C have also been reported. These include calmodulin antagonists (Mori et al, *J. Biol. Chem.* 255 8378, 1980; Wise et al, *J. Biol. Chem.* 257, 8489, 1982; and Robinson, *J. Cell. Biol.* 101 1052, 1985), H-7 (Hidaka, *Biochemistry* 23, 5036, 1984), adriamycin (Wise, *J. Biol. Chem.* 257, 8489, 1982); alkyllysosphospholipid (Helfman, *Cancer Res.* 43, 2955, 1983), a non-steroidal anti-estrogen, tamoxifen (O'Brien, *Cancer Res.* 45, 2462, 1985), amiloride (Besterman, *J. Biol. Chem.* 260, 1155, 1985), verapamil (Mori et al, *J. Biol. Chem.* 255, 8378, 1980), bilirubin (Sano, *Ped. Res.* 19, 587, 1985), oalmitoylcarnitine (Nakadate, *Cancer Res.* 46, 1589, 1986), gangliosides $G_{M1}$, $G_{D1a}$, $G_{D1b}$ and $G_{T1b}$ (Kim, *J. Neurosci Res.* 15, 159, 1986), and retinal (Patarroyo, *Immunobiology* (Stuttgart) 170, 305, 1985). These various inhibitors of protein kinase C have widely varying potencies, and some are specific whereas others are non-specific.

In order to fully appreciate the present invention relating to inhibition of protein kinase C, it is necessary to understand other related work relating to the activation of protein kinase C. Such activation has been associated with tumor growth, and it is also believed that oncogenes may somehow affect the degree of activation of protein kinase C.

ACTIVATION OF PROTEIN KINASE C

The mechanism of protein kinase C activation by DAG, $Ca^{+2}$, and phospholipid is of interest because activation of this enzyme is fundamental to tumor promotion, cellular transformation and to understanding the inhibition by anti-tumor agents. Protein kinase C purified from rat brain cytosol consists of a single 80 kDa polypeptide which can be cleaved with trypsin into a 51 kDa catalytic fragment which is fully active in the absence of phospholipid, $Ca^{2+}$ and DAG, and a 32 kDa fragment which is fully capable of high affinity [$^3$H]phorbol-dibutyrate binding. Phosphatidylserine (PS) is the most effective phospholipid in activating protein kinase C when sonicated with DAG. DAG (phorbol-diesters) greatly reduced the concentration of $Ca^{2+}$ required for activation. Translation of the enzyme from the cytosol to the membranes upon activation may be an important event of signal transduction. Alternatively, the enzyme may always be on the membrane "primed" to transduce DAG signals.

The present inventors developed mixed micellar methods to investigate the specificity, stoichiometry and mechanism of protein kinase C regulation by PS, DAG and $Ca^{2+}$ (see Experimental section herein). When the liquid cofactors are dispersed into detergent micelles of Triton-X-100 or β-octylglucoside at low mole fractions, the number of molecules present per micelle can be systematically varied. Such analysis led to the conclusion that a single molecule of DAG is sufficient for protein kinase C activation and that 4 molecules of PS are required. Monomeric protein kinase C is the active species. Studies by the inventors employed over 20 DAG analogues to establish a precise DAG binding site (Ganong et al, *Proc. Natl. Acad. Sci. U.S.A.,* 83, 1184, 1986) The 3-hydroxyl group and both oxygen esters of sn-1,2-DAG are essential. The structure-function and stoichiometry studies are in full accord with DAG second messenger functions. A model in which the 4-carboxyl groups of PS bind $Ca^{2+}$, and create a surface with which protein kinase C binds but is inactive (see FIG. 1) was developed. DAG activation occurs by three bonds to the protein kinase C-4PS-$Ca^{2+}$ complex. A direct bond from DAG/phorboldiester to $Ca^{2+}$ was suggested to account for the increased affinity of $Ca^{2+}$ in the complex. The mixed micellar methods and mechanistic model have also been useful in analyzing protein kinase C inhibitors.

DAG Second Messengers

Direct evidence for the surprising function of DAG as intracellular second messengers in a variety of cells exists from studies employing cell permeable DAGs. The limited solubility of DAG containing long chain fatty acids, like those produced in response to extracellular signals, makes their addition to cells difficult. However, shorter chain length molecules have sufficient solubility to enter cells and activate protein kinase C. 1-Oleoyl-2-acetylglycerol (OAG) was the first DAG of this type described. Dioctanoylglycerol ($diC_8$) proved most effective among a series of DAGs containing fatty acids 3-10 carbons in length in ctivating protein kinase C when added to cells. $DiC_8$ completely displaced [$^3$H]phorbol-dibutyrate from its receptor, protein kinase C, in HL60 cells whereas OAG would not. These cell permeable DAG's mimicked biological responses of phorbol-diesters whereas $diC_8$ analogues modified at the 3-hydroxyl position would not activate protein kinase C, displace [$^3$H]phorbol-dibutyrate or elicit biological responses. Cell permeable DAG's are valuable tools to investigate DAG second messenger functions and the function of protein kinase C.

Oncogenes and Protein Kinase C Activation

The field of oncogene research has progressed to the point where more than 40 distinct oncogenes of viral and cellular origin have been identified and their structures determined. The vast majority of oncogenes encode for altered forms of normal cellular proteins; thus, many of the protooncogene products are thought to participate normally in regulation of growth and differentiation. Clues on the function of the oncogenes whose products exist in the cytoplasm have emerged from their structures. Several of the gene products appear related to growth factors or other elements involved in transmembrane signalling. These oncogene products may function by altering the level of critical second messenger molecules, such as diacylglycerol (DAG). The oncogene products of nuclear location may modulate transcriptional activity. The oncogenes can be grouped into a small number of functional classes suggesting that only a small number of mechanisms of action underlie the functions of the encoded proteins.

Transmembrane signalling, the molecular basis by which growth factors, neurotransmitters, and hormones regulate a variety of cellular functions including proliferation and differentiation merged with the metabolism of membrane phospholipids when protein kinase C was discovered. As pointed out above, diacylglycerol was shown to be the molecular link between receptor occupancy, phosphatidylinositol (PI) turnover and cellular response when it was shown to activate protein kinase C. Protein kinase C is the intracellular receptor of phorbol-diesters and other tumor promoters; tumor promoters activate protein kinase C by interacting at the DAG site. As shown in FIG. 1, the mechanism of transmembrane signalling is now thought to involve receptor mediated turnover of $PIP_2$ (or other PI's) coupled through a GTP (G protein) dependent activation of phospholipase C. This mechanism is analogous to that established for transmembrane signalling involving c-AMP formation. In the case of transmembrane signalling linked to $PIP_2$, two second messengers are produced. $IP_3$ is believed to function as a second messenger in the mobilization of intracellular calcium. The role of $Ca^{+2}$ as a second messenger is well known.

Oncogene Products Elevate DAG Levels

Since several of the oncogene products resembled elements involved in transmembrane signalling, the idea that these elements perpetually function to activate transmembrane signalling and elevate critical second messengers arose. As shown in FIG. 1, cells containing sis become transformed by autocrine stimulation by a PDGF like molecule; the erbB gene product is a stump of the EGF receptor (neu and fms gene products are also receptors) and ras may be a G protein activating phospholipase C. The inventors developed a sensitive assay, 20 pmol to 25 nmol, for DAG second messengers. The assay employed *E. coli* DAG kinase whose structural gene was cloned and sequenced, to quantitatively convert the sn-1,2-DAG present in crude lipid extracts to [$^{32}$P]phosphatidic acid. K-ras transformed NRK cells had 2.5 times as much DAG as nontransformed cells at 34° or 38°. This increase in DAG was similar to that observed in platelets in response to thrombin and in hepatocytes in response to vasopressin. When a temperature sensitive k-ras mutant was employed, DAG levels were elevated at the permissive but not at the restrictive temperature. Sis transformed cells had elevated levels as well. Fleishman et al (*Science* 231, 407, 1986) have also reported elevated levels of DAG in ras transformed cells. Altered DAG levels may be the (a) molecular mechanism explaining how certain oncogenes function.

Description of the Invention

The novel hypothesis that sphingolioid metabolites may function as negative effectors, second messengers, of protein kinase C emerged from a serendipitous observation made during studies of the specificity of DAG activation of protein kinase C. Ceramide, a building block of sphingolipids, was tested because it resembled DAG. Ceramide did not activate or inhibit protein kinase C. Surprisingly, sphingosine, a building block of ceramide, proved to be as potent an inhibitor of protein kinase C activation as DAG was as an activator. This was intriguing because sphingosine is a normal component of cells; detailed mechanistic analysis had to await development of the mixed micellar methods of protein kinase C activation and phorbolbinding. In brief, sphingosine inhibited [$^3$H]phorbol-dibutyrate binding to protein kinase C in vitro, in human platelets and neutrophils, and in HL60 cells. Inhibition occurs without displacement of protein kinase C from the membrane/micelle surface. Moreover, sphingosine inhibited cellular responses known to be stimulated by cell permeable DAGs of phorbol-diesters. Sphingosine inhibited 40 kDa protein phosphorylation in platelets, blocked the PMA dependent differentiation of HL60 cells to macrophages and inhibited the oxidative burst of human neutrophils in response to a number of different agents.

Based on the above observations, the present inventors have discovered that a variety of amphipathic amines, such as metabolites of sphingolipids which are major components of the cell surface, function as negative effectors of protein kinase C. Naturally occurring sphingolipid metabolites thus seem to comprise a novel set of "second messengers" with vital functions in regulation of cell growth, differentiation, and development. These negative lipid effectors appear to underlie the action of negative growth factors, biological activities of the gangliosides including growth inhibition, contact inhibition, differentiation and oncogenesis, immunosuopression, the pathobiology of the sphingolipidoses, the action of tumor necrosis factor, and the cytopathic effects of HTLV-3 on T4+ lymphocytes.

These observations have created and shaped a unifying hypothesis. The global implications stemming from this observation are striking. Sphingosine/lysosphingolipids may function as second messengers to inhibit protein kinase C. Protein kinase C activity would, therefore, be a function of positive effectors (DAG and $Ca^{2+}$) and negative effectors (sphingosine/lysosphingolipids). These negative effectors could establish a "set point" for protein kinase C activation; negative effectors may explain why kinase C is not active at resting cellular DAG levels. Such second messengers could be produced in response to extracellular signals and could define, in part, the functional significance of the sphingolipids. The origin of this putative set of second messengers, membrane sphingolipids, would be analogous to the origin of DAG second messengers, membrane glycerolipids (see FIG. 2).

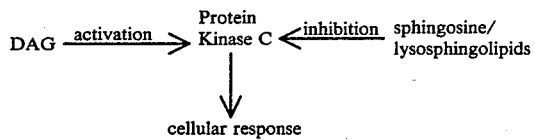

This hypothesis stems from an attempt to integrate and extend knowledge of glycosphingolioids which are present on cell surfaces and within cells. The patterns of cell surface glycosphingolipids change during cell differentiation and development and in transformed cells. Glycosphingolipids have been implicated in the cell's density sensing mechanisms (contact inhibition) through specific interactions with cell surface proteins. Importantly, glycosphingolipids can inhibit responses to growth factors by interacting with receptors present in fibroblasts, T-cells line, and epidermoid cells. Glycosphingolipids are also known to modulate the activities of membrane bound enzymes. Thus, the hypothesis provides a molecular model relevant to understanding the recurrent immunological observation that glycosphingolipids comprise prominent tumor associated antigens. It is possible to piece together a metabolic cycle as shown in FIG. 4.

The inventors believe that lysosphingolipids represent the "missing molecular link" between sphingolipids, signal transduction, differentiation, development, and cellular transformation. This hypothesis has the potential to make sense at a molecular level out of diverse areas of biochemistry, neurobiology, cell biology, immunology and tumor biology.

Specifically, sphingosine/lysosphingoglycolipid inhibition of protein kinase C appear to underlie the role of glycolipids in cellular transformation and the biological activities of glycolipids when added to cells (i.e. inhibition of mitogenesis by PDGF and EGF and immunosuppression by blocking IL-2 stimulation of T cells).

Further, negative growth factors, "chalones" including transforming growth factor-$\beta$, fibroblast growth regulator (FGR-s (13K) from 3T3 cells) and others might work through sphingosine based negative effectors.

The concept of negative effectors is attractive for reciprocal regulation is the rule in biology. These effectors could be the "signals" of contact inhibition. Glycolipids have been implicated in processes where cells become non-responsive to growth factors. Finally, it is possible that modulation of these effectors might underlie the dramatic effects of tumor necrosis factor, and the effects of the AIDS virus, HTLV-III, on T4+ helper cells. Production of sphingosine signals could be highly cytotoxic. Sphingosine is highly cytotoxic; 2-3 $\mu g/ml$ inhibits growth of CHO cells. Alteration of the level of these negative effectors by oncogene products seems to result in developmental trapping and underlie promyelocytic leukemias.

Protein kinase C inhibition might be involved in the pathobiology of the sphingolipidoses where glycolipids accumulate because of genetic defects of lysosomal enzymes of glycolipid catabolism. The inventors prepared deacylated (lyso-forms) of many of the sphingolipids. All were found to inhibit protein kinase C (see FIG. 4), whereas the parental sphingolipids did not. Conversion of the accumulated glycolipids to lysosphingolipids or sphingosine occurs in these disorders. The pathobiology which has remained a mystery is likely caused by these agents which interfere with signal transduction.

Detailed understanding of the mechanism and structure of protein kinase C is of utmost importance because this target is the site of tumor promoter action, and an essential element of signal transduction which responds to elevated levels of DAG second messengers produced by growth factors and certain oncogene products. Molecular understanding of this target is invaluable for drug design and/or discovery projects. Specifically, protein kinase C may be considered a target for anti-tumor agents. If DAG signals are elevated by specific oncogenes, ras, sis, erbB, fms, etc., then inhibition of protein kinase C should block the action of the oncogene product. The same logic extends to other enzymes of second messenger generation and signal attenuation.

Because protein kinase C has also been implicated in at least some neutrophil oxidative activation mechanisms, it has also been of interest to study the effect of protein kinase C inhibitors on these mechanisms. Compounds which inhibit protein kinase C are not automatically capable of inhibiting human neutrophil activation. For example, the protein kinase C inhibitors H-7 and H-9 (Wright, *Biochem. Biophys. Res. Commun.* 135, 749, 1986) are incapable of inhibiting the respiratory burst in human neutrophils. Inhibition of the oxidative burst can reduce inflammation in affected tissue. Neutrophil oxidative metabolism also plays an important role in tumor generation (Schwarz, *Carcinogenesis* 5, 1663, 1984), so inhibition of the oxidative burst can inhibit tumor formation.

SUMMARY OF THE INVENTION

Accordingly, it is an object of the present invention to provide new and effective compositions for the inhibition of protein kinase C.

It is also an object of the present invention to provide a method of inhibiting protein kinase C which involves contacting this enzyme either in vitro or in vivo with an inhibitory concentration of a compound or composition according to the present invention.

It is yet another object of the present invention to provide a method of treating inflammation which involves treating a mammal afflicted with inflammation with a protein kinase C inhibitory concentration of a protein kinase C inhibitor according to this invention.

It is yet another object of the present invention to provide a method for inhibiting the oxidative burst in neutrophils which involves contacting neutrophils either in vitro or in vivo with a protein kinase C inhibitory concentration of a compound capable of inhibiting this enzyme.

These and other objects as will hereinafter become more apparent have been accomplished by discovering that certain compounds, amphipathic amines such as notably sphingosine, sphinganine and related compounds, are capable of potently inhibiting protein kinase C both in vitro and in vivo, and further that these compounds are capable of preventing inflammation by inhibiting the neutrophil oxidative burst activation mechanisms. The compounds according to the present invention have the following general structure:

$$Q-X-Y-\underset{NR_1R_2}{CH}-CH_2-O-Z$$

wherein Q is a hydrophobic group;
wherein X is —CH$_2$—CH$_2$— or —CH=CH—, which may be substituted by one or more halogens or C$_1$-C$_3$ alkyl groups,
wherein Y is

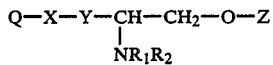

wherein W is a halogen;
wherein R$_1$ and R$_2$ may be the same or different and are selected from hydrogen and lower alkyl groups having from 1 to 7 carbon atoms, aryl groups having from 6 to 12 carbon atoms, and aralkyl groups having from 6 to 15 carbon atoms, and
wherein Z is any organic group or a phosphate, and is not necessarily further limited. More specifically, Z may be any alkyl or aralkyl group, which is cyclic, branched or straight chain, and which may be substituted by conventional pharmaceutically acceptable substituents such as halogens, nitro groups, hydroxyl groups, etc.; nucleotides or nucleosides, polynucleotides or polynucleosides, amino acids, peptides, saccharides, polysaccharides, acetyl groups, etc. When Z is an alkyl or aralkyl group, it may preferably have from 1 to 12 carbon atoms, more preferably from 1 to 10 carbon atoms, and most preferably 3 to 8 carbon atoms. Z may preferably be selected from the group consisting of H, glycyl, arginyl, lysyl, galactosyl, sulfogalactosyl, glucosyl, lactosyl, trihexosyl, phosphorylcholine, GalNAc-Gal-Glc, Gal-Gal-Glc, Sia-Gal-Glc,

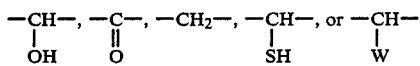

By GalNAc is meant N-acetyl galactosamine; by Glc is meant glucose, by Gal is meant galactose, and by Sia is meant sialic acid. By trihexosyl is meant polysaccharides composed of three hexoses such as galactose, glucose, mannose, glucose, etc. Both D and L isomers are contemplated.

Q may be any hydrophobic group, such as a long chain alkyl group having from 2 to 30 carbon atoms, which may be singly or multiply unsaturated, straight chain, branched, or may contain cycloalkyl groups.

The compounds of the invention can also be used in the form of pharmaceutically acceptable salts, such as acid addition salts formed from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methansulfonate, 2-naphthalanesulfonate, nicotinate, oxalate, palmitate, pectinate, persulfate, 3-phenylpropionate, picrate, pivalate, propionate, succinate, sulfate, tartrate, thiocyanate, tosylate, and undecanoate. Of these salts, simple inorganic salts, such as salts of the hydrogen halides are preferred. The compounds of the general formula which are not salts are particularly preferred.

DESCRIPTION OF THE PREFERRED EMBODIMENTS

Figure 1:
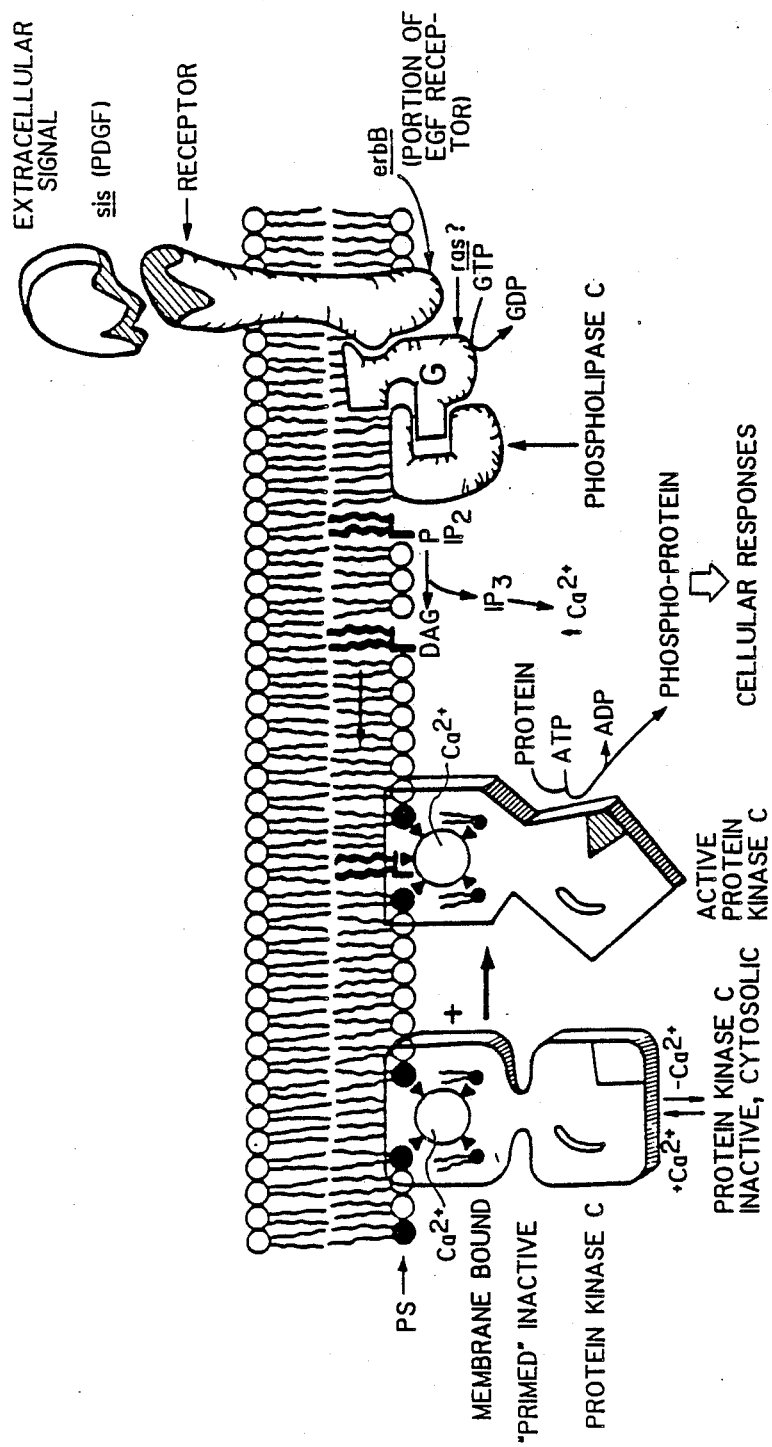
FIG. 1: Mechanism of transmembrane signalling and protein kinase C activation by DAG second messengers. The figure illustrates oncogene products which resemble elements of transmembrane signalling.
Figure 2:
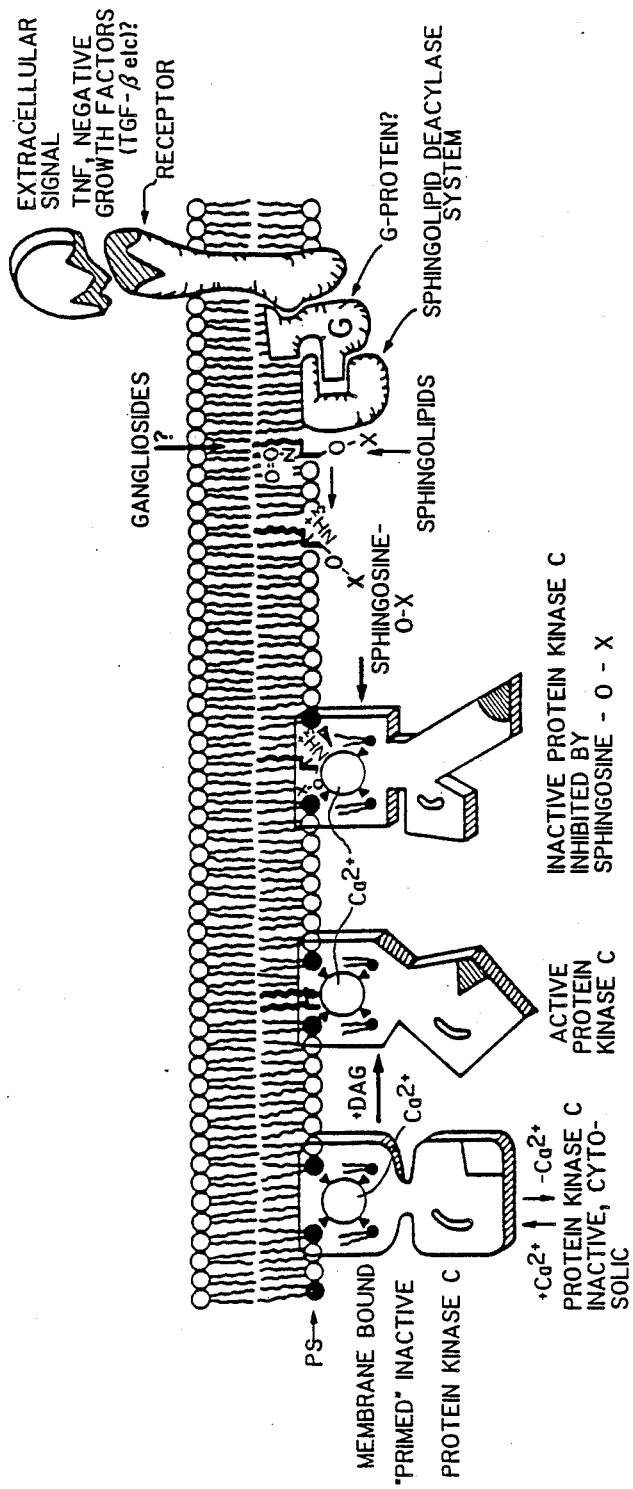
FIG. 2: Mechanism of transmembrane signalling and protein kinase C inhibition by sphingosine/lysosphingolipids putative second messengers. The figure depicts a model for the generation of sphingosine/lysosphingolipids and their inhibition of protein kinase C.

Protein kinase C according to the present invention includes the enzyme discussed by Nishizuka, Science, 233, 305, 1986, which is hereby incorporated by reference herein. Functional equivalents of this enzyme (i.e., homologous proteins which have essentially the same activity as protein kinase C) which are known or are discovered are also included under the meaning of protein kinase C. For example, isozymes of protein kinase C, three of which are known, are included in the meaning of protein kinase C.

A compound is an inhibitor of protein kinase C if it is capable of blocking cell adherence or preventing phorbol ester-dependent differentiation of human promyelocytic leukemic (HL-60) cells in vitro at concentrations up to approximately 10 mmolar. The precise method by which inhibition was determined for sphinganine, sphingosine and related compounds is described in detail in the experimental section herein. For example, using the assays described in the experimental section, inhibitors which decrease adherence by 50% at a concentration on the order of 10 millimolar or lower are preferred. More preferred are compounds exhibiting such an effect at concentrations on the order of up to about 1 mmolar. Particularly preferred are those compounds exerting such activity at concentrations up to 100 μmolar. This invention is not limited, however, by the particular methods of measuring inhibition of protein kinase C described herein. One of skill in the art may formulate other possible assay methods for determining whether a compound can inhibit protein kinase C. In general, in assays in which a $K_i$ (inhibition constant) is determined for a particular compound with protein kinase C, a $K_i$ lower than the millimolar range is desired, preferably a $K_i$ in the micromolar range or submicromolar range (e.g., the nanomolar range).

The critical structural features of sphingosine and related compounds required for inhibition of protein kinase C are the amine moiety and a hydrophobic character. Substitution at the 1-hydroxyl group does not abolish inhibition. Accordingly, lysosphingolipids containing a variety of 1-hydroxyl substituents have also been found to be inhibitors of protein kinase C. In the lysosphingolipids, the preferred head groups at the 1-hydroxyl position are phosphorylcholine, amino acids (such as glycine, arginine, lysine, alanine, serine, etc.) glucose, galactose, lactose, sulfogalactose, trihexoses, and other more complex sugar residues with sialic acid substituents that occur in the gangliosides. The 3-keto and threo- isomer of sphingosine, and sphinganine (no double bond) will inhibit protein kinase C. Further, the lyso-derivatives of all sphingolipids tested which are modified at 1-hydroxyl are active. Stearylamine is active and has been reported to be cytotoxic.

The specificity of protein kinase C inhibition by sphingosine was investigated (see the Experimental section). As a result, it was discovered that swainsonine, a molecule structurally related to sphingosine (Colegate, *Am. J. Chem.* 32, 2257, 2979) was not an inhibitor. Moreover, the following compounds were also discovered not to be inhibitors of protein kinase C: N-acetylsphingosine, ceramide, 1,3-dihydroxy-2-amino-3-phenylpropane, fatty acids, and cetyl triethylammonium bromide. On the other hand, 3-ketosphinganine, erythro- and threo- sphinganine were inhibitors.

In the general formula, Q may be any hydrophobic group. So long as Q is a hydrophobic group, it is inconsequential what group it is as long as Q does not interfere with inhibition. For example, Q may be an alkyl group containing from 2 to 30 carbon atoms, which may contain one or more (preferably 1 to 5) double bonds, and may be straight chain or branched and may contain substituent groups (e.g. halogen such as Cl, Br, F; or aryl such as phenyl).

Preferred Q's are:

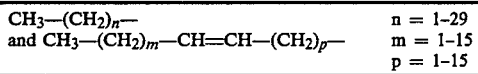

| | |
|---|---|
| $CH_3-(CH_2)_n-$ | $n = 1-29$ |
| and $CH_3-(CH_2)_m-CH=CH-(CH_2)_p-$ | $m = 1-15$ |
| | $p = 1-15$ |

In the above formulas, n is preferably 2-20, more preferably 10-16, and most preferably 11-13; m and p are each preferably 2-10.

X in the general formula is preferably $-CH_2-CH-$ or $-CH=CH-$.

Y in the general formula is preferably

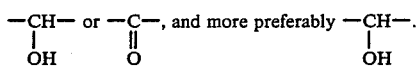

$-\underset{\underset{OH}{|}}{CH}-$ or $-\underset{\underset{O}{\|}}{C}-$, and more preferably $-\underset{\underset{OH}{|}}{CH}-$.

$R_1$ and $R_2$ are both preferably hydrogen atoms, but may also be $C_1-C_7$ alkyl groups, such as methyl, ethyl, propyl, butyl, etc., or may be aryl, such as phenyl, p-methoxy-phenyl, p-chloro-phenyl; or aralkyl, such as benzyl, phenethyl, etc. Aryl and aralkyl preferably have 5 to 10 carbon atoms.

The compounds falling within the scope of this invention may be naturally occurring or synthetically produced. Preferred naturally occurring compounds are sphingosine, sphinganine and lysosphingolipids.

The structural requirements for inhibition of the oxidative burst of neutrophils includes a hydrophobic group such as a long aliphatic chain and an amino-containing head group. There is modest specificity for native (erythro) isomer of sphinganine.

The sphingolipids such as sphingosine and sphinganine are well known compounds and are available commercially or are readily synthesized by known methods (see Experimental section).

The ways in which the above compounds have been tested to show their ability to inhibit protein kinase C, and other features relative to the mode of inhibition of these compounds are described in the Experimental Examples.

The compounds of the present invention and their pharmaceutically active salts, may be formulated into pharmaceutical compositions which may be used to treat mammals such as man, which are afflicted with various conditions in which the activity of protein kinase C is accelerated, or conditions which are treatable by inhibiting protein kinase C. For example, the present compounds can be used to treat asthma, inflammation, psoriasis or tumor metastases.

The compositions of the present invention may be administered in any mode such as orally, parenterally, intradermally, intramuscularly, intravenuously, subcutaneously or topically. The actual mode can readily be determined by analogy to known methodologies and will depend on the particular disease state being treated, its severity, and the age and condition of the patient. They may be administered orally in tablet, capsule or elixir form, or parenterally in the form of a solution or suspension. For injection purposes, the medium used will be a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethylsulfoxide, complex forming agents (for example, ethylenediaminetetraacetic acid), high molecular weight polymers (for example liquid polyethylene oxide) for viscosity regulation or polyethylene derivatives of sorbitan anhydrides.

The total routine (e.g., daily, weekly, monthly, etc.) dose of the compounds according to the present invention will be that sufficient to result in an in vivo protein kinase C inhibitory concentration. The inhibitory concentration will generally comprise a range, the midpoint of which is the experimentally measured concentration for 50% inhibition of e.g., PMA-induced attachment or cell growth of the compound, and the limits of the range being concentrations which are a factor of 10 above and below the 50% inhibitory concentration. For example, if the experimentally measured inhibitory concentration is 5 μmolar, the desired inhibitory concentration to be achieved will be approximately 5 to 500 μmolar. One of skill in the art can readily ascertain the optimum dosage to use for a particular case, using as a starting point the range delineated above.

When a composition for the treatment of a disease is formulated, a compound or a physiologically acceptable salt of a compound according to this invention or a mixture thereof is shaped together with a physiologically acceptable vehicle, carrier, excipient, binder, preservative, stabilizer, flavoring and/or additive, into a unit dosage form.

Typical examples of additives that can be used in tablets and capsules are binders such as tragacanth gum, gum arabic, corn starch and gelatin; excipients such as microcrystalline cellulose, swelling agents such as corn starch, pre-gelatinized starch and alginic acid; lubricants such as magnesium stearate; sweeteners such as sucrose, lactose and aspartame; and flavorings such as peppermint. Other additives include edible oil as a liquid carrier (in capsules); and shellac, sugar and a combination thereof (tablet coating).

Parenteral injection may employ, as a vehicle to dissolve or suspend the active ingredient, water, natural vegetable oils such as sesame oil, coconut oil, peanut oil and cottonseed oil, and synthetic oils such ethyl oleate, and may also contain buffering agents, preservatives and anti-oxidants as required.

The present compounds are also capable of inhibiting the neutrophil oxidative burst. This effect is believed to be due to inhibition of protein kinase C mediated processes involved in the activation of neutrophils. The concentrations and modes of administration may be any of those mentioned above. To reduce inflammation, a topical route (e.g. cream or lotion) is generally desirable, formulated to achieve an in vivo concentration of from about 0.1 to 1000 μM, preferably 1 to 100 μM of the inhibitory compound.

The method of this invention may be carried out by directly contacting an inhibitory compound or composition according to the invention with protein kinase C. However, it is also possible, and within the scope of the invention, to carry out the above method indirectly, e.g., by administering a compound or composition which has an in vivo activity of inducing production of one of the inhibitory compounds of this invention and thereby causing inhibition of protein kinase C. Precursors of sphingosine or sphinganine which are converted into sphingosine (see FIG. 3) or sphinganine in vivo may be administered to living cells to result in protein kinase C inhibition.

Further, pro-drug precursors which are converted in vivo into a protein kinase C inhibitor are within the scope of this invention. For example, compounds of this invention having an N-lower acyl ($C_1$ to $C_8$) group can be cleaved in vivo by enzymes such as amidases or esterases to produce inhibiting compounds according to this invention. The nitrogen may be acylated with acetyl, propionyl, etc., or with an amino acid (i.e., one of the 20 naturally occurring amino acids such as glycine, lysine, etc.) or a peptide, which can be cleaved in vivo. Other precursors produced by analogy to conventional pro-drug methodology are also within the scope of this invention. Such precursors of protein kinase C inhibitors may be administered in the same manner to achieve similar concentrations as in the case of the direct inhibitors as described above. Compounds which act as cellular messengers and which elicit an increased intracellular concentration of a naturally occurring inhibitor of protein kinase C also fall within the scope of the invention. Examples of such compounds are chalones such as transforming growth factor-$\beta$ and fibroblast growth regulator.

The concentration of such precursors or pro-drugs required to result in an in vivo inhibitory concentration of the direct inhibitor, may be determined experimentally by way of the assays described herein or by other standard assays. Undue experimentation would not be required.

The invention now being generally described, the same will be better understood by reference to certain specific examples which are included herein for purposes of illustration only and are not intended to be limiting of the invention or any embodiment thereof, unless specified.

EXPERIMENTAL EXAMPLES

I. Inhibition of Phorbol Ester-Dependent Differentiation of Human Promyelocytic Leukemic (HL-60) Cells by Sphinganine and Other Long-Chain Bases

Materials

RMPI 1640 medium was purchased from Gibco (Grand Island, N.Y.) and defined bovine calf serum was from HyClone Laboratories (Logan, UT). Fatty acid-free bovine serum albumin and all other tissue culture reagents were obtained from Sigma (St. Louis, Mo.). The sphingolipid standards: erythro-dihydrosphingosine (sphinganine), sphingosine, N-palmitoyldihydrosphingosine, and ceramides (from bovine brain sphingomyelin) were purchased from Sigma; N-acetylsphinganine and 3-ketosphinganine were synthesized according to Gaver and Sweeley, *J. Am. Chem. Soc.* 88, 3643–3647, 1966. The other homologs were provided by Dr. Dennis Liotta at Emory University. Phorbol 12-myristate 13-acetate (PMA) was purchased from LC Services Corp. (Woburn, MA) and [$^3$H]phorbol dibutyrate (8.3 Ci/mmol) was from Amersham; 1,2-dioctanoylglycerol was obtained from Avanti Polar Lipids (Birmingham, Ala.).

The [3-$^3$H]sphinganine was synthesized by the reduction of N-acetyl-3-ketosphinganine (Gaver and Sweeley) by NaB$^3$H$_4$ (Amersham, Arlington Heights, Ill.) followed by acid hydrolysis, and purified by silica gel column chromatography (Unasil, Clarkson Chemical Co., Williamsport, Pa.). The product yielded a single spot coincident with sphinganine when examined by TLC with silica gel H plates developed in CHCl$_3$:methanol:2N NH$_4$OH (40:10:1). The specific activity was adjusted to 17,000 cpm/nmol by quantitating the amount of sphinganine as the TNBS derivative Yamamoto and Rouser, *Lipids* 5, 442–444, 1970.

Cell Culture

The HL-60 cells (obtained from the American Type Culture Collection, ATCC CCL240) were grown at 37° as a suspension culture in 175 cm$^2$ Nunc tissue culture flasks (Vangard International, Neptune, N.J.). The cells were subcultured at a density of $0.25 \times 10^6$ cells/ml and used between passage numbers 30 and 40.

Incubation of HL-60 Cells

Cells were centrifuged at 600 g for 3 min, and added at $1 \times 10^5$ cells per well in 12-well culture dishes. Medium, PMA, and long-chain bases (prepared as the 1:1 molar complex with fatty acid-free bovine serum albumin) at the indicated concentrations were added for a total volume of 2.0 ml. After the desired times, the cells in suspension were counted and checked for viability (trypan blue exclusion) with a hemacytometer. The attached cells were quantitated by measuring DNA content according to the method of West et al (*Anal. Biochem.*, 147, 289–295, 1985) and by assaying for acid phosphatase according to the method of Schnyder (*J. Exp. Med.*, 148, 434–445, 1978).

When 1,2-dioctanoylglycerol was used, the cells were treated essentially as described by Ebling et al *Proc. Natl. Acad. Sci. U.S.A.* 82, 815–819, 1985. Sphinganine was added to the cells, then dioctanoylglycerol in 1 μl of ethanol to yield 100 μM, followed by additional maintenance additions of 20 μm diacylglycerol every 2 h for 12 h.

Displacement of Phorbol by Sphinganine

Competitive binding assays were conducted as described by Goodwin and Weinberg (*J. Clin. Invest*, 70, 699–706, 1982 and Ebling et al (*ibid.*). Approximately $1 \times 10^6$ cells/ml were incubated with 12 nM [$^3$H]phorbol dibutyrate (8.3 Ci/mmol) and varying concentrations of sphinganine (1:1 with BSA) for 1 h at 37°. The cells were recovered on Millipore filters, washed, and counted. The data were corrected for nonspecific binding by subtracting the cpm obtained in the presence of 300 nM PMA.

Kinetics of [3-$^3$H]sphinganine Uptake by HL-60 Cells

Approximately $1 \times 10^6$ HL-60 cells in 1 ml of medium were mixed with an equal volume of medium containing 2.5 μm [3-$^3$H]sphinganine (equimolar with BSA). After varying time intervals, an aliquot of the cells was removed and counted and a portion was extracted as described below. The extracts were applied to Silica gel H plates and developed in CHCl$_3$:methanol: 2N NH₄OH (40:10:1, v/v/v), air dried, sprayed with Amplify (Amersham), and subjected to fluorography. Radiolabel was observed in only three regions of the chromatogram, coincident with: ceramides near the solvent front, sphinganine with an Rf of approximately 0.45, and in a region near the origin that encompassed sphingomyelin and other more polar complex sphingolipids (Rf of 0.1 to 0.2).

Analysis of Long-chain Bases

From 1 to $4 \times 10^7$ cells were recovered by centrifugation, washed thrice with phophate buffered saline, and extracted immediately by a minor modification of the procedure of Bligh and Dyer (*Canad. J. Biochem.*, 37, 911-917, 1959): 1.5 ml of chloroform:methanol (1:2) were added and mixed thoroughly; 1 ml each of chloroform and water were added and the two phases were separated by centrifugation; the upper phase was discarded, and the chloroform phase was washed twice with water and dried by passage through a small column containing $Na_2SO_4$. The extracts were saponified in methanolic KOH (0.1.M, and incubated at 37° for 1 h) to remove ester-containing glycerolipids. The DNP-derivatives were prepared according to Braun and Snell (*J. Biol. Chem.*, 243, 3775, 3783, 1968) as follows: the lipids were dissolved in 50 μl of methanol-ether (1:1), then 0.5 ml of 0.2% fluorodinitrobenzene (Sigma) in methanol-ether (1:1) and 0.5 ml of 2M $K_3BO_3$ (pH 9.6) were added. After incubating for 1 h at 37°, 2 ml of ether and 2 ml of water were added. The ether was collected and the aqueous layer was reextracted with an additional 1 ml of ether. The combined ether extracts were washed with 2 ml of water and dried over $Na_2SO_4$, and the solvent was removed under a stream of $N_2$. The recovery of [³H]sphinganine (60%) was used to correct for losses during extraction. For each experiment, the DNP-derivatives of standard sphingosine, sphinganine (dihydrosphingosine), and phytosphingosine (Sigma) were also prepared.

The derivatives were dissolved in 50 μl of methanol-5 mM potassium phosphate (pH 7.0) (90:10) and 10 μl was injected onto a $0.5 \times 25$ cm $C_{18}$-column (ISCO) and eluted isocratically with this same solvent. The derivatives were detected at 360 nm with an ISCO $V_4$ Detector. The standard sphinganine eluted at 11.2 min and sphingosine at 9 min, and both were well resolved from other species.

Statistical Methods

Data given in tables and figures are results typical for several different experiments. The results are expressed as means ± SD and the significance of differences between groups was evaluated with the Student's t-test for unpaired data.

RESULTS

Effect of Sphinganine on Cell Growth

The effect of sphinganine on HL-60 cell viability and growth was investigated because sphinganine has been reported to alter growth and to be cytotoxic for Chinese hamster ovary cells (Merrill, *Biochem. Biophys. Acta.*, 754, 284-291, 1983). Sphinganine was chosen over sphingosine because the former is available commercially as a homogeneous compound whereas the latter is a mixture of various homologs.

Untreated cells doubled during the first 24 h (FIG. 5), and this was not changed by 1 μM sphinganine, but both 2.5 and 5 μM limited growth. None of the cells exhibited a loss of cell viability for the first 24 h. By the second day, all concentrations of sphinganine were still somewhat inhibitory; 1 and 2.5 μM inhibited growth without cytotoxicity whereas 5 μM resulted in significant cell death. The change in total cell numbers between day 2 and 3 indicated that growth inhibition had ceased for the cells in 1 and 2.5 μM sphinganine. This may have been due to removal of sphinganine by metabolism (see below).

These effects depended on both the cell number, which probably reflected surface dilution, and the sphinganine to albumin ratio; therefore, these parameters were kept constant except where noted.

Effects on PMA-Induced Adherence and Growth Inhibition

Upon adding 8 nM PMA, growth of the HL-60 cells was inhibited by 70% within 24 h and the majority of the cells (61%) attached to the petri dish (Table I), which is typical for this cell line. When 1 μM sphinganine was also added, the cells continued to grow and only 26% of the total adhered. These data establish that sphinganine prevented PMA-induced growth inhibition at a concentration where sphinganine itself did not affect growth (cf., Table I and FIG. 5).

Because the cells in sphinganine continued to grow, the number available for adherence in response to PMA was higher. This results in similar numbers of adherent cells (i.e., $0.51 \times 10^5$ for PMA plus sphinganine versus $0.76 \times 10^5$ for PMA alone, or a 33% difference) while the adherent cells as a % of the total was much lower (i.e., a 74% difference). Adherence has been expressed as the % of the total viable cells to normalize for difference in growth.

Adherence was further limited to 17.6±6.4% and 15.0±2.1% by 2.5 and 5 μM sphinganine, respectively, without decreasing cell viabilities. Bovine serum albumin added alone at equivalent concentrations had no effect on growth or adherence.

Acid Phosphatase Activities of Treated Cells

For a more quantitative index of differentiation, the acid phosphatase activities of suspended and attached cells were compared (Table II). Essentially, all of the acid phosphatase activity was associated with the cells in suspension until PMA treatment, when varying percentages were transferred from the media to the dish. Sphinganine caused a concentration-dependent increase in the activity remaining in suspension and a decrease in the adherent activities, which reflects inhibition of cell adherence.

Inhibition of Phorbol Dibutyrate Binding by Sphinganine

Figure 6:
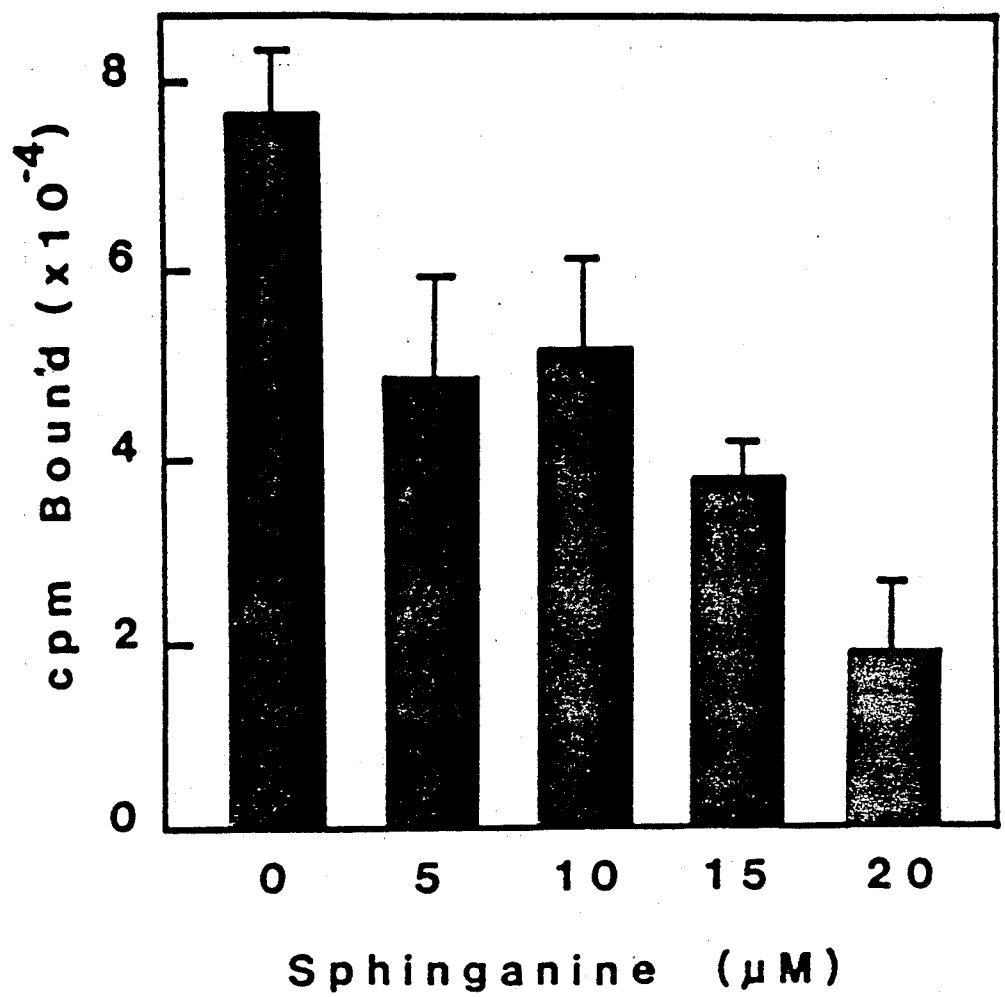
FIG. 6: Competition of Sphinganine for Phorbol Dibutyrate-Binding by HL-60 Cells. Sphinganine at the indicated concentrations or fatty acid-free bovine serum albumin at 20 μM was added to the cells with 12 nM [$^3$H]phorbol dibutyrate and binding (including correction for nonspecific binding) was determined as described in the Experimental section.
Figure 7:
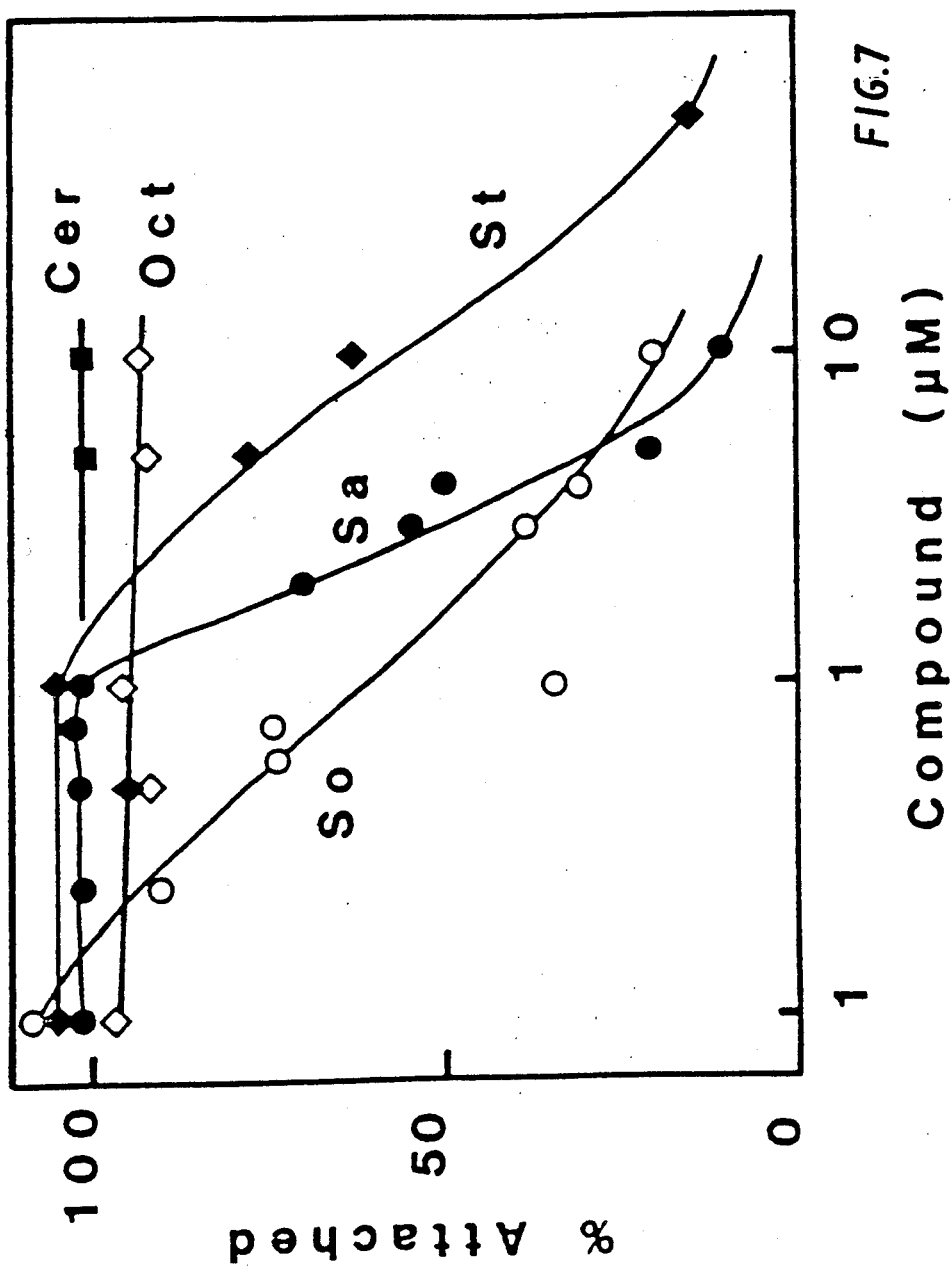
FIG. 7: Effect of Different Long-chain Bases on HL-60 Cell Attachment. The different compounds were added to the cells with 8 nM PMA and the % attachment determined as described in the Experimental section. The compounds used were sphingosine (So), sphinganine (Sa), stearylamine (St), octylamine (Oct), and ceramide (similar results were obtained with bovine brain ceramides and N-palmitoylsphinganine).
Figure 8:
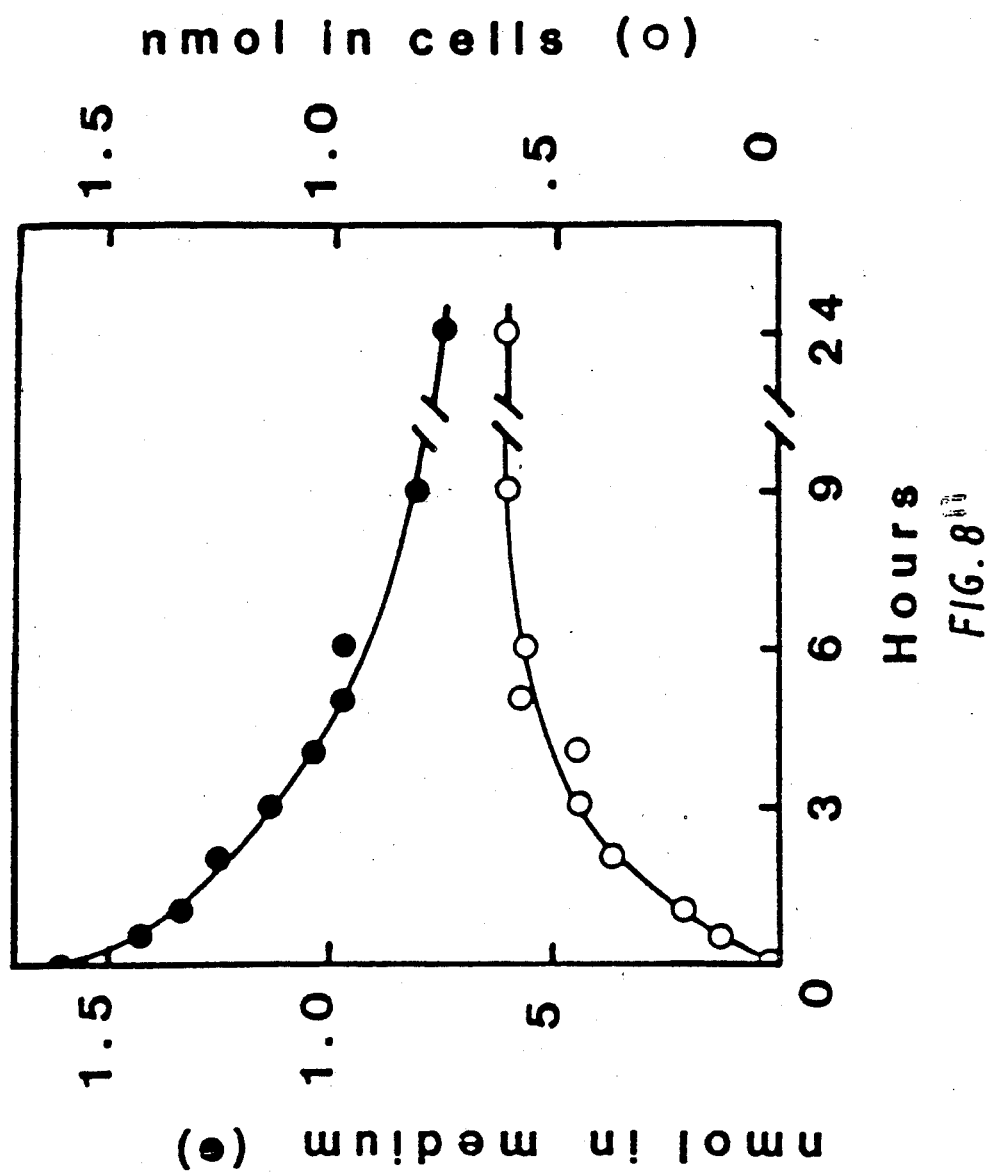
FIG. 8: Kinetics of Sphinganine Uptake by HL-60 cells. Approximately $1 \times 10^6$ cells were suspended in medium containing 1 μM [3-$^3$H]sphinganine and after different intervals of incubation at 37° aliquots were removed for measurement of the radiolabel in the medium and associated with the cells.
Figure 9:
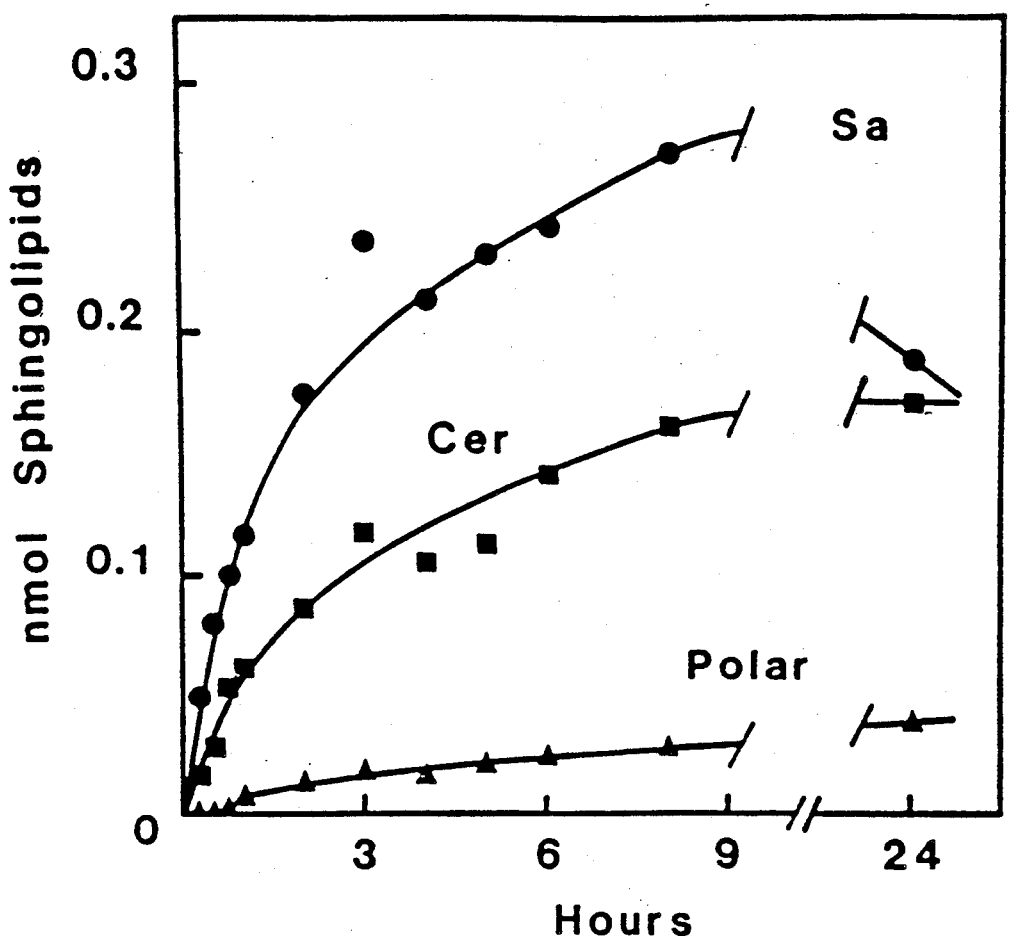
FIG. 9: Levels of Different [$^3$H]sphingolipids in HL-60 Cells at Various Time-points. The lipids from the experiment described in FIG. 8 were separated by thin-layer chromatography and visualized by fluorography. The radiolabel was coincident with ceramide, sphinganine, and polar sphingolipid standards and was quantitated by liquid scintillation counting.

The effect of sphinganine on phorbol dibutyrate binding was investigated because the blockage of attachment may be due to inhibition of protein kinase C, which is thought to be the phorbol ester receptor of HL-60 cells. Sphinganine blocked [³H]phorbol dibutyrate binding (FIG. 6), with 50% inhibition at approximately 15 μM. Addition of 20 μM bovine serum albumin alone did not alter binding significantly (8%).

This concentration of sphinganine was higher than that resulting in 50% inhibition of attachment, but a higher cell number and shorter incubation time was used for binding. Therefore, less sphinganine would have been taken up by the cells in the binding experiment, and the effective concentration in the membrane would probably also be lower.

Inhibition of Diacylglycerol-Induced Cell Attachment by Sphinganine

Dioctanoylglycerol, a cell-permeate activator of protein kinase C, also induces HL-60 cell differentiation. Dioctanoylglycerol was added at 100 μM with or without sphinganine in an initial loading dose, and additional dioctanoylglycerol was given to the cells in maintenance doses (20 μM) every 2 h for 16 h total. Sphinganine reduced adherence by 50% at approximately 5 μM (Table III). This trend was observed in three separate experiments; however, more precise comparisons were thwarted by variability in the response of the cells to dioctanoylglycerol, which must be added as described above to elicit differentiation.

Structural Specificity of the Inhibition

Figure 3:
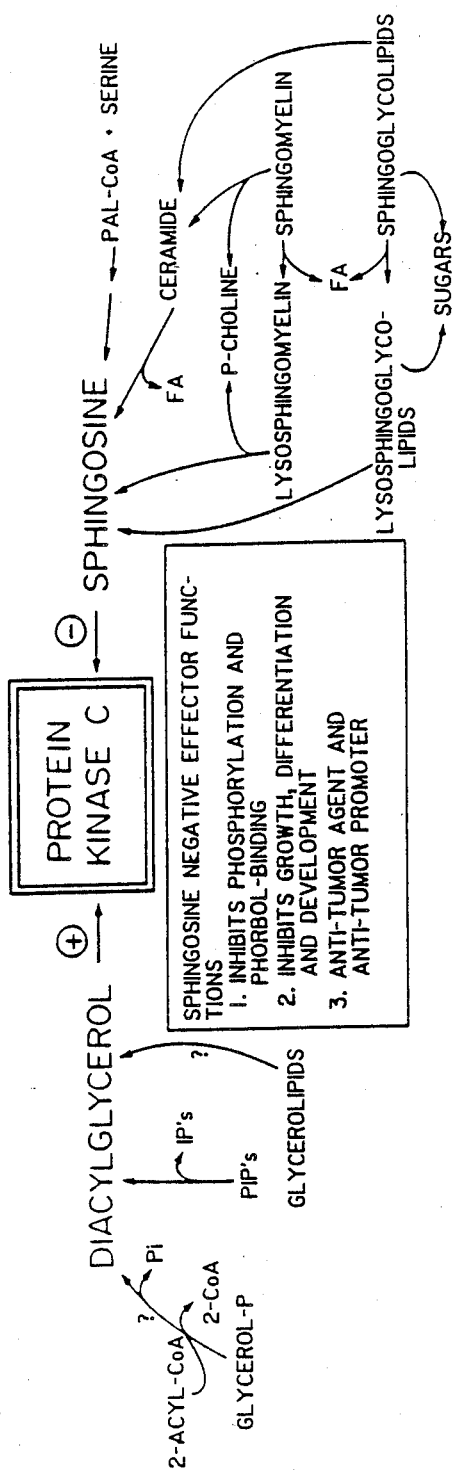
FIG. 3: Positive and negative effectors of Protein kinase C. An overall view of the complex metabolism of glycerolipids producing diacylglycerol "second messengers" and sphingosine "negative protein kinase C effectors" is shown. PIP's stand for the phosphatidylinositol phosphates. The inventors recognize that numerous routes could underlie the arrows and that more than one enzyme may lie under a given arrow. The question of whether sphingosine arises directly from palmitoyl-CoA and serine or via dihydroceramide is not illustrated. Sphingomyelin synthesis occurs by the reaction, phosphatidylcholine+ceramide→sphingomyelin+DAG. Evidence that this enzyme resides in the plasma membrane provides another potential route for DAG formation. The figure also points out how the negative effector (and positive effector) functions of sphingosine may be involved in biochemistry, cell biology and pathology. Consideration of sphingosine providing a functional regulatory link for sphingolipids should not be ignored.

The concentration dependence of sphinganine inhibition of PMA-induced attachment is shown in FIG. 3; results of similar experiments using other long-chain bases are also shown. Sphinganine at 3 μM caused 50% inhibition and sphingosine, the predominant long-chain base found in mammalian sphingolipids, caused 50% inhibition at 1 μM. Stearylamine, which is structurally related but lacks the 1,3-dihydroxy groups, effected similar inhibition at 10 μM. Other evidence for the minimal involvement of the 3-hydroxyl was similar inhibition by 3-ketosphinganine (not shown).

Both the free amino and the long alkyl chain were important. Ceramides from bovine brain and N-palmitoyldihydrosphingosine were not inhibitory, nor was N-acetylsphinganine at up to 500 μM. Octylamine did not inhibit, nor did another short-chain analog of sphinganine, 1,3-dihydroxy-2-amino-3-phenylpropane.

Effects of Sphinganine on Cell Morphology and Histochemical Parameters

Expression of most other signs of HL-60 cell differentiation requires longer time periods after treatment with PMA. For these experiments, the cells were examined on day 3 for adherence and acid phosphatase activity (Table IV) and morphology and the marker enzymes alpha-naptholacetate (ANA) esterase and acid phosphatase (Table V).

By day 3, most of the viable cells and acid phosphatase activities were adherent (Table IV). The majority of the cells had lost promyelocyte morphology, and resembled macrophages with visibly higher alphanaptholacetate (ANA) esterase activity (Table V). Acid phosphatase activities were higher for adherent cells when expressed as activity per $10^5$ cells, increasing 3-fold upon addition of PMA with and without sphinganine. This is a typical response of HL-60 cells to PMA.

None of the few viable cells in suspension had clear signs of differentiation.

Kinetics of Sphinganine Uptake and Metabolism

Figure 4A:
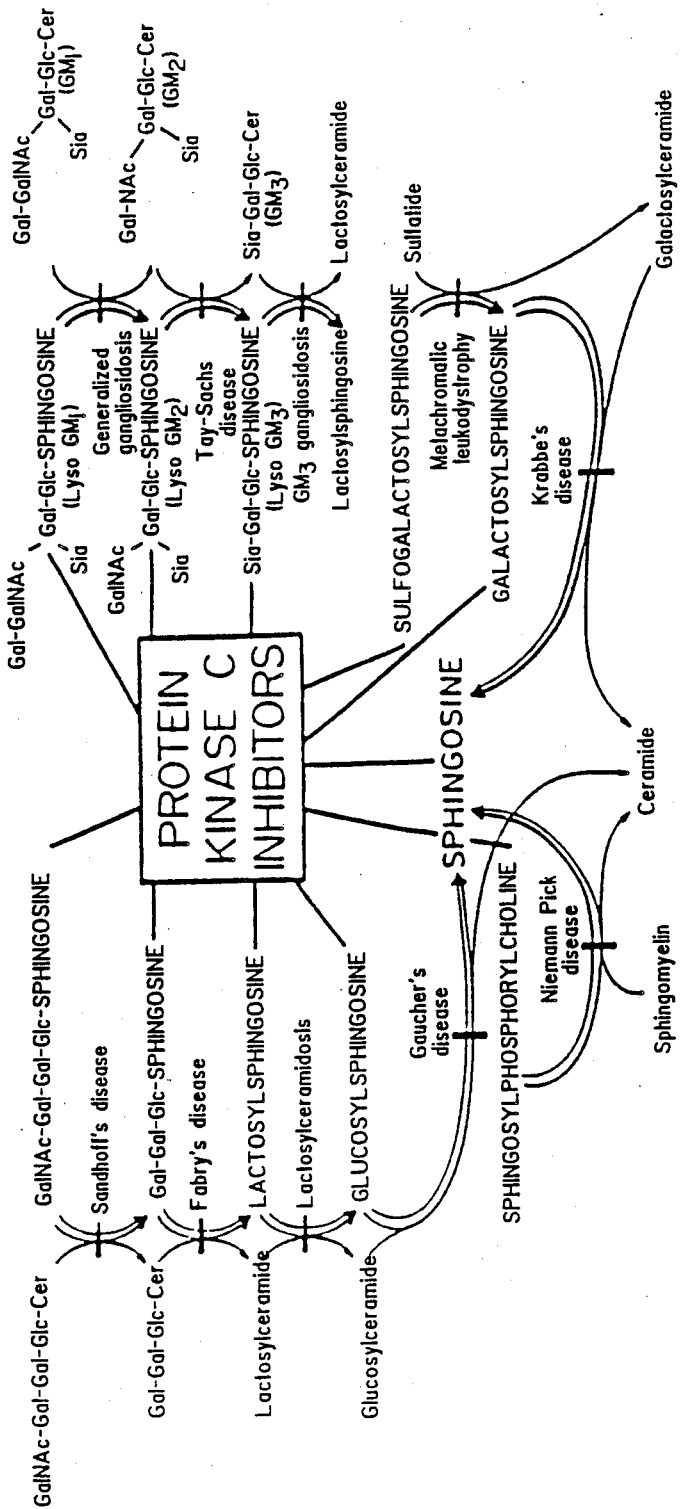
FIG. 4: Lysosphingolipids/sphingosine inhibition of Protein Kinase C. A. This figure illustrates the relevance of lysosohingolipids/sphingosine inhibition of protein kinase C/signal transduction to the sphingolipidosis
Figure 4B:
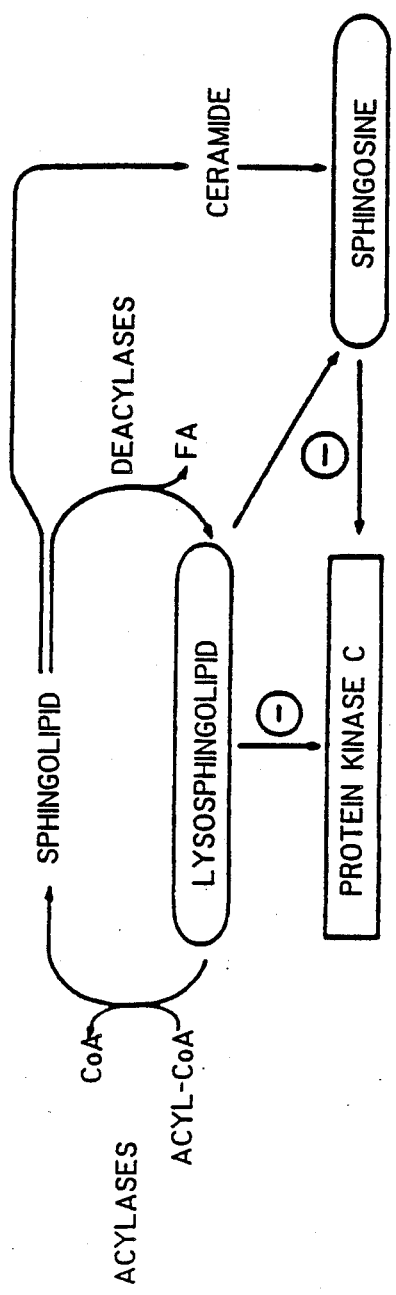
Figure 5:
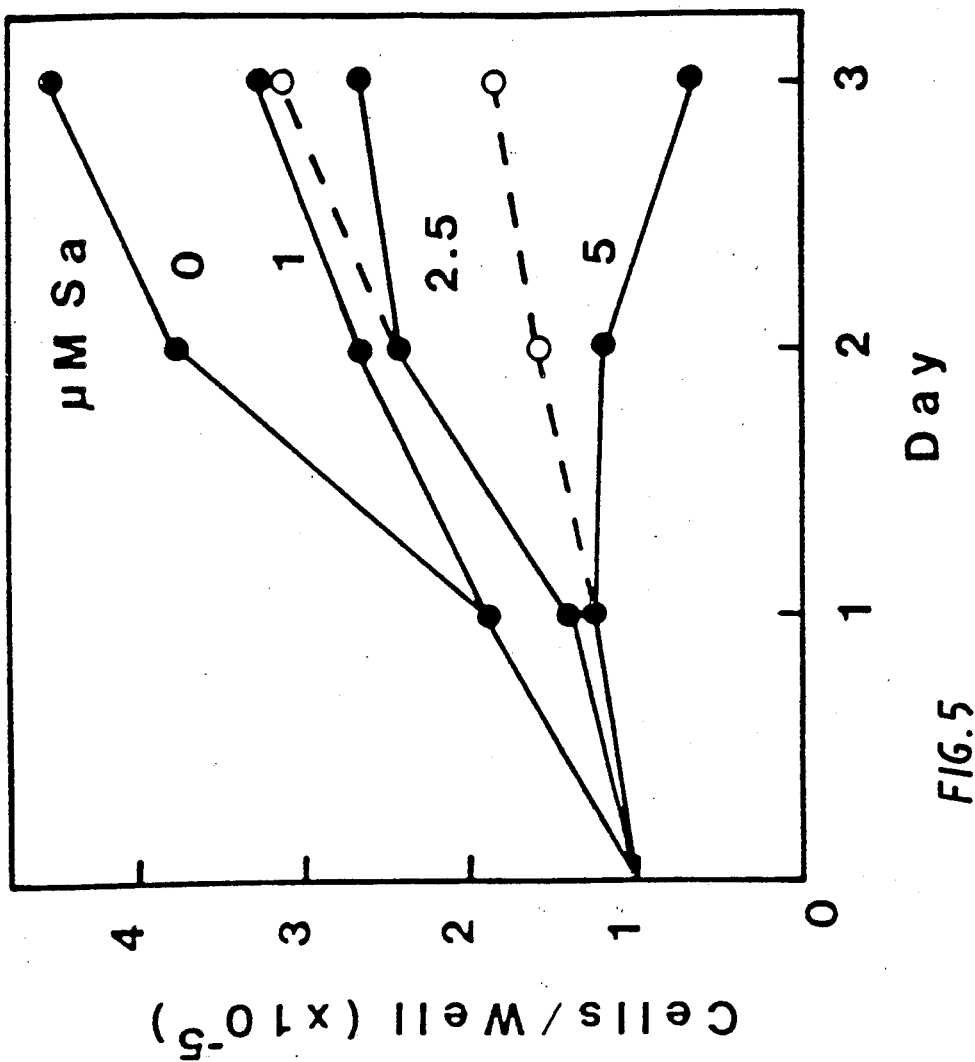
FIG. 5: Effect of Sohincanine on HL-60 Cell Growth. Sphinganine at varying concentrations was added to 1×10$^5$ cells and incubated for the times shown. The closed circles are viable cells (all groups had >90% viability, except where otherwise indicated) and the open circles reflect both viable and non-viable cells.

The rate of disappearance of [$^3$H]sphinganine from the culture medium and its appearance in the cells is shown in FIG. 4. Approximately half of the sphinganine was taken up from the medium by the cells within 6 hr. Free sphinganine accounted for most of the cellular radiolabel (FIG. 5). A large fraction was rapidly incorporated into ceramides but little was found in more polar sphingolipids (sphingomyelin and glycolipids). By days 2 and 3, only 0.07 and 0.06 nmol of free [$^3$H]sphinganine was associated with the cells. The radioactivity that could not be accounted for in lipids was in the aqueous phase and may reflect degradation, which produces $^3H_2O$.

The removal of sphinganine by metabolism probably accounts for the absence of inhibition by day 3.

Free Long-chain Base Content of HL-60 Cells

The endogenous level of long-chain bases in HL-60 cells was quantitated by HPLC. Sphingosine was the major free long-chain base detected (i.e., >80% of the total) and was present at 12.3±1.2 pmoles/$10^6$ cells. Since leukocytes contain approximately 5 nmol of sphingolipids/$10^6$ cells, this corresponds to about 0.2% of the total long-chain bases present in the cells. Previous studies have found that free long-chain bases are not artifacts of the isolation or derivatization procedures.

TABLE I

Effects of Sphinganine on the Response of HL-60 Cells to PMA

Cells were incubated for 24 h with 1 μM sphinganine, 8 nM PMA, or both, and then the total number of viable cells in suspension and attached to the petri dish was determined.

| | Treatment | | | |
|---|---|---|---|---|
| Period of Incubation | None | Sa Cells/dish ($\times 10^{-5}$) | PMA | PMA + Sa |
| 0 h | 1.0 ± 0.1 | — | — | — |
| 24 h | 1.78 ± 0.18 | 1.91 ± 0.14 | 1.25 ± 0.05[a] | 1.95 ± 0.15 |
| | | % Adherence | | |
| 24 h | 4.5 ± 1.5 | 3.7 ± 0.7 | 61.3 ± 1.0 | 25.5 ± 7.7 |
| | | % Viability | | |
| 24 h | 97 | 95 | 80 | 93 |

[a] $P < 0.05$ compared to all other groups.

TABLE II

Acid Phosphatase Activities of HL-60 Cells After Treatment with PMA and Sphinganine Cells were incubated for 24 h with 8 nM PMA and varying concentrations of sphinganine and the acid phosphatase activities of the cells in suspension and attached to the petri dish were determined.

| | Acid phosphatase activity[a] (nmol/h/dish) | | Adherence |
|---|---|---|---|
| Treatment | Suspended | Adherent | (% of total) |
| No PMA | | | |
| 0 μM Sphinganine | 1.57 ± 0.08 (96%)[b] | 0.06 ± 0.02 | 4 |
| 1 μM Sphinganine | 1.53 ± 0.01 (90%) | 0.06 ± 0.03 | 4 |
| 2.5 μM Sphinganine | 1.25 ± 0.16 (98%) | 0.06 ± 0.02 | 5 |
| 5 μM Sphinganine | 0.91 ± 0.16 (87%) | 0.04 ± 0.01 | 4 |
| 8 nM PMA | | | |
| 0 μM Sphinganine | 0.11 ± 0.05 (60%) | 0.52 ± 0.01 | 83 |
| 1 μM Sphinganine | 0.22 ± 0.07 (87%) | 0.44 ± 0.11 | 67 |
| 2.5 μM Sphinganine | 0.49 ± 0.28 (94%) | 0.30 ± 0.04 | 38 |
| 5 μM Sphinganine | 0.52 ± 9.23 (80%) | 0.14 ± 0.04 | 21 |

[a] The activity of the suspended cells on day 0 was 0.84 ± 0.05 nmol/h/dish.
[b] Percent viability of suspended cells.

TABLE III

Inhibition of Dioctanoylglycerol-induced Differentiation of HL-60 Cells by Sphinganine Cells were incubated with dioctaglycerol and varying concentrations of sphinganine.

| [Sphinganine] (µM) | % Viable cells attached[a] |
|---|---|
| 0 | 100 ± 10 |
| 1.0 | 70 ± 32 |
| 2.5 | 63 ± 21[b] |
| 5.0 | 50 ± 25[b] |

[a]Compared to cells treated with diacylglycerol only.
[b]Significantly different from control ($P < 0.05$).

TABLE IV

Adherence and Acid Phosphatase Activities of HL-60 Cells After Treatment with PMA and Sphinganine for 72 h Cells were incubated for 72 h with 8 nM PMA and varying concentrations of sphinganine and the acid phosphatase activities of the cells in suspension and attached to the petri dish were determined.

| Treatment activity | Adherent cells (%) | Acid phosphatase Suspended (nmol/h/dish) | Adherent | (%) |
|---|---|---|---|---|
| No PMA | | | | |
| 0 µM Sphinganine | 8 | 2.31 ± 0.40 | 0.08 ± 0.03 | (3) |
| 1 µM Sphinganine | 9 | 2.77 ± 0.25 | 0.05 ± 0.03 | (2) |
| 2.5 µM Sphinganine | 11 | 2.35 ± 0.11 | 0.05 ± 0.02 | (2) |
| 5 µM Sphinganine | 6 | 0.24 ± 0.01 | 0.04 ± 0.01 | (14) |
| 8 nM PMA | | | | |
| 0 µM Sphinganine | 96 | 0.05 ± 0.01 | 2.20 ± 0.09 | (98) |
| 1 µM Sphinganine | 85 | 0.05 ± 0.01 | 2.95 ± 0.62 | (98) |
| 2.5 µM Sphinganine | 74 | 0.06 ± 0.01 | 3.10 ± 0.30 | (98) |
| 5 µM Sphinganine | 70 | 0.12 ± 0.08 | 0.82 ± 0.38 | (87) |

TABLE V

Markers of HL-60 Cell Differentiation After Treatment With PMA and Sphinganine

Cells were treated with 8 nM PMA and sphinganine for 3 days and examined for morphology, alpha-naptholacetate esterase (ANA), and acid phosphatase (AP) activity.

| | [Sphinganine] (µM) | | | |
|---|---|---|---|---|
| Parameter | 0 | 1 | 2.5 | 5 |
| No PMA--Suspended cells | | | | |
| Promyelocytic morphology | +++ | +++ | +++ | +++ |
| Macrophage morphology | − | − | − | + |
| ANA activity | + | + | ++ | NA[a] |
| Acid phosphatase | 0.20 | 0.25 | 0.22 | 0.16[b] |
| 8 nM PMA-Suspended cells | | | | |
| ANA activity | NA | + | + | + |
| Acid phosphatase | 0.30 | 0.19 | 0.12 | 0.06 |
| 8 nM PMA-Adherent cells | | | | |
| Promyelocytic morphology | + | + | + | + |
| Macrophage morphology | +++ | +++ | +++ | +++ |
| ANA activity | ++ | ++ | ++ | +++ |
| Acid phosphatase | 0.60 | 0.64 | 0.60 | 0.64 |

[a]Too few viable cells to score.
[b]Activity in nmol/h/10⁵ cells.

II. Sphingosine Inhibition of Protein Kinase C Activity and of Phorbol-Dibutyrate Binding in vitro and in Human Platelets

Materials[1]

Charles River CD female rats were used for the source of protein kinase C. Ultrogel AcA 44 and Ultrogel AcA 202 were from LKB. $^{32}$P-orthophosphate, Aquasol II, [-$^{32}$P]ATP, and [$^3$H]PDBu (12.5 Ci/nmol) were from New England Nuclear. Calf thymus histone type III-S, phospholipase C, thrombin, phenylmethylsulfonylfluoride, stearylamine, bovine serum albumin, phorbol dibutyrate, 4-sphingenine, threo-sphingosine and dihydrosphingosine were from Sigma. Leupeptin was from the Peptide Institute (Osaka, Japan). 1,2-Dioleoyl-sn-glycerol-3-phosphoserine, dioctanoylglycerol and 1,2-dioleoyl-sn-glycero-3-phosphocholine were from Avanti Polar Lipids, Inc. sn-1,2-Dioleoylglycerol was synthesized from dioleoylphosphatidylcholine as previously described. Triton X-100 was from Research Products International Corp. Octylamine was from Aldrich Chemical Company, Inc. Swainsonine was a gift from Harry Broquist (Department of Biochemistry, Vanderbilt University); ceramide was a gift from Jim Walsh (Department of Biochemistry, Duke University); N-acetylsphingosine was a gift from Barry Ganong (Department of Biochemistry, Duke University); 1,3-Dihydroxy-2-amino-3-phenylpropane was a gift from Dennis Liotta (Department of Chemistry, Emory University). Phorbol 12-myristate-13-acetate was from PL Biochemicals.

Methods

Partial Purification of Protein Kinase C

Protein kinase C was partially purified from rat brain as described by Hanrun et al (*J. Biol. Chem.*, 260, 10043, 1985), which is hereby incorporated by reference.

Mixed Micellar Assay for Protein Kinase C Activity

Protein kinase C was assayed with Triton X-100 mixed micelles as described by Hanrun et al, (ibid.), Sphingosine was dried down with the lipid cofactors.

[$^3$H]PDBu binding was performed as previously described (26).

Preparation of Human Platelets

Human platelets were prepared from freshly drawn blood essentially as described by Siess et al (*J. Biol. Chem*, 258, 11236, 11242, 1983). They were then suspended in modified Tyrode's buffer to a concentration of $2.5 \times 10^8$ platelets/ml.

[$^3$H]PDBu Binding to Human Platelets

Human platelets, prepared as described above, were suspended at a concentration of $2.5 \times 10^8$ platelet/ml. 50 µl of the platelets were then incubated for five minutes with the indicated concentration of sphingosine in Eppendorf microfuge tubes. Sphingosine was prepared in 50% ethanol at a concentration 100-fold the final concentration so that ethanol was kept at 0.5%. [$^3$H]PDBu was added to 10 nM and incubated with the platelets at 37° for 10 minutes. The samples were then filtered on Whatman GF/C filters pre-washed with 5 ml of modified Tyrode's buffer containing 0.1% bovine serum albumin, washed with 10 ml of the same buffer, dried, and counted in 10 ml of Aquasol II in an LKB beta counter. Non-specific binding was determined in the presence of 1 µM unlabelled PDBu and subtracted from the total counts to yield the specific binding.

40K Phosphorylation in Human Platelets $^{32}$P$_i$ at 0.2 mCi/ml was added to the platelet suspension and labelling was allowed to proceed for 75 minutes at 37° C., after which the platelets were pelleted at 600×g for 10 minutes and resuspended in Tyrode's buffer to the same concentration. They were then aliquoted in Eppendorf microfuge tubes and preincubated at 37° C. for 5 minutes with the varying concentrations of sphingosine. Platelets were then stimulated with either 5 μM dioctanoylglycerol (added as an ethanol solution with the final concentration of ethanol 0.5%), 10 μM TPA, or 1 unit/ml thrombin. The reactions were stopped after 30 seconds by the addition of an equal volume of 2× sample buffer, and the samples were then boiled for 3 minutes. 0.1 ml were then loaded on 10% sodium dodecylsulfate polyacrylamide gels and electrophoresis was performed according to the method of Laemmli (*Nature*, 227, 680–685, 1970). Gels were subsequently fixed in water/methanol/acetic acid (60:30:10), dried, and autoradiographed.

Phospholipid Quantitation

Phospholipids were extracted from whole platelets by the method of Bligh and Dyer (*Can. J. Biochem. Physiol.*, 37, 911–917, 1959). Phosphatidylserine was purified by two dimensional thin layer chromatography on Silica gel H plates developed in chloroform:methanol:acetic acid (65:25:10 v/v) in the first dimension and in chloroform:methanol:88% formic acid (65:25:10 v/v) in the second dimension. Phospholipids were quantitated by measuring phosphates according to the method of Ames (*J. Biol. Chem.*, 235, 769–775, 1960).

The data shown is representative of at least 3 sets of experiments.

RESULTS AND DISCUSSION

Figure 10:
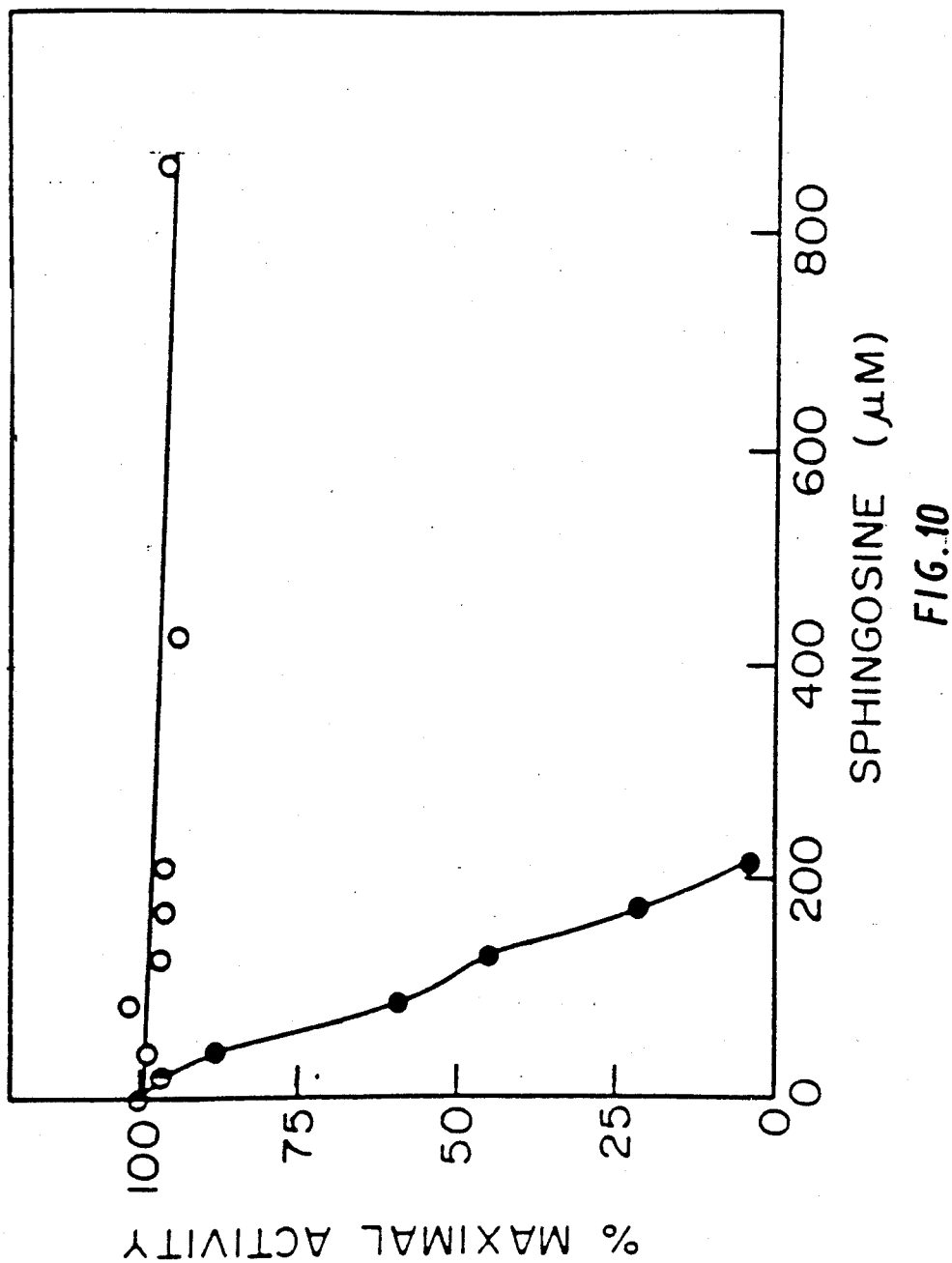
FIG. 10: Inhibition of Protein Kinase C Activity by Sohingosine. Mixed micelles were formed with 3% (w/v) Triton X-100 containing PS at 6 mol %, diC$_{18:1}$ at 2 mol % and sphingosine at 10 fold the indicated concentrations. The mixed micelles were then diluted 1:10 into the assay mixture. 1 mol % of sphingosine is equivalent to 43 μM. Effect of sphingosine on protein kinase C (●) and on protein kinase M (O). Identical results were obtained with protein kinase M when sphingosine was added in 0.3% Triton X-100 solution without PS and diC$_{18:1}$.
Figure 11A:
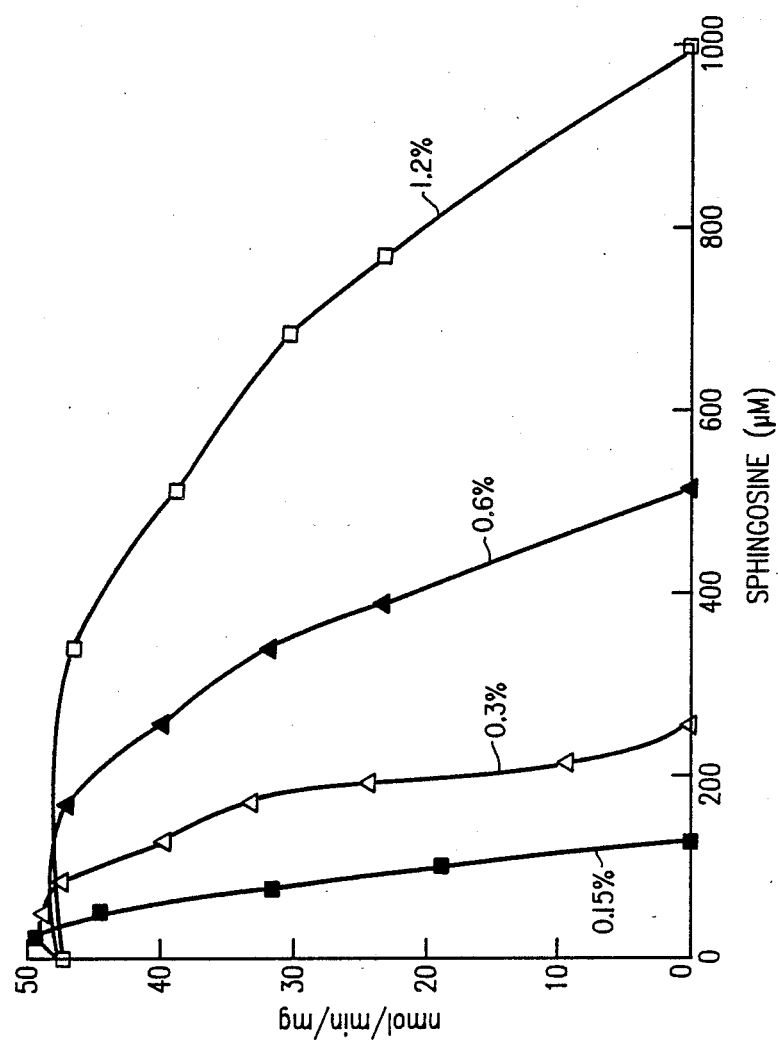
FIG. 11: Effect of Mixed Micelle Concentration on Potency of Sphincosine Inhibition. A. Mixed micelles were formed with Triton X-100 at 12% (w/v, □) 6% (▲), 3% (Δ) and 1.5% (■) containing 7 mol % PS, 1 mol % diC$_{18:1}$, and sphingosine at 10 fold the indicated concentrations. The mixed micelles were then diluted 1:10 into the assay mixture. B. Mixed micelles were formed with 3% Triton X-100, 7 mol % PS, 1 mol % diC$_{18:1}$, and 2-5 mol % sphingosine. These were then diluted 1:20 (■) 1:10 (Δ), 1:5 (▲), and 2:5 (□) into the assay mixture. In these experiments, 1 mol % sphingosine corresponds to 21.5 μM; 43 μM; 86 μM; and 172 μM respectively.
Figure 11B:
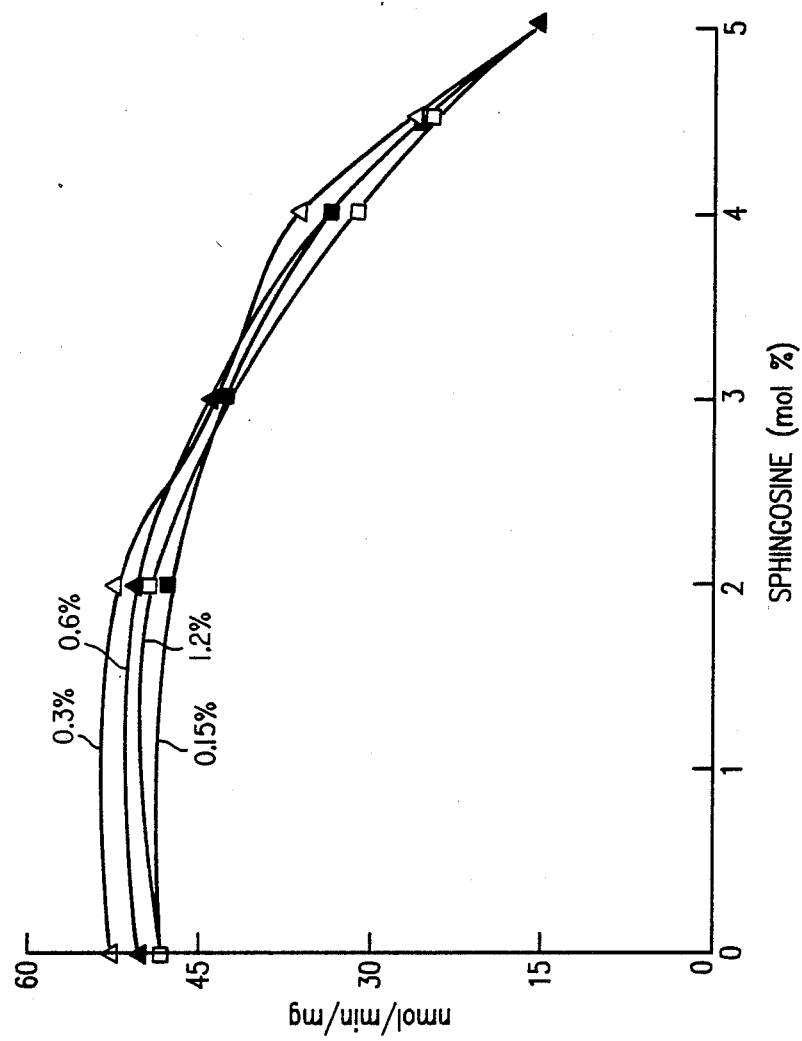

When the effect of sphingosine on protein kinase C activity was tested using the Triton X-100 mixed micelle assay containing 6 mol % PS and 2 mol % $diC_{18:1}$, sphingosine proved to be a potent inhibitor (FIG. 10). Under these conditions, the bulk concentration of PS was 260 μM and $diC_{18:1}$ was 86 μM. Therefore, 50% inhibition (100 μM) occurred on a molar basis equivalent to $[diC_{18:1}]$ or to 0.4 of [PS]. The potency of sphingosine inhibition was markedly affected by the number of Triton X-100 mixed micelles containing 7 mol % PS and 1 mol % $diC_{18:1}$ present in the assay (FIG. 11A). Thus, the effect of sphingosine was subject to surface dilution. When the data are expressed as mol %, (sphingosine:Triton X-100), sphingosine inhibition at four different levels of Triton X-100 mixed micelles (containing PS and $diC_{18:1}$) was identical (FIG. 11B) implying that it is the number of sphingosine molecules present in each mixed micelle that determines the potency and not the absolute concentration. For surface active amphipathic molecules, the expression of inhibitor potencies must be relative to the amount of surface (micelles in this case) as bulk concentrations are misleading. These results also imply that sphingosine interacts with the surface-bound protein kinase C probably by interfering with the function of its regulatory domain. To test this hypothesis, the catalytic domain (protein kinase M) was generated by proteolysis of protein kinase $C^2$. The activity of this catalytic domain which is independent of $Ca^{2+}$, phospholipid and DAG/phorbol esters was not inhibited by sphingosine (FIG. 10). Thus, sphingosine does not appear to inhibit by interaction with the active site.

Figure 12A:
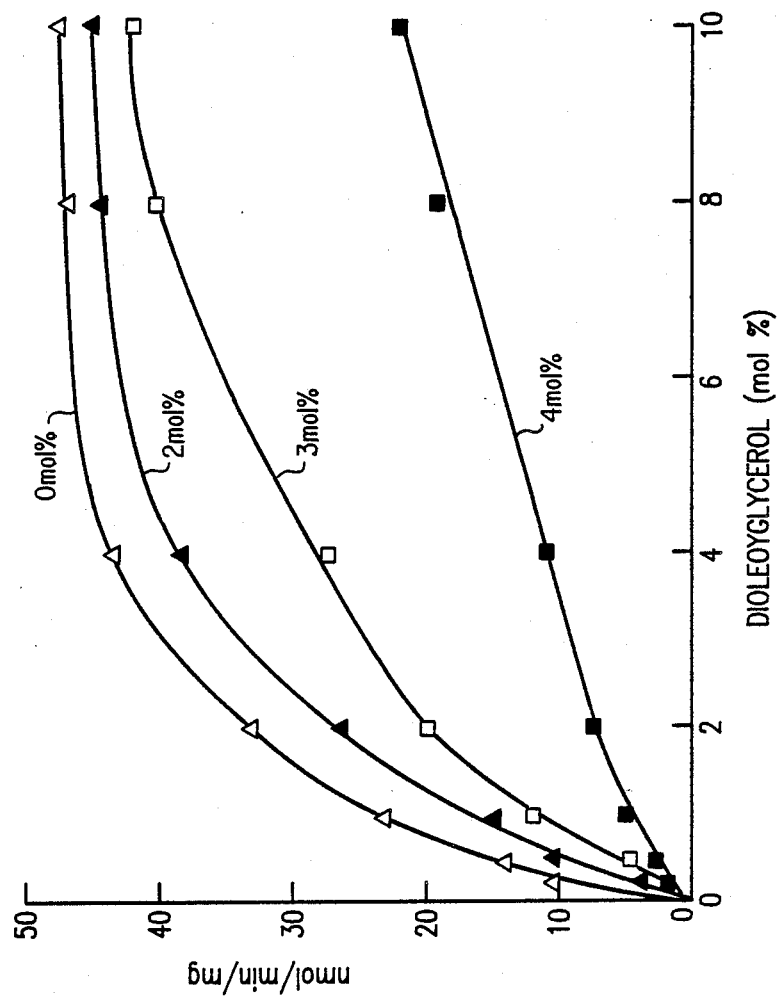
FIG. 12: Interaction of Sohincosine with Dioleoylglycerol. Mixed micelles were formed at 3% Triton X-100, 6 mol % PS, 0-10 mol % diC$_{18:1}$, and sphingosine at 0 mol % (Δ), 2 mol % (▲), 3 mol % (□), and 4 mol % (■). A. Protein kinase C activity assayed in presence of 50 μM CaCl$_2$. B. Double reciprocal plots with diC$_{18:1}$ concentration in mol %.
Figure 12B:
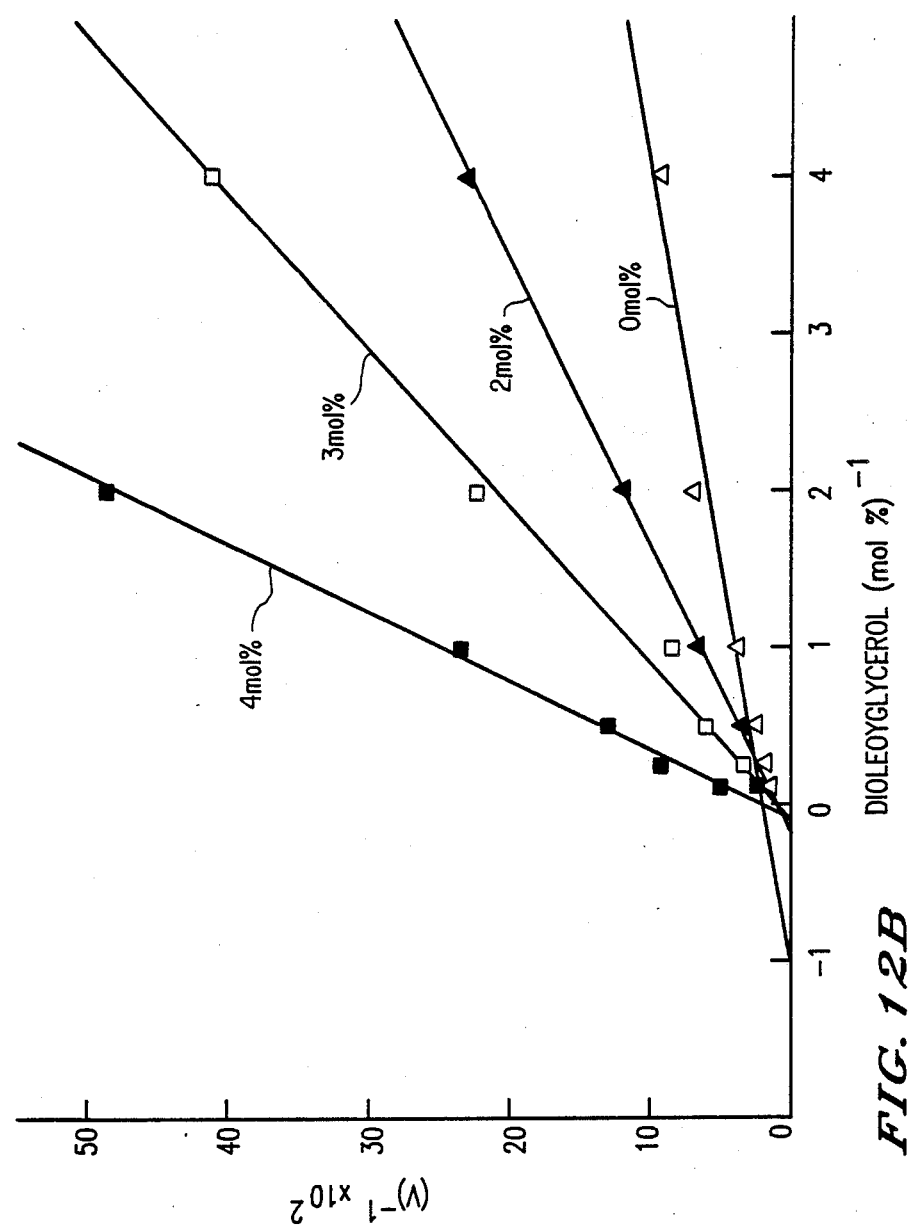

To further investigate the mechanism of sphingosine inhibition, the sn-1,2-$diC_{18:1}$ dependency of protein kinase C activation was investigated at fixed PS (6 mol %) and $Ca^{2+}$ (50 μM) and at several levels of sphingosine. Importantly, the inhibition by sphingosine was modulated strongly by $diC_{18:1}$ (FIG. 12A). Double reciprocal plots (FIG. 12B) indicated essentially a competitive type of inhibition with respect to $diC_{18:1}$. Similarly, inhibition by sphingosine was overcome by increasing concentration of phorbol dibutyrate (FIG. 13A), and double reciprocal plots (FIG. 13B) showed competitive inhibition.

Figure 14:
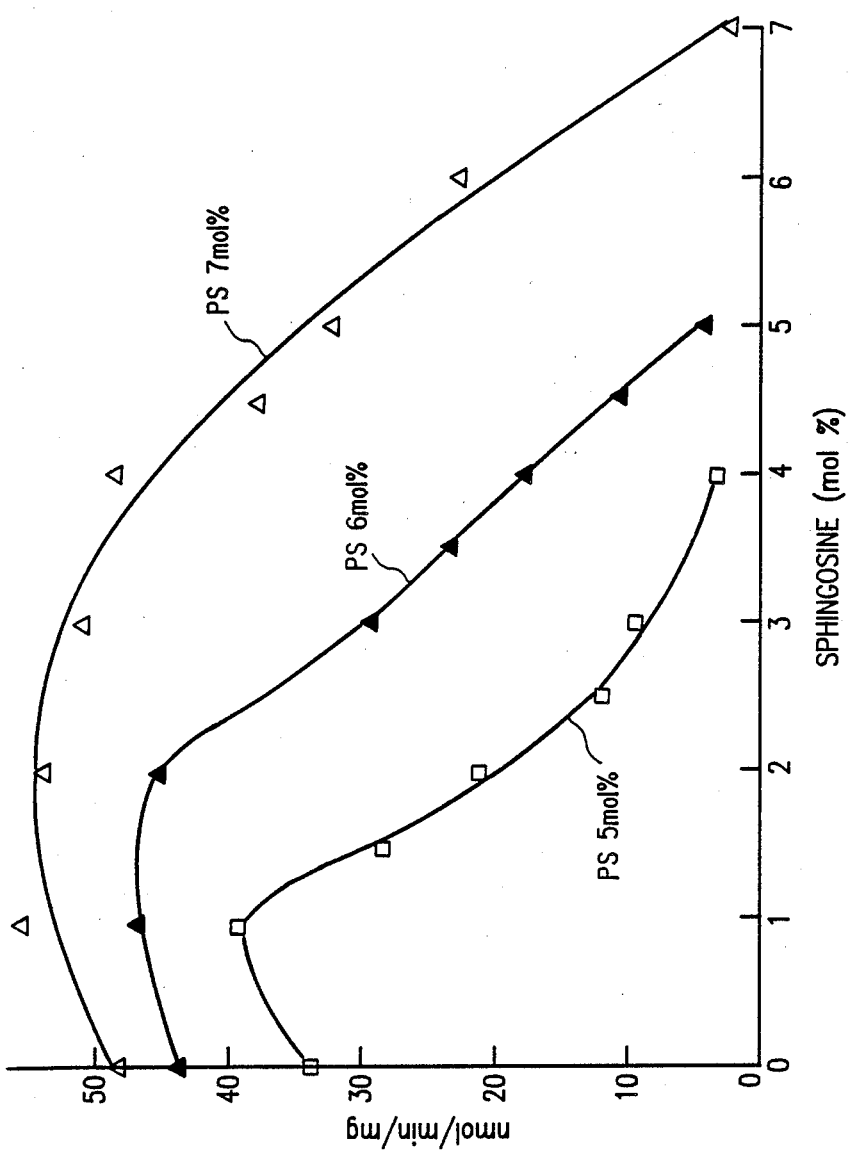
FIG. 14: Potency of Sohincosine Inhibition as a Function of Phosphatidylserine. Mixed micelles contained 2 mol % diC$_{18:1}$ and 5 mol % (□), 6 mol % (▲), and 7 mol % (Δ) PS, and variable mol % of sphingosine.

When the concentration of sphingosine was varied at 5, 6 and 7 mol % PS and fixed $diC_{18:1}$ (2 mol %), the potency was modulated markedly (FIG. 14). This was especially true when PS was not saturating at 5 mol %. Shifting from 6 to 7 mol % PS, a level at which PS becomes saturating (FIG. 15), revealed that the curves were simply not displaced on a mole for mole basis. When PS was in excess, higher concentrations of sphingosine were required for inhibition (FIG. 14).

Figure 15:
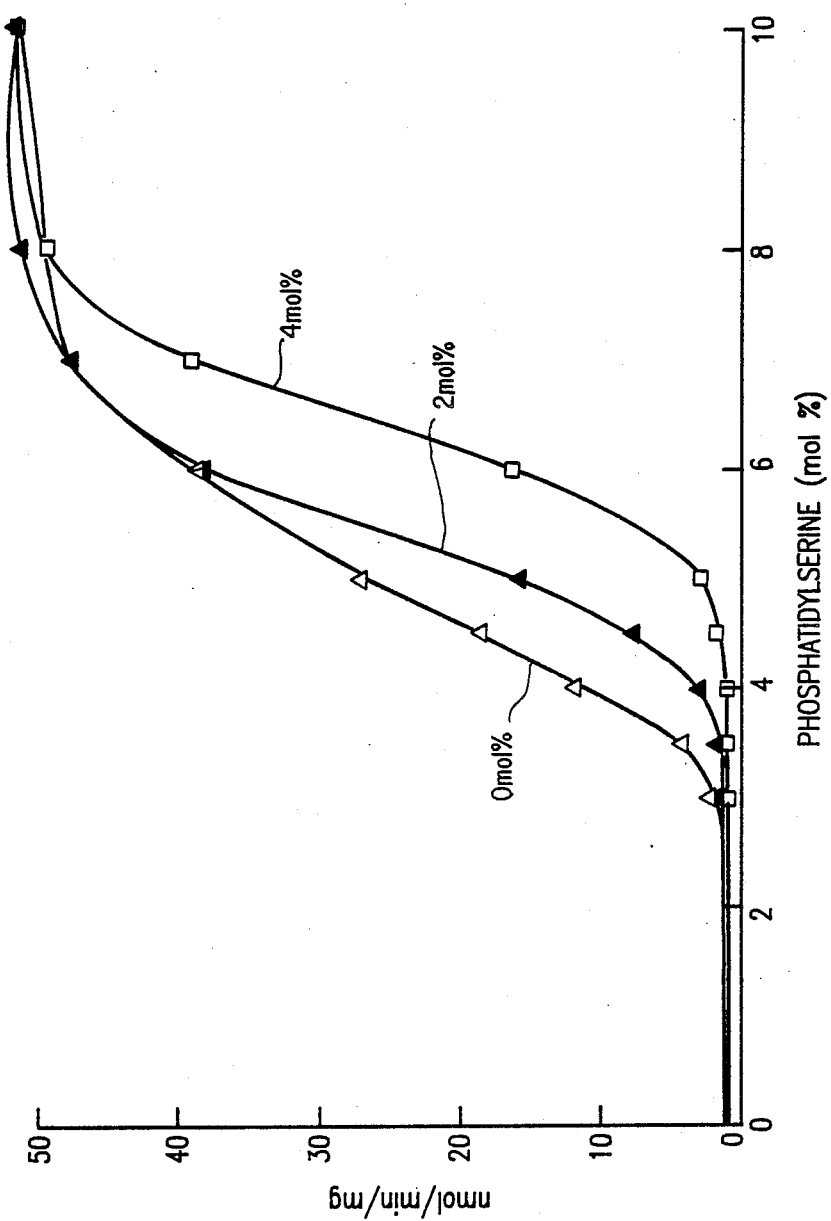
FIG. 15: Interaction of Sphingosine with Phosphatidylserine. Mixed micelles were formed with diC$_{18:1}$ at 1 mol % and sphingosine at 0 mol % (Δ), 2 mol % (▲), and 4 mol % (□), activity was measured in presence of 50 μM CaCl$_2$.

Next, the effect of 2 and 4 mol % sphingosine on the PS dependence of protein kinase C activation was investigated (FIG. 15). Interestingly, sphingosine caused a displacement of the PS dependence to higher levels which remained strongly cooperative in the presence or absence of inhibitor. When the PS dependencies were then plotted according to Hill, Hill numbers of 5.4, 6.9 and 8.8 were obtained for the curves generated at 0, 2 and 4 mol % sphingosine, respectively. Double reciprocal plots were not constructed because of the cooperativity observed with PS and the sphingosine-dependent change in Hill numbers. In that additional PS completely overcame the inhibition by sphingosine, a competitive form of inhibition appears likely.

Figure 16:
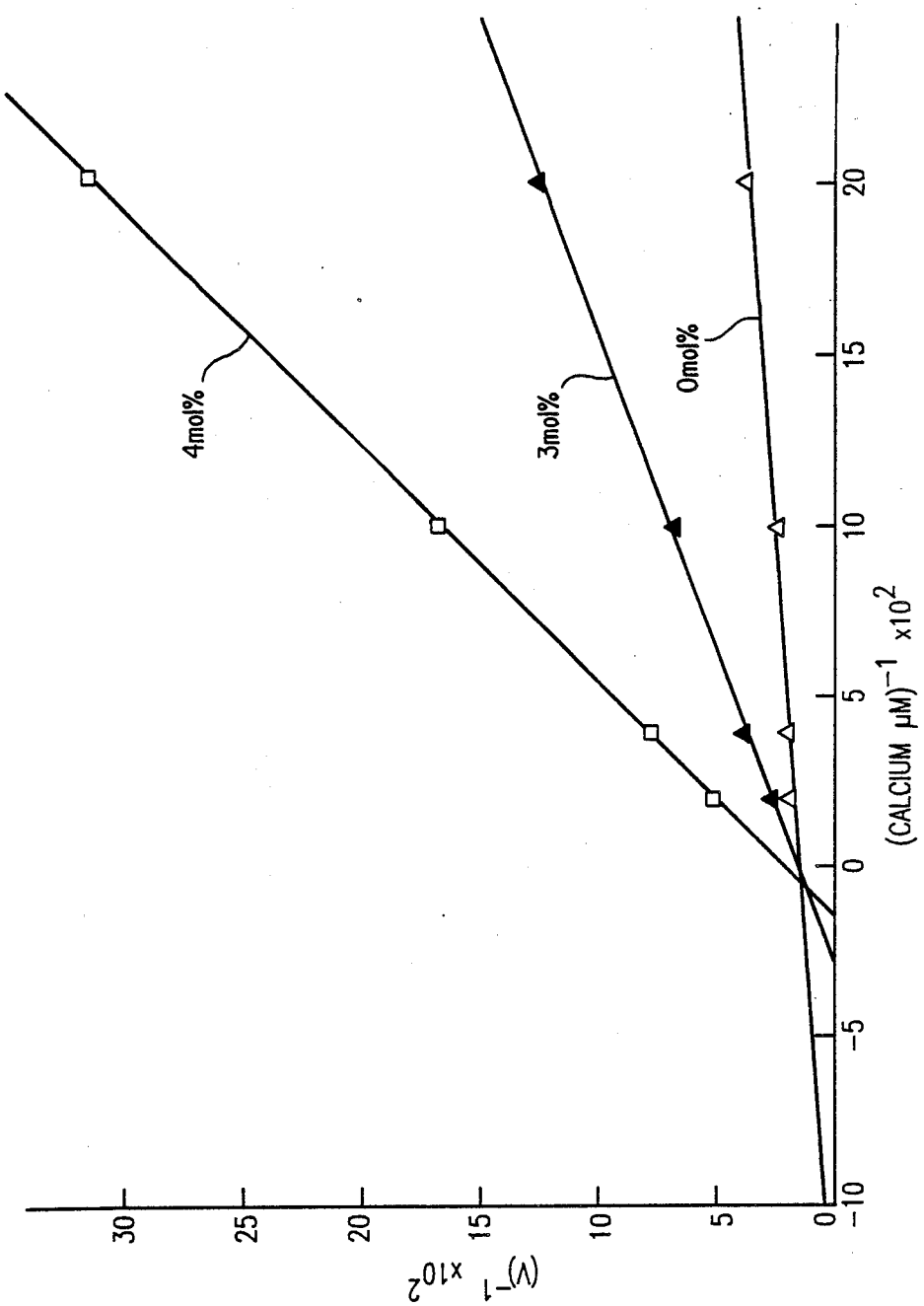
FIG. 16: Interaction of Sohincosine with Ca$^{2+}$. Mixed micelles contained 6 mol % PS, 1 mol % diC$_{18:1}$ and 0 mol % (Δ), 3 Mol % (▲) and 4 mol % (□) sphingosine.

To further explore the mechanism of sphingosine inhibition, the effect of the level of $Ca^{2+}$ employed was examined at fixed PS and $diC_{18:1}$ and at 0, 3, and 4 mol % sphingosine. Double reciprocal plots of calcium dependencies were linear and appeared competitive (FIG. 16).

Figure 13A:
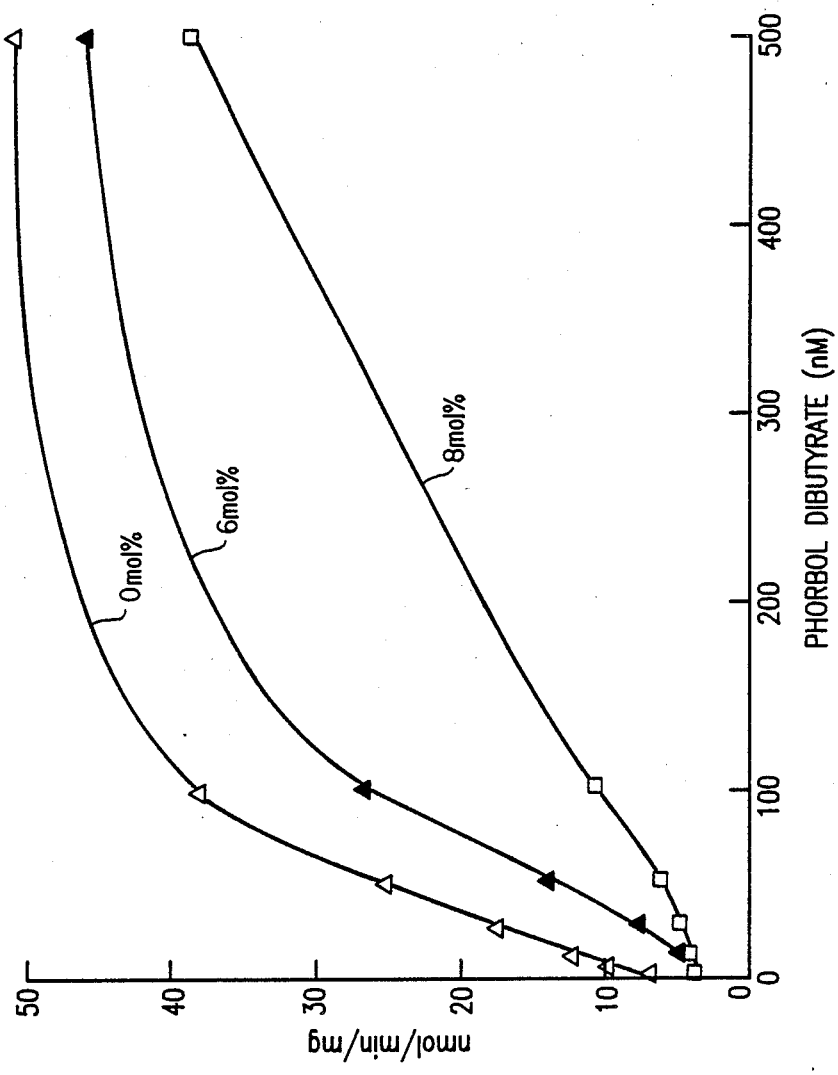
FIG. 13: Interaction of Sohincosine with Phorbol Dibutyrate. Mixed micelles were formed with 10 mol % PS and 0 mol % (Δ), 6 mol % (▲), and 8 mol % (□) sphingosine. PDBu was added as an aqueous solution. A. Protein kinase C activity assayed in presence of 10 μM CaCl$_2$. B. Double reciprocal plots of data in A.
Figure 13B:
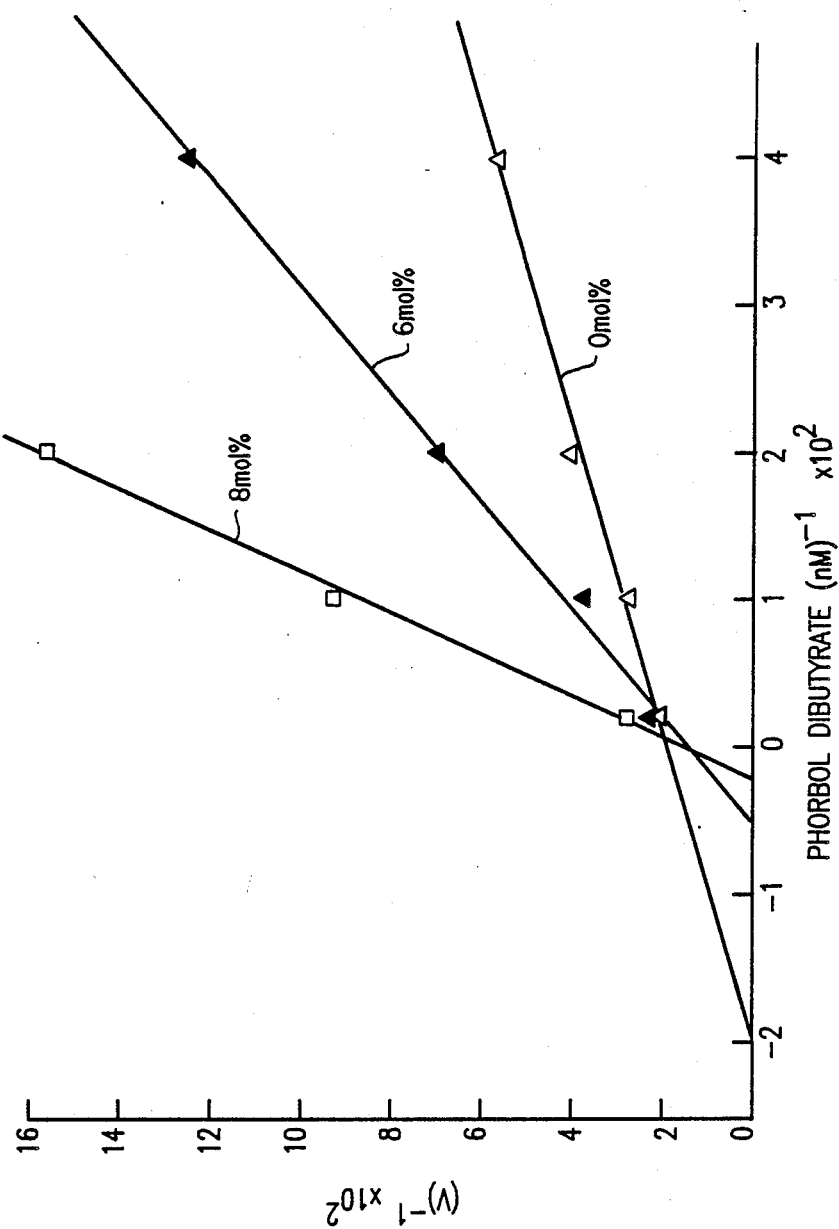
Figure 17:
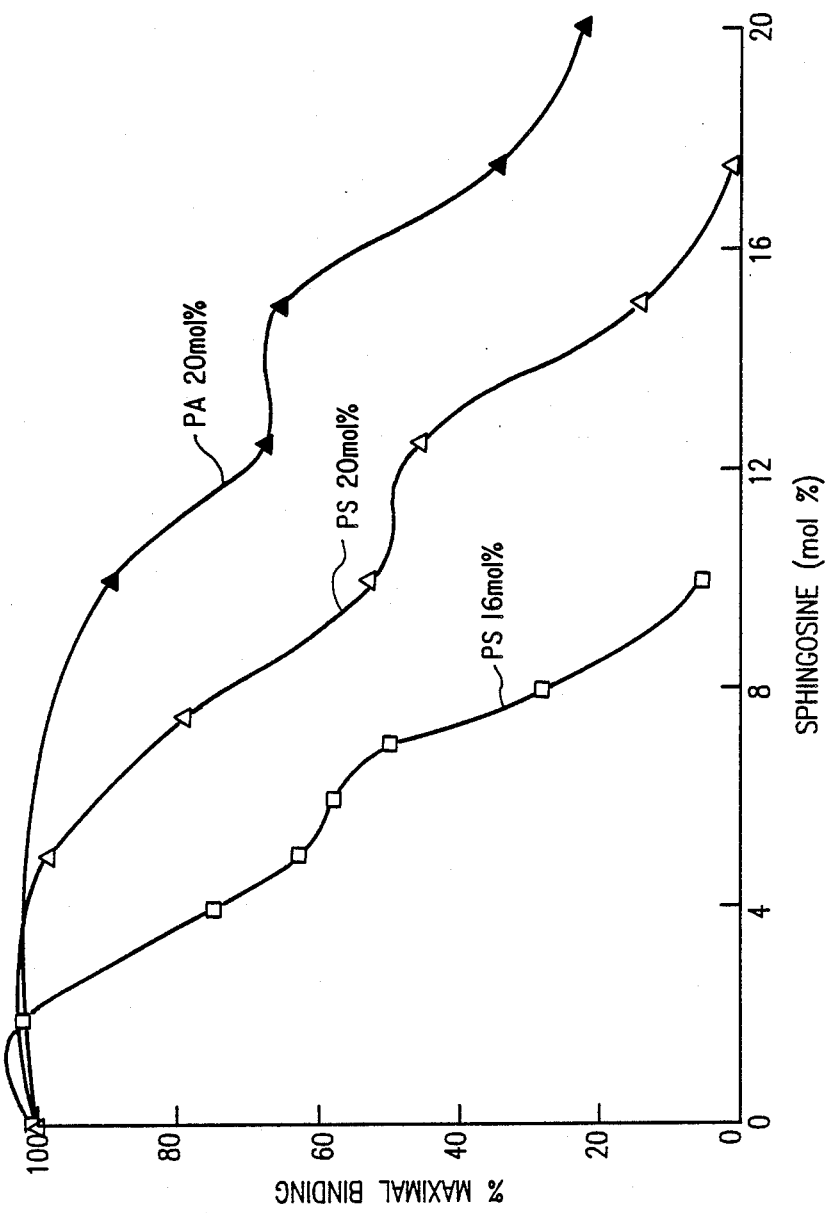
FIG. 17: Sphingosine Inhibition of Phorbol Dibutyrate Binding. Mixed micelles contained PS at 16 mol % (□) and 20 mol % (Δ); or PA at 20 mol % (▲) and 0-20 mol % of sphingosine. Binding studies were performed as described in the Experimental section. The data are plotted as % of maximal binding under each condition. With 16 mol % PS there was 82% of the [$^3$H]PDBu binding seen with 20 mol % PS. At 20 mol % PA there was only 51% of the binding seen with 20 mol % PS.

The effect of sphingosine on phorbol ester binding was examined to further substantiate the sphingosine inhibition occurs by interfering with the regulatory domain of protein kinase C. Sphingosine inhibited phorbol-ester binding to Triton X-100 mixed micelles containing 16 and 20 mol % PS (FIG. 17). The concentration dependence of sphingosine displacement of phorbol-dibutyrate, paralleled its ability to inhibit protein kinase C activation by PDBu (FIG. 13A). Sphingosine also inhibited phorbol binding when phosphatidic acid was used as the lipid cofactor (PA supports only 50% of the binding measured with PS).

Figure 18A:
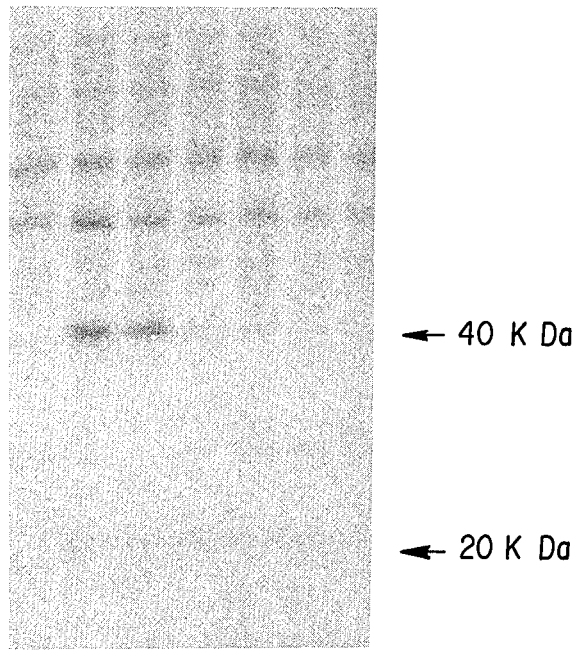
FIG. 18: Sohincosine Inhibition of Platelet Protein Phosphorylation. A. The effect of increasing sphingosine concentration on phosphorylation of the 40 kDa protein induced by thrombin. Lane 1: control platelets; Lane 2: thrombin (1 unit/ml); Lane 3: 10 μM sphingosine; Lane 4: 25 μM sphingosine; Lane 5: 50 μM; Lane 6: 100 μM; Lane 7: 200 μM. B. The 40k band was cut out and $^{32}$P was counted in Aquasol II. The % of maximal phosphorylation induced by thrombin is plotted as a function of sphingosine concentration.
Figure 18B:
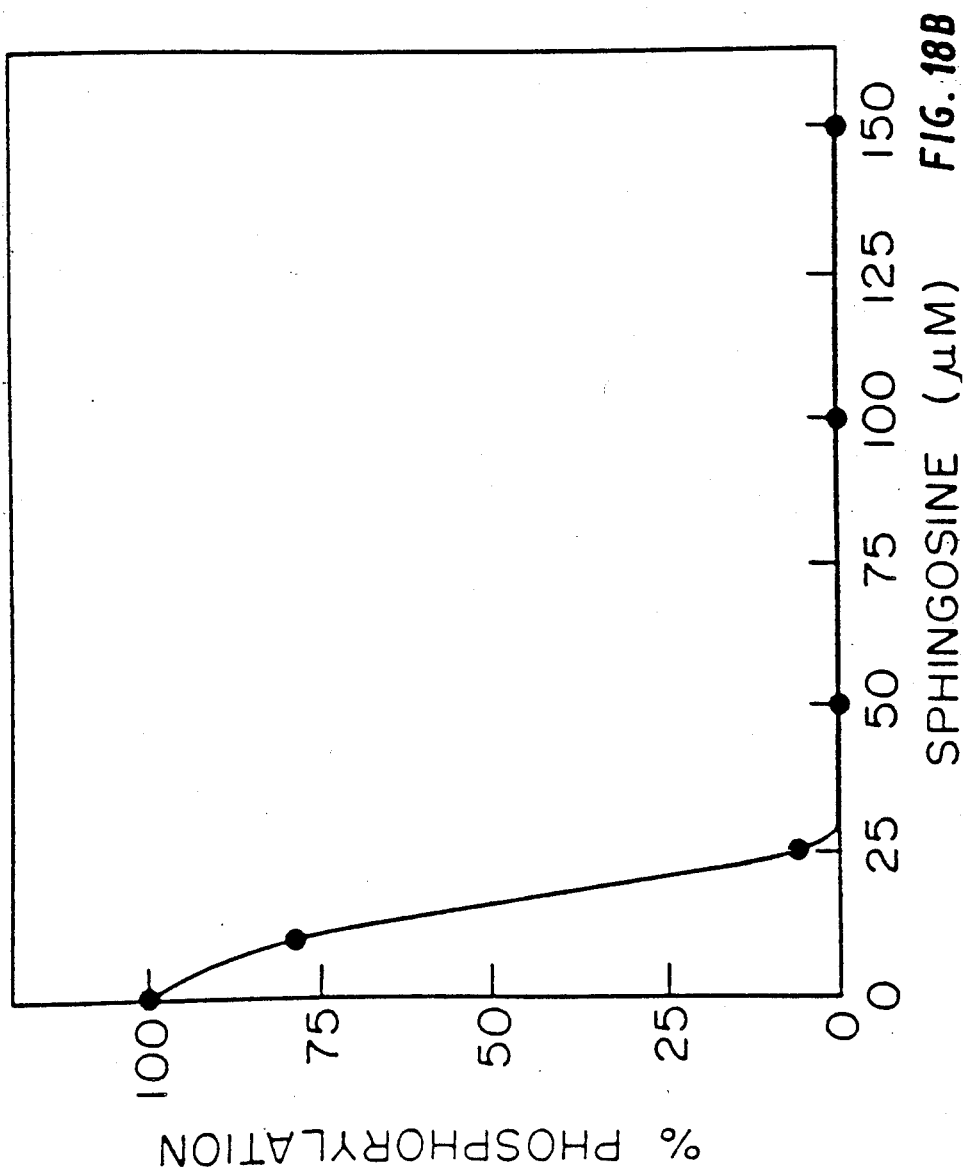

Next, experiments were conducted tested in human platelets to determine whether sphingosine would inhibit protein kinase C activation by thrombin. This was determined by monitoring the protein kinase C-induced phosphorylation of the 40 KDa polypeptide (FIG. 18A). As shown in FIG. 18B, sphingosine caused nearly complete inhibition of 40K phosphorylation at a concentration of 25 μM. Partial inhibition was seen with concentrations as low as 10 μM. Sphingosine also inhibited TPA and $diC_8$-induced 40K phosphorylation (data not shown).

Figure 19:
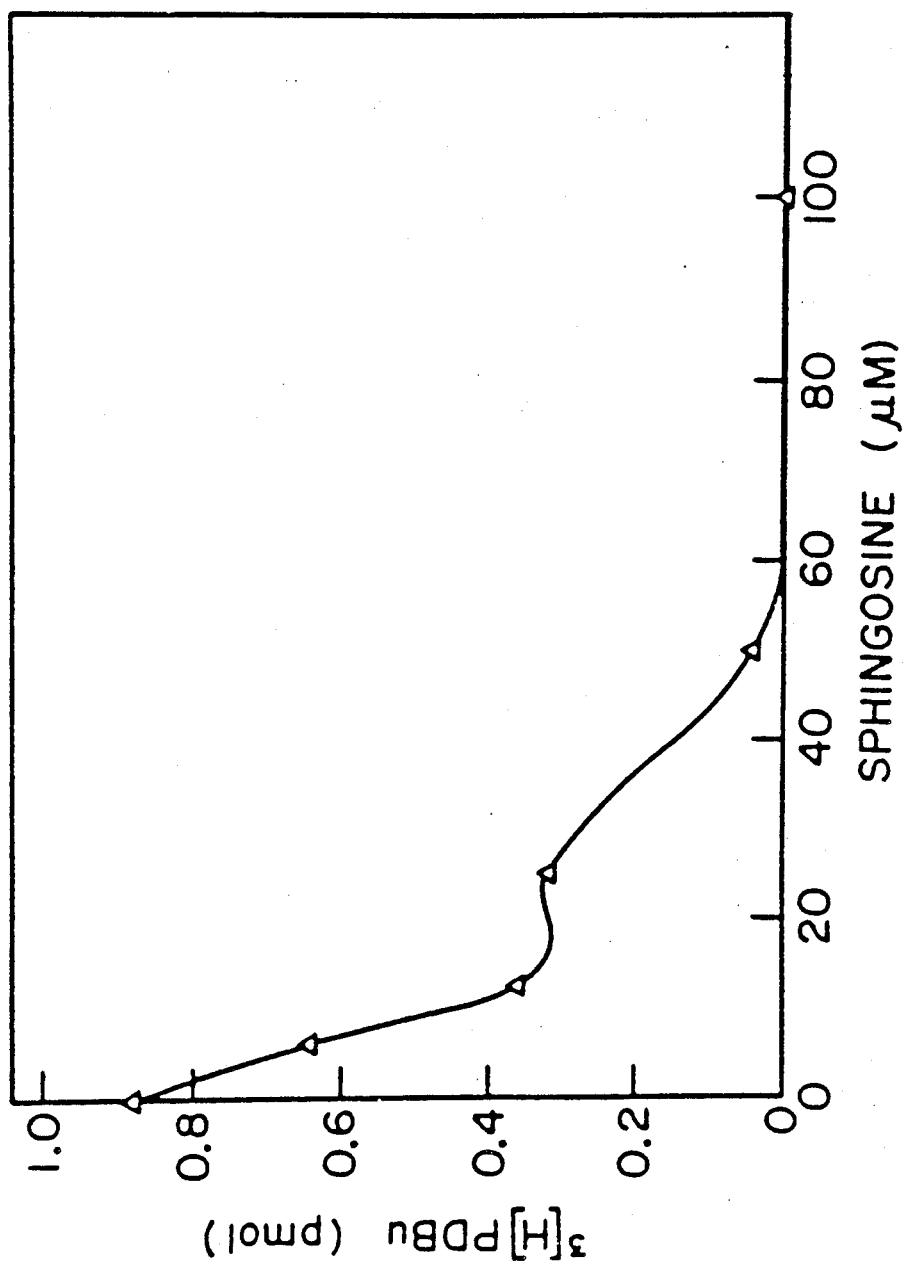
FIG. 19: Sohincosine Inhibition of PDBu Binding to Platelets. [$^3$H]PDBu was at 25 nM and platelets at $2.5 \times 10^8$ platelet/ml.

To further analyze the mechanism by which sphingosine inhibits protein kinase C activation, PDBu binding to whole human platelets was studied (FIG. 19). Saturable and displaceable binding of [$^3$H]PDBu to platelets was demonstrated (data not shown). Sphingosine was able to inhibit this binding in concentrations identical to those required to inhibit 30K phosphorylation.

Since sphingosine is an amphiphilic molecule and would be expected to partition into a bilayer or micelle, a direct comparison of its biologic effects to its in vitro potency in inhibiting protein kinase C requires that its bulk concentration be expressed as mol % sphingosine to phospholipids. To accomplish this, the amount of PS and total phospholipids in platelet membranes were quantitated. Human platelets were found to have 20% of their total phospholipids as PS and the absolute PS concentration under the assay conditions was 200 μM. Therefore, the sphingosine concentrations (expressed as mol % sphingosine:phospholipids) required to inhibit platelet 40K phosphorylation were similar to those required for in vitro inhibition of protein kinase C; 3–5 mol % sphingosine required for complete inhibition (or 15–25% of PS). In addition, this inhibition demonstrated the same reversibility observed in the in vitro system in that increasing the concentration of $diC_8$ or of platelets (i.e. PS) overcomes the inhibition.

Figure 20:
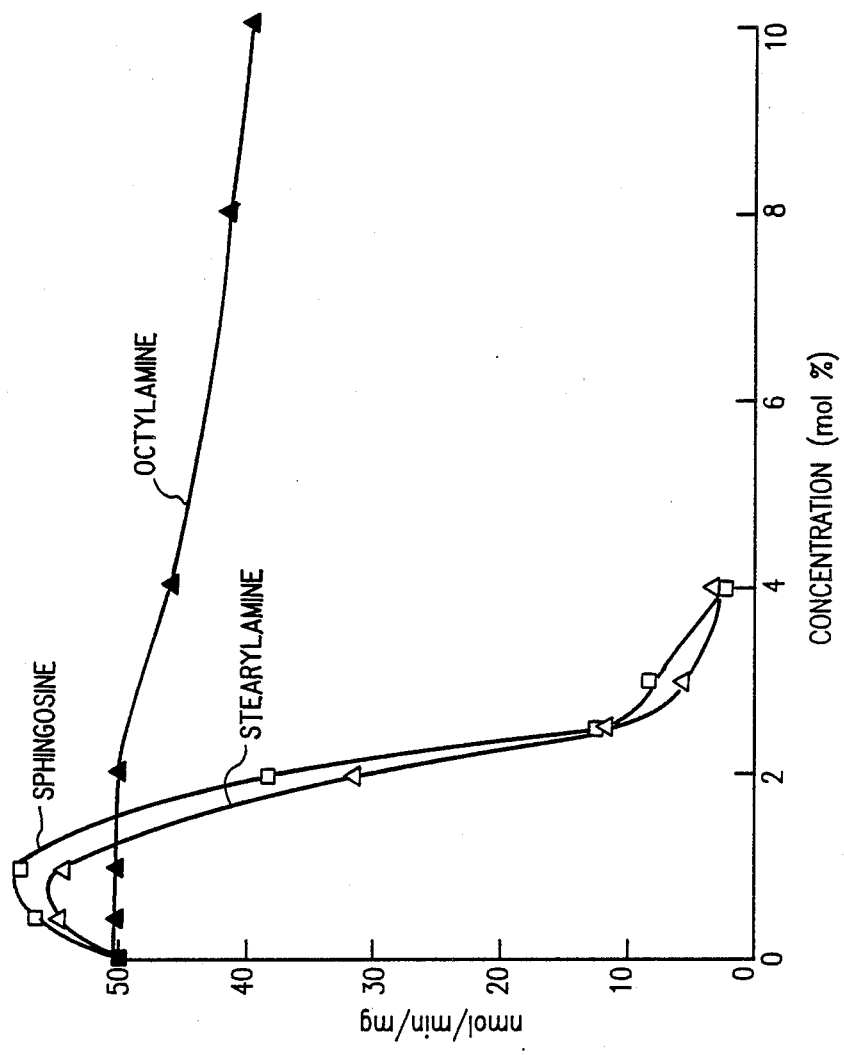
FIG. 20: Effects of Stearylamine and Octylamine on Protein Kinase C. Mixed micelles contained 5.5 mol % PS, 1.0 mol % diC$_{18:1}$, and sphingosine (□), octylamine (▲), or stearylamine (Δ).
Figure 21:
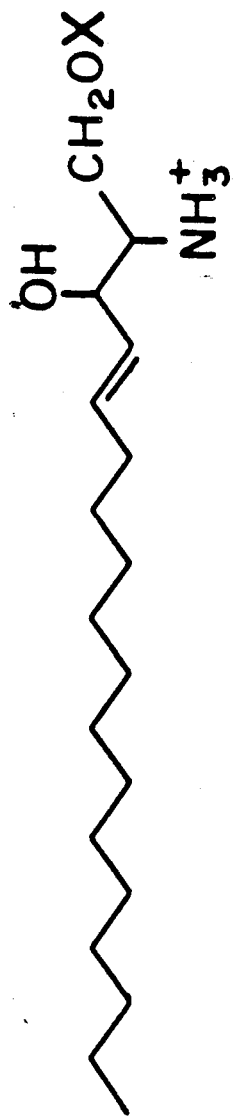
FIG. 21: Structure of Lysosohingolioids. Lysosphingolipids are derivatives of the long-chain base sphingosine where the 1-hydroxyl is substituted by different head groups. With the exception of lysosphingomyelin (sphingosylphosphorylcholine) where the linkage is through a phosphodiesteric bond, lysosphingolipids have a glycosidic bond at C-1.
Figure 22A:
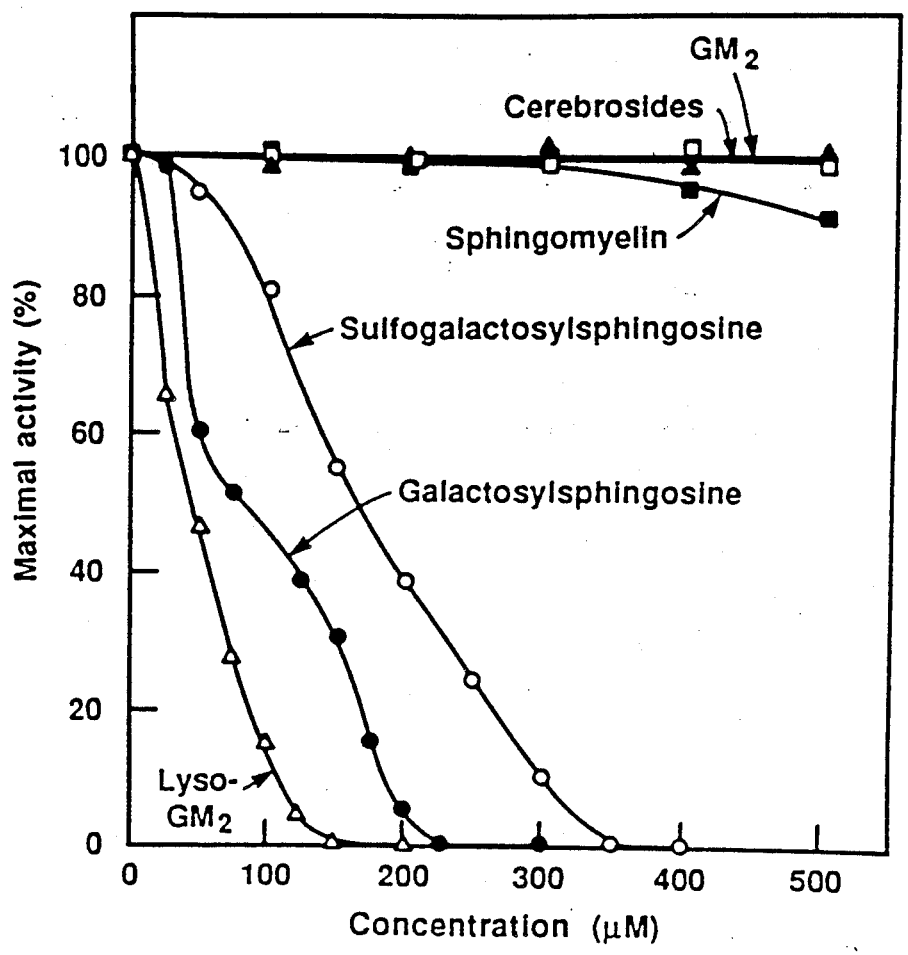
FIG. 22: Inhibition of Protein Kinase C by Lysosphingolipids. A. Psychosine (●), sulfogalactosylsphingosine (O), and lyso-GM$_2$ (Δ) were potent inhibitors of protein kinase C when activity was measured at 6 mol % ohosphatidylserine, 2 mol % sn-1,2-dioleoylglycerol, and 100 μM Ca$^{2+}$. These data are representative of the inhibition observed with the rest of the related lysosphingolipids. The parental sphingolipids were also evaluated for their effects on protein kinase C activity. They were dried down from chloroform/methanol solutions with the lipid cofactors of protein kinase C and solubilized in Triton X-100. None of the parent compounds inhibited protein kinase C, as shown for cerebrosides, sphingomyelin, and GM$_2$. To further investigate the specificity of inhibition of protein kinase C by lysosphingolipids, the N-acetyl derivatives of galactosylsphingosine, sphingosylphosphorylcholine, and lyso GM$_2$ were prepared as described by Gaver and Sweeley for the N-acetyl derivative of sphingosine. The compounds were purified on a CN HPLC column and then tested for their effects on protein kinase C activity. None of these N-acetyl derivatives inhibited protein kinase C. B. The lysosphingolipids displayed surface dilution kinetics (the data shown for galactosylsphingosine is representative of the group). Galactosylsphingosine was less potent when protein kinase C was assayed at higher concentrations of Triton X-100 mixed micelles containing fixed amounts of phosphatidylserine (6 mol %) and dioleoylglycerol (2 mol %). When the data are plotted as mol % psychosine:Triton X-100 (inset), the inhibition profiles at the different concentrations of Triton X-100 (0.15% w/v, □ 0.3%, ●, 0.6%, ■, and 1.8%, ▲) appeared identical. These results indicate that the lysosphingolipids preferentially partition into the mixed micelles; therefore, effective concentrations should be expressed as mol % of the liquid compounds of Triton X-100 and not as bulk concentrations.
Figure 22B:
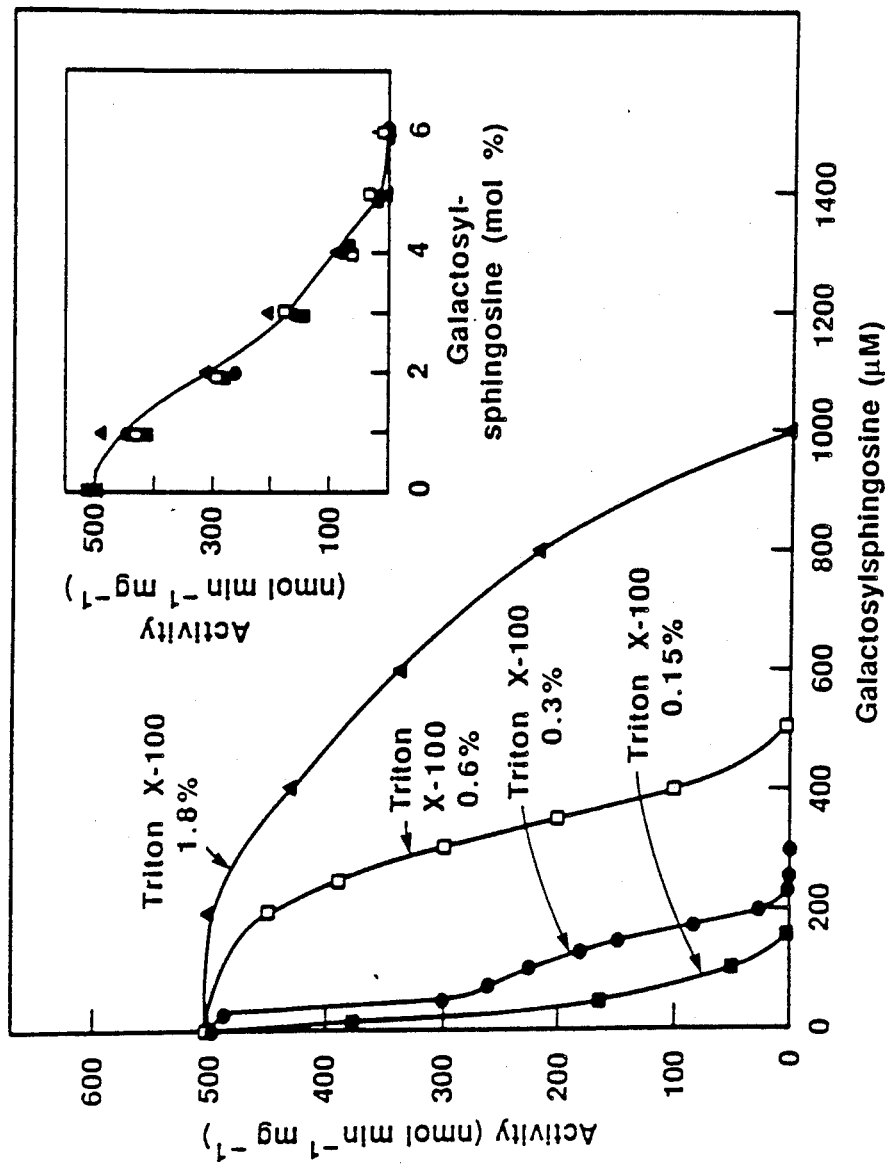
Figure 23:
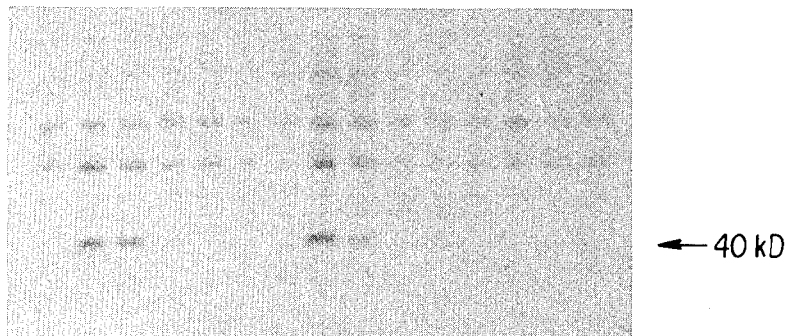
FIG. 23: Inhibition of 40 kDa phosphorylation in Platelets. The phosphorylation of 40 kDa polypeptide in human platelets in response to thrombin was carried out. Lysosphingolipids inhibited the ohosphorylation of this polypeptide which is known to be effected by protein kinase C. Lane 1; unstimulated platelets, lanes 2-15; thrombin 1 μ/ml, lanes 3-7; galactosylsphingosine 5, 10, 25, 50 and 100 μM, lanes 8-11; lysosulfatide 5, 25, 50, and 100 μM, lanes 12-15; lyso $GM_2$ 25, 50, 100, and 200 μM. Galactosylsphingosine (25 μM) did not affect the generation of diacylglycerol second messengers in response to thrombin. Also, the N-acetyl derivatives of galactosylsphingosine and sphingosylphosphorylcholine did not affect 40 kDa phosphorylation when tested at concentrations less than 100 μM, indicating that the inhibition by lysosphingolipids was specific and not due to non-specific detergent actions.

The specificity of protein kinase C inhibition by sphingosine was investigated using a number of related molecules. As seen in FIG. 20, octylamine did not inhibit at the concentrations tested whereas stearylamine was nearly as effective as sphingosine. Swainsonine, structurally related to sphingosine, was not an inhibitor. N-acetylsphingosine, ceramide and 1,3-dihydroxy-2-amino-3 phenylpropane derivative were without effect. Fatty acids, and cetyl triethylammonium bromide were also inactive. However, 3-ketosphinganine, erythro- and threo-sphinganine were all inhibitors. The results presented show that sphingosine is a potent and reversible inhibitor of protein kinase C. This suggests that sphingosine may be a useful inhibitor of protein kinase C in different cell systems. Results with platelets, in HL-60 cells and in neutrophils further attest to the usefulness of sphingosine as a protein kinase C inhibitor.

Sphingosine differs from the other known inhibitors of protein kinase C in that it is a natural component of cells comprising a critical component of ceramide, the building block of sphingomyelin and the glycosphingolipids. Sphingosine and other naturally occurring long-chain (sphingoid) bases are synthesized by serine palmitoyltransferase. Sphingosine could also be generated by the action of ceramidases (N-acyl sphingosine amidohydrolases). These metabolic pathways raise the possibility that the generation of sphingosine intracellularly may serve as a regulatory negative effector of protein kinase C activity. Sphingosine levels may be regulated in response to either intra- or extracellular signals. In fact, sphingomyelin was observed to undergo rapid deacylation and N-acylation when lymphocytes were stimulated to undergo blastogenesis. The deacylation of sphingomyelin leads to the generation of sphingosylphosphorylcholine (lysosphingomyelin). This molecule may lead to the generation of sphingosine through hydrolysis of the phosphorylcholine head group. Therefore, these catabolic pathways for the generation of sphingosine or one of its analogues may play a physiologic role in modulating the activity of protein kinase C. The activity of protein kinase C is expected to be a function of the concentration of PS (phospholipid), DAG, $Ca^{2+}$ and the negative effector, sphingosine[3].

FOOTNOTES

[1]The abbreviations used are: PS, phosphatidylserine; DAG, sn-1,2-diacylglycerol; $diC_{18:1}$, sn-1,2-dioleoylglycerol; $diC_8$, sn-1,2-dioctanoylglycerol; EGTA, ethylene glycol bis (β-aminoethyl)$N,N,N^1,N^1$-tetraacetic acid; PA, phosphatidic acid; PDBu, phorbol dibutyrate, TPA, phorbol 12-myristate, 13-acetate (PMA).

[2]The catalytic domain was generated by trypsin treatment of purified protein kinase C; and purified by Ultrogel AcA-44 molecular sieve chromatography. The fractions showing protein kinase activity independent of $Ca^{2+}$, PS, and DAG were pooled and used for the above experiments.

[3]This suggests an explanation for the different concentration dependencies of protein kinase C activation by the cell permeable diacylglycerol, $diC_8$, observed in different cell types. In platelets, neutrophils, and A431 cells, μM $diC_8$ was effective; whereas, in tracheal 2C5 cells, pituitary cells, and HL60 cells, 10–100 μM amounts were required. Perhaps the higher $diC_8$ concentrations required reflects the presence of an anti-signal (negative effector) in these cell types, such as sphingosine.

III. Lysophinogolipid Inhibition of Protein Kinase C

TABLE VI: Inhibition of protein kinase C activity and phorbol-dibutyrate binding by lysosphingolipids. The first column lists different disease entities that constitute the sphingolipidosis, and the second column shows the lysosphingolipids that are expected to accumulate in each of these diseases. Accumulation has been demonstrated in the case of galactosylsphingosine, glucosylsphingosine, and lyso $GM_2$. The remaining two columns show the observed effects of the lysosphingolipids of protein kinase C activity and phorbol diester binding in vitro and in human platelets. Lysogangliosides were prepared from their parental gangliosides by hydrolysis in methanolic KOH esentially as described by Neuenhofer et al. in *Bioch.* 24, 525, 1985. During this preparation, with approximately 90–95% conversion, the N-acetate of N-acetylneuraminic acid is partially hydrolyzed. Fatty acids were partitioned into heptane after acidification of the methanolic reaction mixture. Galactosylsphingosine, glucosylsphingosine, and lactosylsphingosine were prepared as previously described for galactosylsphingosine (Radin, *Lipids* 9, 358, 1974) Sphingosylphosphorylcholine was prepared by hydrolysis in HCl-butanol (Kaller, *Biochemische Zeitschrift* 334, 451, 1961). The purity of the lyso derivatives (greater than 90%) was checked by thin layer chromatography (TLC) on silica gel H plates developed in chloroform/methanol/2N $NH_4OH$ (65/35/9) and visualized by ninhydrin reaction for N-lyso compounds, by α-naphthol/sulfuric acid for both gangliosides and lysogangliosides, and by a phospholipid spray for sphingosylphosphorylcholine. Lysosphingolipids were quantitated by reaction of the amine group with trinitrobenzenesulfonate. Gangliosides and lysosphingolipids were also quantitated by reaction with anthrone. The lysosphingolipids were then studied for their effect on protein kinase C activity. Protein kinase C was purified to near homogeneity by the method of Wolf et al. (*J. Biol. Chem.* 260, 15718, 1985), and activity was measured using a mixed micellar assay (described herein). Lysosphingolipids were added directly in aqueous solution, and allowed to equilibrate with the Triton X-100 (0.3% w/v) mixed micelles containing 6 mol % phosphatidylserine and 2 mol % dioleoylglycerol. All the lysosphingolipids proved to be potent inhibitors of protein kinase C (1 mol % = 43 μM). The complex acidic lysogangliosides were more potent than the neutral glycosphingolipid derivatives, possibly due to partial hydrolysis of the N-acetate groups leading to the generation of more than one amine per molecule. Phorbol-dibutyrate binding was measured in a mixed micellar assay. Lysosphingolipids inhibited phorbol-dibutyrate binding to protein kinase C in the presence of Triton X-100 mixed micelles containing 20 mol % phosphatidylserine. Lysosphingolipids appeared less potent at inhibiting phorbol dibutyrate binding than protein kinase C activity. The difference is related to the higher concentration of phosphatidylserine used in the binding assay, as both activity and binding show a high cooperative dependence on phosphatidylserine, which modulates the inhibition by lysosphingolipids. Phorbol-dibutyrate binding to human platelets and 40 kDa phosphorylation in platelets were carried out as described above. Lysosphingolipids inhibited phorbol dibutyrate binding to human platelets at concentrations in the 10–50 μM range. Inhibition of 40 kDa phosphorylation occurred over the same concentration range.

TABLE VI

| Disease | Lysosphingolipid | Inhibition of Protein Kinase C* μM (mol %) | Inhibition of [³H]PDBu Binding to Protein Kinase μM (mol %) |
|---|---|---|---|
| — | sphingosine | 80$^a$ (1.9) | 400$^b$ (9.3) |
| Krabbe's | galactosylsphingosine | 85$^a$ (2) | 500$^b$ (11.6) |
| Gaucher's | glucosylsphingosine | 85$^a$ (2) | 400$^b$ (9.3) |
| Lactosylceramidoses | lactosylsphingosine | 130 (3) | NT** |
| Neimann-Pick | sphingosylphosphorylcholine | 120$^a$ (2.8) | 500$^b$ (11.6) |
| Metachromatic | sulfogalactosylsphingosine | 150$^a$ (3.5) | 450$^b$ (10.5) |
| Leukodystrophy | sulfolactosylsphingosine | NT | |
| Fabry's | globotriosylsphingosine | 180 (4.2) | NT |
| | galabiosylsphingosine | NT | NT |
| GM$_1$ gangliosidosis | lyso GM$_1$ | 45 (1) | 300 (7.0) |
| Tay-Sach's | lyso GM$_2$ | 50$^a$ (1.2) | 300$^b$ (7.0) |
| Sandhoff's | lyso GA$_2$ | 60 (1.4) | NT |
| GM$_3$ gangliosidosis | lyso GM$_3$ | 45 (1) | NT |
| Other gangliosidoses | lyso GD$_{1a}$ | 25$^a$ (0.6) | NT |
| | lysotrisialoganglioside | 20 (0.5) | NT |
| | lysogloboside | 180 (4.2) | NT |
| | sphingosyltrihexoside | 180 (4.2) | NT |

*Concentrations giving 50% inhibition, 1 mol % = 43 μM under the assay conditions with 0.3% Triton X-100.
**NT: not tested.
$^a$These compounds were also tested for inhibition of 40 kDa phosphorylation in human platelets. They all inhibited thrombin, dioctanoylglycerol, and phorbol myristate acetate induced phosphorylation over a concentration range of 10–50 μM.
$^b$These compounds were also tested for their effects on PDBu binding to human platelts. They all inhibited binding over a concentration range of 5–50 μM.

IV. Inhibition of the Oxidative Burst in Human Neutrophils by Sphingoid Long Basis and the Role of Protein Kinase C therein Materials HESPAN (6.0% hetastarch in 0.9% NaCl) was obtained from American Critical Care Division of American Hospital Supply Corporation (McGraw Park, Ill.). Lymphocyte Separation Medium (LSM) (6.2% Ficoll, 9.4% sodium diatrizoate) was obtained from Bionetics Laboratory Products (Kensington, Md.). Formylmethionylleucylphenylalanine (FMLP), Phorbol 12-myristate 13-acetate (PMA), cytochalasin B, A23187, fatty acid free-bovine serum albumin, (BSA), ceramides (from bovine brain cerebrosides), cytochrome c (horse heart, type III), NADH, NADPH, Trypan Blue, superoxide dismutase, latex particles, palmitic acid, psychosine, erythro-dihydrosphingosine (sphinganine), and sphingosine were obtained from Sigma (St. Louis, MO). Na$_2$H[$^{32}$P]O$_4$ was obtained from New England Nuclear (NEN) (Boston, Mass.) (1000 mCi/nmol) and ICN Radiochemicals (Irvine, Calif.) (285 Ci/mg P). [$^3$H]-Phorbol dibutyrate (8.3 Ci/mmol) was obtained from Amersham (Arlington Heights, Ill.). Electrophoresis reagents were obtained from Bio-Rad (Rockville Center, N.Y.); 1,2-dioctanoylglycerol was obtained from Avanti Polar Lipids (Birmingham, Ala.). Phenyl analogs of sphinganine were synthesized by Dr. Dennis Liotta (Emory University Department of Chemistry). N-acetyl sphinganine was synthesized by the method of Gaver and Sweely.

The [$^3$H]-sphinganine was prepared by the reduction of N-acetyl-3-ketosphinganine by NaB$^3$H$_4$ (Amersham) followed by hydrolysis, and purified by silica gel column chromatography (Unasil, Clarkson Chemical Co., Williamsport, Pa.). The product yielded a single spot coincident with sphinganine when examined by TLC with silica gel H plates developed in CHCl$_3$:methanol: 2N NH$_4$OH (40:10:1). The specific activity was adjusted to 17,000 cpm/nmol by quantitating sphinganine as the TNBS derivative.

Methods

Isolation of Human Neutrophils

Human neutrophils were obtained by continuous flow leukapheresis from normal adults. Residual erythrocytes were removed by hypotonic lysis with a resulting purity of >95% neutrophils. Alternatively peripheral blood was obtained by phlebotomy and neutrophils were isolated by HESPAN (6% Hetastarch, 0.9% NaCl) sedimentaion of erythrocytes, centrifugation through lymphocyte separation medium (9.4% sodium diatrizoate, 6.2% Ficoll), and hypotonic lysis of residual erythrocytes. Isolated cells were resuspended in phosphate buffered saline (PBS)-glucose, containing 0.6 mM CaCl$_2$, 2.6 mM KCl, 1.5 mM KH$_2$PO$_4$, 0.5 mM MgCl$_2$, 136 mM NaCl, 8 mM Na$_2$HPO$_4$, 5.5 mM glucose.

Preparation of Stock Solutions of Effectors

Effectors of the oxidative burst include activators, inhibitors, and modulators. Stock solutions of FMLP, PMA, Cytochalasin B, were prepared at 5 mg per ml in dimethylsulfoxide (DMSO). The calcium ionophore A23187 was prepared as a 1 mM stock in DMSO. Long-chain bases, fatty acids, and other inhibitor analogs were prepared as equimolar concentrations of the effector and fatty acid-free BSA.

Measurement of Oxygen Consumption

Oxygen consumption was measured using a Clark-type electrode with YSI model 53 oxygen monitor. Assays were conducted at 37° C. with 6.5×10$^6$ cells per ml with a total volume of either 2.5 ml or 4 ml. Effectors were injected into the electrode chamber using a Hamilton syringe. The conditions for each measurement are given in figure legends. Initial slopes after the addition of the stimuli were used for rate calculations. For activators with a lag prior to the onset of the oxidative burst, maximal rates following the lag were used.

Assay for Superoxide Production

Superoxide production by cells was quantitated from superoxide-mediated reduction of cytochrome c, monitored as an increase in absorbance at 550 nm and an extinction coefficient at 21,000 $M^{-1}$ $cm^{-1}$. Measurements were carried out at 37° C. using approximately $5 \times 10^5$ neutrophils per ml, stirred continuously. The cells were allowed to equilibrate several minutes prior to the addition of effectors. Conditions for individual experiments are described in figure legends and tables. Controls utilizing added superoxide dismutase verified that the cytochrome c reduction was mediated by superoxide.

Superoxide production was also measured spectrophotometrically in isolated membranes (see below) by the method of Curnutte et al (*N. Eng. J. Med.* 293, 628–632) also using superoxide dismutase inhibitable reduction of cytochrome c. Assays utilized paired cuvettes with the reference cuvette containing 30 μg/ml superoxide dismutase. Both cuvettes also contained 65 mM potassium phosphate pH 7.0, 125 mM sucrose, 81 μM cytochrome c, and 0.1 mg of membrane protein. The reaction was initiated with 200 μM (final) NADPH in both cuvettes. The treatments are as described in Table I. All spectrophotometric measurements were carried out using a Cary 219 UT-visible spectrophotometer.

Cell Viability

Cell viability was assessed by two criteria: Trypan Blue exclusion and release of the cytosolic enzyme, lactate dehydrogenase (LDH). LDH activity was monitored by following the oxidation of NADH at 340 nm. Activity was determined in three groups of cells: control (no additions), neutrophils plus 50 μM sphinganine, and cells permeabilized with 0.5% Triton X-100 (final concentration) for complete release of cellular LDH. Trypan Blue exclusion was determined microscopically.

Isolation of Activated Membranes

Neutrophil membranes activated for superoxide production were prepared as described previously (Hohn, *J. Clin. Invest.* 55, 707–713, 1975). Neutrophils ($10^8$) were suspended in PBS-glucose and incubated in a shaking waterbath at 37° C. Cells were activated by the addition of 10 μg PMA/ml and allowed to incubate 5 min. The reaction was stopped by adding an equal volume of ice-cold PBS. The cells were centrifuged at $400 \times g$ for 4 min at 4° C. and resuspended in PBS-glucose containing 120 μM FAD. The cells were lysed by homogenization with a teflon-glass homogenizer. The homgenate was centrifuged at $250 \times g$ for 10 min. to remove unlysed cells. The supernatant was centrifuged at $27,000 \times g$ for 30 min. to yield the membrane/granule-rich fraction. The pellet was resuspended in Tris-HCl, pH 8.6, containing 15% glycerol and 120 μM FAD.

Phagocytosis

Latex particles were opsonized by incubating at 37° C. 1 ml of particles with 0.2 ml of human serum plus 1 ml Tris buffer, pH 8.5. Neutrophils ($2 \times 10^6$ cells) in 0.1 ml of PBS-glucose (either containing 40 μM sphinganine or with no addition) were incubated with $10^8$ particles at 37° C. for 5 min. The reaction was terminated by the addition of 0.4 ml of ice-cold buffer containing 1 mM EDTA. The cells were then diluted by 80% with 0.15M NaCl and layered onto a ficoll/sodium metrizoate solution (density = 1.077) and centrifuged 20 minutes at $400 \times g$ at 4° C. Cells are sedimented, while excess beads remain at the ficoll-saline interface. The number of latex beads internalized per cell was determined by microscopic examination.

Sphinganine Inhibition of Cellular Phorbol Dibutyrate Binding

Neutrophils ($1 \times 10^8$ cells/ml) were preincubated with the indicated concentration of sphinganine, palmitic acid, or ceramide for five minutes prior to the addition of 50 nM (final concentration) of [$^3$H]-phorbol dibutyrate (specific activity of 8.3 Ci/mMole). The cells were incubated an additional 15 min. in a shaking waterbath at 37° C. The incubation mixtures were filtered using an Amicon filtration manifold model VFM-III and washed 5 times with 5 mls of ice-cold PBS-glucose. The filters were counted using a Beckman LS7000 scintillation counter.

Phosphorylation Studies

Neutrophils ($1.4 \times 10^8$ cells) were preincubated in with 0.5 mCi $Na_2H^{32}PO_4$ in buffer containing 136 nM NaCl, 5.56 mM glucose, 10 mM Hepes, and 0.33 mM $CaCl_2$ for a total of 1 hr at 37° C. in a shaking waterbath. Excess unbound counts were removed by centrifugation and resuspension, repeated five times. The cells were then divided into 4 treatment groups (see RESULTS below) containing approximately $3.5 \times 10^7$ cells each. All groups were incubated at 37° C. in a shaking waterbath for the same total time. Some samples were incubated 10 min. with sphinganine (40 μM) prior to addition of 1 μM PMA (final concentration), with which they were incubated for an additional 15 min. The reaction was stopped by addition of an equal volume of boiling SDS dissociation buffer (9% SDS, 1% mercaptoethanol, 15% glycerol, 30 mM Tris, pH 7.8). The samples were run on a 12% SDS-polyacrylamide gel using the method of Rudolph and Krueger (*Adv. Cyclic Nucleotide Res.* 101, 107–133, 1979). The gels were dried using a Bio-Rad model 2400 Gel Slab Dryer. Autoradiography was performed on the dried gels using Kodak X-omat X-ray film and Dupont Cronex intensifying screens. The gels were exposed for 12 hrs at −70° C.

Alternatively, neutrophils were preincubated as described above using 0.1 mCi of $^{32}$P labeled phosphate. The cells were broken by 5 min. of sonication using an Ultramet III waterbath sonicator, and 5% (final concentration) trichloroacetic acid was added to each sample. The precipitate was filtered and trichloroacetic acid was added to each sample. The precipitate was filtered and washed extensively using an Amicon filtration system and counted using a Beckman LS7000 scintillation counter.

Measurement of Cytoplasmic Calcium Concentration

Intracellular calcium was measured by the Quin2 method. Briefly, Quin2/acetoxymethylester (50 μM) was preincubated with $1 \times 10^8$ cell/ml for 20 min. at 37°, prior to 10-fold dilution and continuation of incubation for an additional 40–60 minutes. Cells were reisolated by centrifugation to remove extracellular fluorophore, and fluorescence measurement and calibration were carried out as described by Tsien et al in *J. Cell. Biol.* 94, 325–334, 1982, using a Perkin-Elmer MPF-44B fluorescence spectrophotometer. Buffer consisted of 140 mM NaCl, 5 mM KCl, 1 mM Na$_2$PO$_4$, 5.5 mM glucose, 0.5 mM MgSO$_4$, 20 mM Hepes, and 1 mM CaCl$_2$.

TABLE VII
EFFECT OF SPHINGANINE ON NADPH-OXIDASE ACTIVITY IN ISOLATED NEUTROPHIL MEMBRANES

| ADDITION | Cytochrome c Reduction (nmols/min/mg/protein) |
|---|---|
| NONE | 18 |
| BSA (50 µM) | 18 |
| SPHINGANINE (18 µM) | 27 |

Cytochrome c reduction was monitored as described in the Experimental section.

TABLE VIII
EFFECT OF SPHINGANINE ON OXYGEN CONSUMPTION USING VARIOUS ACTIVATORS

| | RATE† nmols O$_2$ consumed/min/10$^6$ cells | |
|---|---|---|
| ACTIVATOR | NO SPHINGANINE | SPHINGANINE |
| Phorbol Myristate Acetate (1 µM) | 4.3 | 0.2 |
| Dioctanoyl Glycerol (100 µM) | 6.1 | 0.3 |
| FMLP (0.5 µM) + Cytochalasin B (5 µg/ml) | 5.3 | 0.3 |
| Opsonized zymosan (30 µg/ml) | 5.3 | 0.3 |
| Arachidonate (83 µM) | 4.2 | 0.2 |

† Oxygen consumption was measured using a Clark oxygen electrode, as described in the Experimental Section. For incubations in the presence of sphinganine, 50 µM sphinganine (final) plus 50 µM fatty acid-free BSA were added to the cells 3 minutes prior to addition of the activator. In control experiments, 50 µM BSA alone prior to activation did not affect the activated rate.

TABLE IX
SPHINGANINE ANALOGS STRUCTURE/FUNCTION EFFECTS

| ANALOG | Concentration required for 50% inhibition µM |
|---|---|
| erythro-Sphinganine | 7 |
| threo-Sphinganine | 24 |
| Sphingosine | 9 |
| Stearylamine | 25 |
| Octylamine | 300 |
| 3-amino-3-hydroxy-3-phenyl-propanol | |
| R,R-S | n.i.* |
| R,R-R | n.i. |
| N-acetylsphinganine | n.i. |
| Ceramide | n.i. |
| Palmitic acid | n.i. |
| †CTAB | n.i. |

*n.i. = no inhibition at 100 µM analog
†cetyl trimethylammonium bromide

TABLE X
INHIBITION BY SPHINGANINE OF [$^{32}$P]-PHOSPHATE INCORPORATION INTO TCA-PRECIPITABLE MATERIAL

| ADDITION | COUNTS PER MINUTE † |
|---|---|
| NONE | 2932 |
| PMA (1 µM) | 4912 |
| PMA (1 µM) plus Sa (25 µM) | 2845 |
| Sa (25 µM) | 2506 |

† see Experimental section for methodology.

TABLE XI
EFFECTS OF SPHINGNINE ON INTRACELLULAR CALCIUM LEVELS AND ON FMLP-INDUCED CALCIUM TRANSIENTS IN HUMAN NEUTROPHILS

| | Calcium† | |
|---|---|---|
| Pretreatment | Resting µM | FMLP-Peak µM |
| None | 0.16 ± 0.02 (4) | 0.59 ± 0.13 (3) |
| Sphinganine (30 µM) | 0.20 ± 0.02 (3) | 0.66 ± 0.14 (3) |

† Intracellular calcium was measured using Quin2, as described in the Experimental Section. Each measurement utilized 7.5 × 10$^6$ cells in 2 mls buffer. The "FMLP-Peak" value refers to the maximum calcium concentration achieved following 1 µM FMLP addition, but prior to the gradual return of calcium towards resting levels. Numbers in parenthesis refer to the number of experiments averaged to obtain the reported values. Fluorescence was corrected in the sphinganin e experiments for a small amount of fluorescence of the albumin carrier.

RESULTS

Figure 24A:
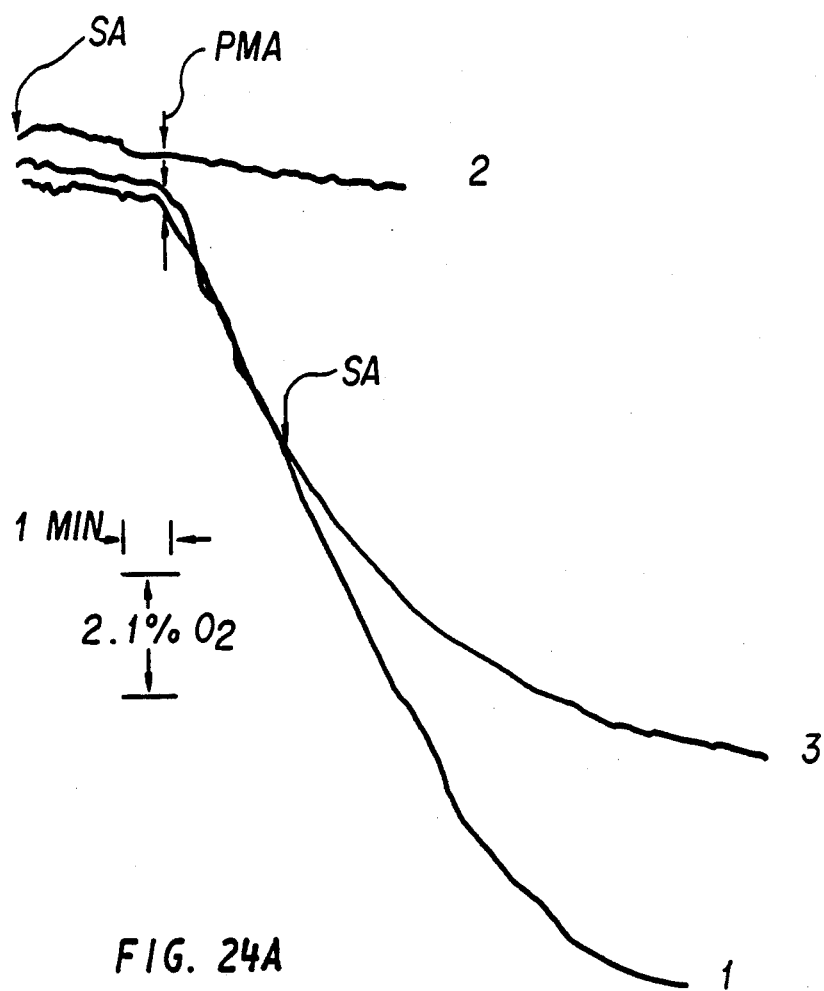
FIG. 24: Effect of Sphinganine on the Oxidative Burst. Panel A shows tracings of oxygraph recordings. Tracing 1 shows the effect of 1 μM PMA on oxygen consumption. In Tracing 2 cells were preincubated for 3 minutes with sphinganine (50 μM) prior to addition of PMA. Tracing 3 shows the addition of 40 μM sphinganine after activation with PMA. Panel B shows recordings of reduction of cytochrome c (monitored at 550 nm). Tracing 1 shows PMA (1 μM) induction of cytochrome c reduction. In control experiments the cytochrome reduction was shown to be completely inhibited by superoxide dismutase. Tracing 2 shows effects of preincubation of cells with 10 μM sphinganine prior to addition of PMA.
Figure 24B:
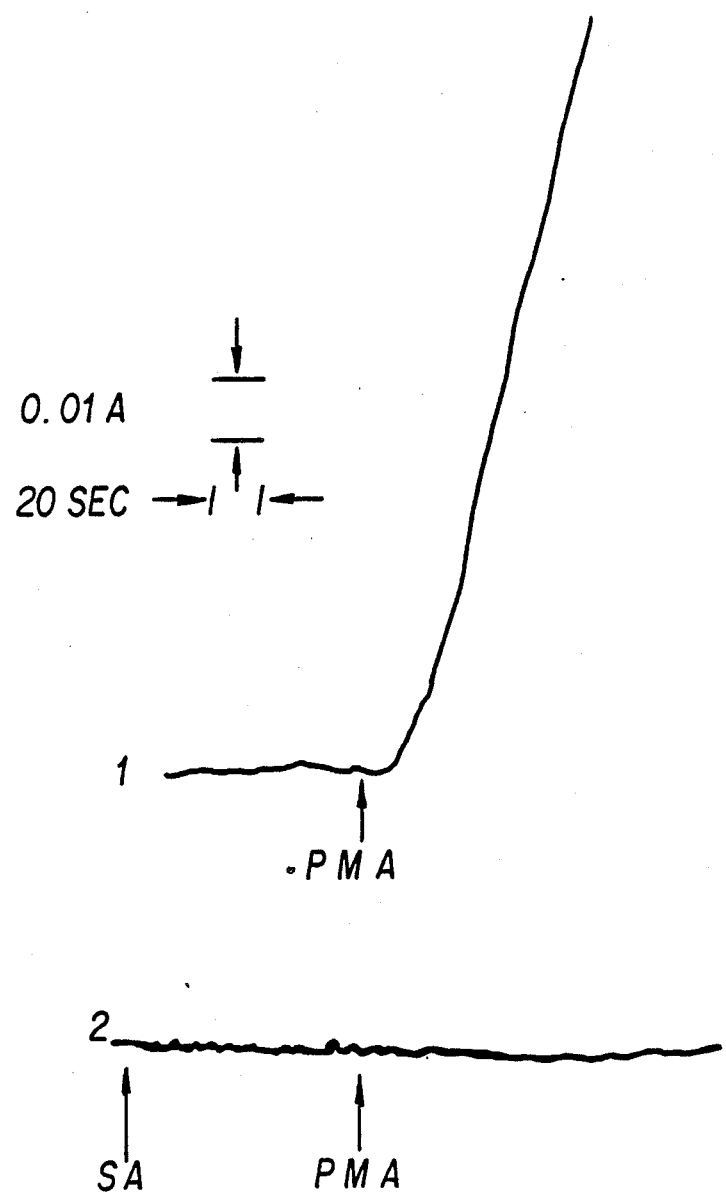

Inhibition by Sphinganine of O$_2$-consumption of Superoxide-Mediated Reduction of Cytochrome c Sphinganine was tested for its ability to inhibit the "oxidative burst" of normal human neutrophils. This lipid rather than sphingosine was used initially as the prototypical long-chain base, since it is commercially available in synthetic chemically well-characterized form. When neutrophils were preincubated with sphinganine, activation of O$_2$-consumption of PMA was abolished (See FIG. 24, Panel A). The increased oxygen consumption is though to reflect reduction of O$_2$ to superoxide anion, which can be detected by monitoring superoxide dismutase-inhibitable cytochrome c reduction. FIG. 24, panel B, shows the preincubation with sphinganine also blocks PMA activation of superoxide generation.

FIG. 24 (Panel A, Tracing 3) also illustrates that the addition of sphinganine several minutes after inhibition of the oxidative burst causes a gradual return to the basal rate of oxygen consumption. (The apparent loss of activity at later times in the control tracing (PMA stimulated, no sphinganine addition) was due to oxygen depletion, in contrast to the true inactivation seen following sphinganine addition.) The decay to basal rates followed first order kinetics as determined by plotting the natural log of the rate of oxygen consumption after addition of sphinganine as a function of time (not shown). The half-time for inactivation varied from 30 sec to 6 minutes with the individual donors examined. Since sphinganine added 2–3 minutes prior to activation with PMA completely abolished the oxidative burst for all donors, the inactivation rate does not appear to reflect the rate at which sphinganine gains access to the cell. Rather, we suggest that the variable rate of this decay represents individual variation in a normal inactivation process which is revealed when activation mechanisms are blocked.

Evidence that Sphinganine acts Reversibly and without Cytotoxicity on the NADPH-oxidase Activation Mechanisms The inhibitory effects of sphinganine were not due to cytotoxic efects of long-chain bases. When neutrophils (1.2 × 10$^7$ cells/ml) were incubated with 50 µM sphinganine, a completely inhibitory concentration, there was no effect on cell viability. Trypan Blue exclusion showed greater than 95% viability, and LDH release showed greater than 96% of cellular LDH was retained in both the presence and absence of sphinganine.

To determine whether the sphinganine inhibition was reversible, neutrophils ($1.2 \times 10^7$ cells/ml) were first incubated for 5-10 minutes with an inhibitory concentration (40 μM) of sphinganine. Rates of oxygen consumption in the freshly isolated cells were about 4 nmols/min/$10^6$ cells in the absence and 0.2 to 0.3 in the presence of sphinganine. Cells were then washed twice by centrifugation and resuspension in PBS-glucose containing 50 μM fatty acid-free BSA. After such procedures, restoration of PMA-induced oxygen consumption comparable to that in untreated cells was seen (3.7 and 3.8 nmols/min/$10^6$ cells respectively), indicating that inhibition of the oxidative burst by sphinganine is reversible.

To determine whether the observed effects of sphinganine were on the activation process or on the NADPH-dependent oxidase enzyme itself, membranes were prepared from PMA-pretreated cells, and examined for sphinganine effects on superoxide generation. Membranes isolated from PMA-pretreated cells have previously been shown to exhibit an approximately 10-fold increase in NADPH-dependent $O_2^-$-generation. No inhibition was observed when these membranes were incubated with concentrations of sphinganine which inhibited the cellular response (See Table VII). In fact, a slight stimulation was seen, as is also seen with some detergents. Thus, sphinganine does not inhibit the oxidase enzyme directly but must act at some site(s) involved in activation.

Lack of Effects of Sphinganine on Phagocytosis

Neutrophils were incubated with and without sphinganine in the presence of opsonized latex beads. These cells were reisolated, free of uningested beads (see Experimental section) and examined microscopically for the presence of ingested beads. In 208 control cells, there were an average of $7.4 \pm 1.0$ (S.E.M.) beads per cell, while in the presence of sphinganine, there were $7.2 \pm 0.8$ beads/cell (178 cells counted). Thus, there is no significant inhibition of phagocytosis by sphinganine. Therefore, not only is there no evident toxicity during the experimental time frame, but also this complex cellular function remains unaffected.

Effect of Sphinganine on the Oxidative Burst Induced by A Variety of Activators.

Figure 25A:
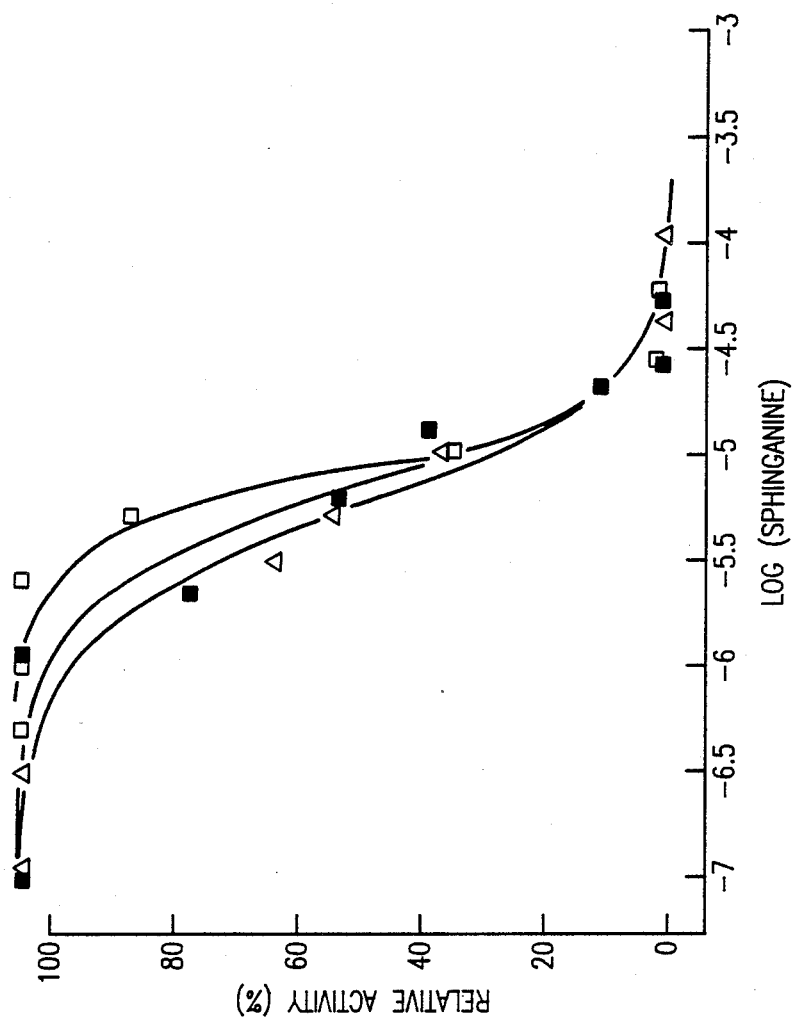
FIG. 25: Concentration Dependence for Inhibition of Oxidative Events by Sphinganine with Several Types of Activators. Panel A. Cells ($7.5 \times 10^6$ cells/ml) were preincubated with the indicated concentration of sphinganine for 3 min. prior to activation with 100 μM dioctanoyl glycerol (open squares), PMA (filled squares), or opsonized zymosan (open triangles). Oxygen consumption was measured as described in Experimental section using a Clark oxygen electrode. Panel B. Cells ($6.5 \times 10^5$ cells/ml) were incubated 3 minutes with the indicated concentrations of sphinganine prior to activation with PMA (open squares), FMLP (open triangles), or arachidonate (filled triangles). Superoxide production was monitored as in FIG. 24.
Figure 25B:
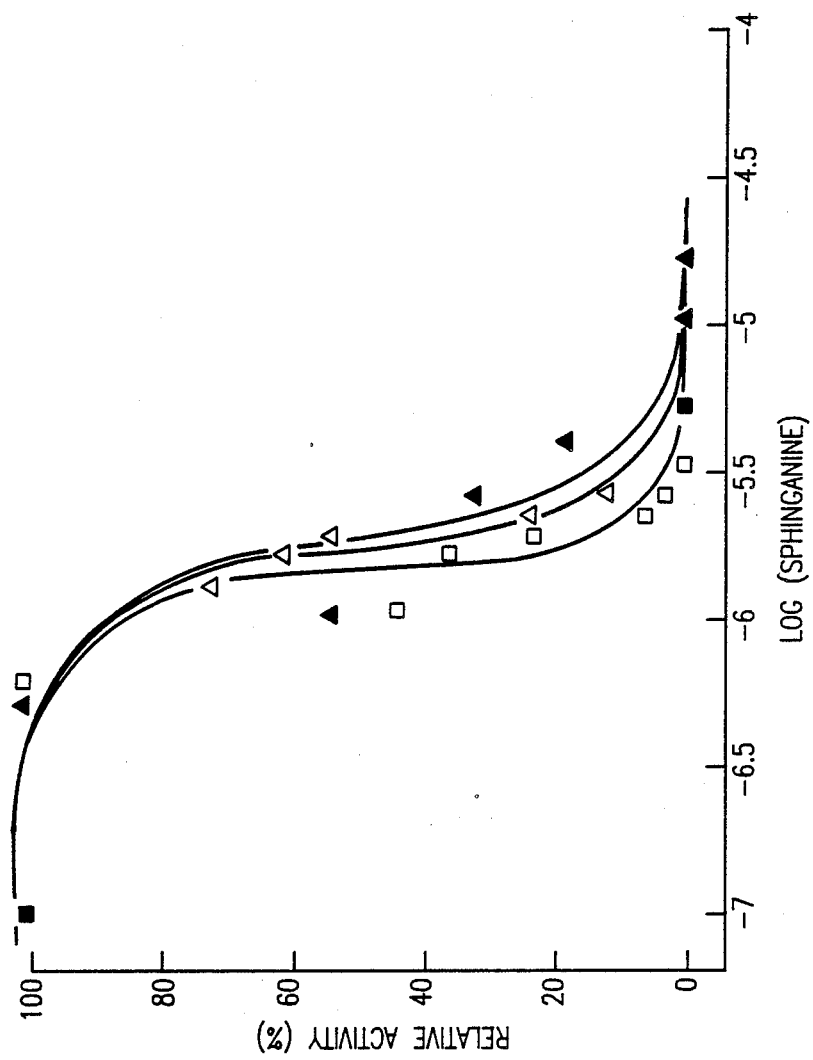

The inhibitory effect of sphinganine was tested using a variety of activators. Table VIII shows that with all activators-tested there was complete inhibition of the oxidative burst by sphinganine. To test whether all stimulants utilized a common, sphinganine-inhibitable step, the concentration dependence for inhibition was determined for a variety of activators. In initial studies with dioctanoylglycerol and PMA, oxygen consumption was monitored (FIG. 25, Panel A). Using this assay, half maximal inhibition occurred at 7.4 and 6.7 and 5.6 μM using diotanoylglycerol, PMA, and opsonized zymosan, respectively. These values are identical within experimental error and individual variation among donors. Thus, as has been suggested by a variety of earlier studies, phorbol esters and diacylglycerols appear to activate by a common mechanism. In addition, activation by opsonized zymosan appears to share this sphinganine-inhibitable mechanism.

To quantitate sphinganine inhibition using a series of other activators, the superoxide assay was used (FIG. 25, Panel B). This assay is considerably more sensitive and less time-consuming than the oxygen consumption assay, therefore requiring fewer cells and facilitating data aquisition. Activation by both FMLP and arachidonate was 50% inhibited at essentially the same concentration as that which effected PMA activation, again implicating a common site of inhibition. [Particulate activators could not be assessed using this assay due to turbidity and baseline noise.]

There is an apparent but readily explainable discrepancy in sphinganine concentration required for 50% inhibition using the two assays (compare, for example PMA activation in panel A versus Panel B of FIG. 25). This is due to the difference in cell number used in the two assays. The oxygen consumption assay requires large numbers of cells (approximately $7.5 \times 10^6$ cells/ml) and shows a concentration dependence for 50% inhibition of 6-8 μm sphinganine. In separate experiments (not shown) it was found that inhibition of oxygen consumption required a higher sphinganine concentration when the cell number was increased and lower when the cell number was decreased. The superoxide production measurements were obtained using about 10-fold less cells (approximately $5 \times 10^5$ cells/ml), and required about 1 μM sphinganine for 50% inhibition for all activators. Thus the difference in required concentration can be readily explained by a cell number effect. The concentration requirement appears to be approximately directly proportional to cell number as is also seen for many lipophilic compounds (e.g. diacylglycerols and arachidonate) whose activity requires partitioning into cellular membranes. This is in agreement with sphinganine inhibition being subject to surface dilution effects in an in vitro mixed micelle system and in platelets.

To determine how much inhibitor was actually becoming associated with the cells, radiolabeled sphinganine (3, 10, 30 μM) plus albumin carrier was incubated with neutrophils ($2.5 \times 10^6$ cells) for 5 min (i.e. a time longer than that needed to achieve inhibition). After washing by centrifugation, the cell-associated radioactivity was measured. Approximately 20% of the added sphinganine became cell-associated. Therefore, because of partitioning between the albumin and the cells, the cellular concentration of sphinganine was considerably less than the total. Thus, if generated intracellularly, long-chain bases are expected to be more effective than the concentration dependence for externally added inhibitor indicates.

Effect of Structural Analogs of Sphinganine on the Oxidative Burst

Figure 26:
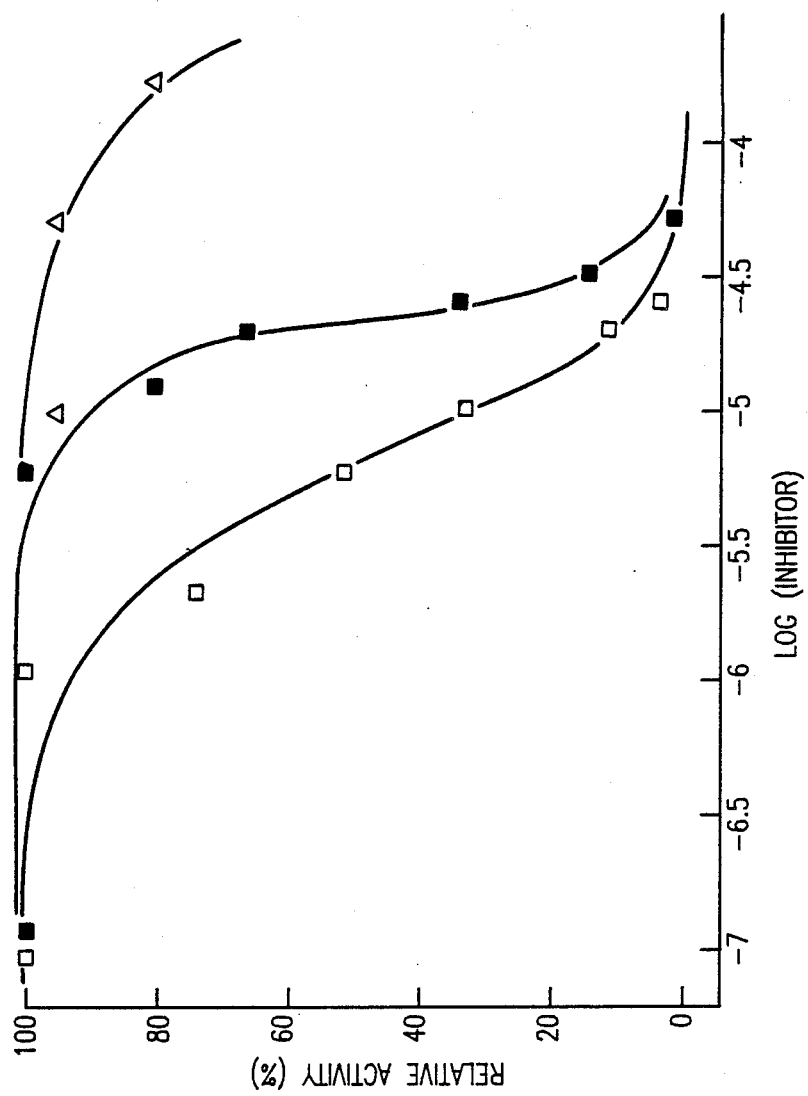
FIG. 26: Dose Dependence for Inhibition of Oxygen Consumption by Structural Analogs of Spinganine. Cells ($7.5 \times 10^6$ cells/ml) were incubated with sphinganine (open squares), stearylamine (filled squares), or octylamine (open triangles) at the indicated concentration, prior to activation with 1 μM phorbol myristate acetate. Oxygen consumption was measured using a Clark oxygen electrode.

Using PMA activation, analogs with structural features similar to those of sphinganine were tested for their effects on the oxidative burst (see FIG. 26 and Table IX). Compounds which also showed inhibitory effects include stearylamine, sphingosine, threo-sphinganine, and octylamine. Other compounds tested (See Table IX) did not show inhibition at 100 μM concentrations.

It appears that the structural features necessary for inhibition include a free amino group and a hydrophobic group such as a long alkyl chain. There is also a modest selectivity for the native stereoisomer, erythro-sphinganine, since the threo isomer was 3-4 times less effective. The longer alkyl chain derivatives were more effective than shorter, and a hydrophobic benzene ring could not substitute for an alkyl chain. Thus, sphinganine and sphingosine were the most effective inhibitors tested, and inhibition appears to exhibit some degree of structural specificity.

Sphinganine Inhibition of Radiolabelled Phorbol Dibutyrate Binding

Figure 27:
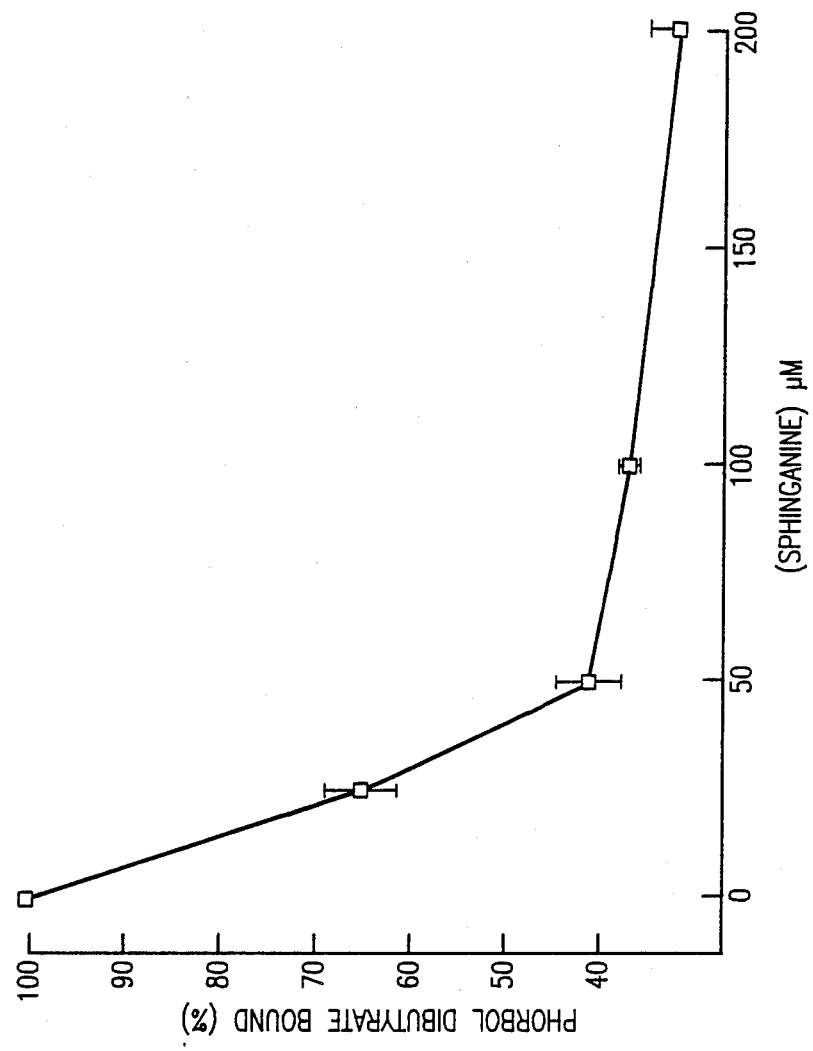
FIG. 27: Inhibition by Sphinganine of Cellular Phorbol Dibutyrate Binding. Cells ($1 \times 10^6$ cells/ml) were preincubated with the indicated concentrations of sphinganine for five minutes prior to addition of 50 nM (final concentration) of $^3$[H]-phorbol dibutyrate. The cells were then incubated for 15 minutes in a shaking water bath, 37° C. The incubation mixtures were filtered with ice cold PBS-glucose. The filters were then counted to quantitate bound phorbol dibutyrate. 100% represents 47,000 cpm.

Displacement of bound, radiolabeled phorbol dibutyrate by diacylglycerols has been used previously to provide evidence for a common cellular site of action (protein kinase C) for these two activators. Here, the inventors used the same technique to evaluate whether, as indicated by phosphorylation studies, sphinganine is acting by binding to protein kinase C. FIG. 27 shows that sphinganine displaces phorbol dibutyrate from its cellular binding site. Control studies were also carried out using 50 µM ceramide and palmitic acid, two analogs which did not show significant inhibition (see Table IX). With these analogs, there was 18% and 3% displacement, respectively compared with 60% displacement with the same concentration of sphinganine. Residual apparent binding is non-specific, since an excess of unlabeled PMA produced the same degree of displacement. These studies show that the decrease in binding of the phorbol ester does not appear to be due to detergent or other effects. Rather, there appears to be a specific inhibition of the phorbol ester binding by sphinganine. Such behavior was also seen in the micelle-reconstituted system and in human platelets.

In the present studies, the lipids sphinganine and sphingosine are shown to be potent inhibitors of the neutrophil oxidative burst. Sphinganine, a sphingoid long-chain base, is the product of the enzymatic condensation of palmitoyl-CoA and serine by serinepamitoyl transferase. Sphinganine can be incorporated into a variety of more complex biomolecules, the sphingolipids (eg. sphingomyelin, ceramide, and glycosphingolipids). Sphingosine is also an intermediate in sphingolipid biosynthesis, can be generated from the breakdown of sphingolipids, and is the predominant long-chain base in vivo. The present studies provide support for the proposal that one or more of the long-chain bases is an intracellular regulatory molecule. Although it remains to be shown whether these molecules are synthesized or mobilized in response to physiologic stimuli, free long-chain bases are present in HL-60 cells and in mature neutrophils (A. Merrill, personal communication) in quantities expected to affect the function of cellular protein kinase C. If, as has been proposed, neutrophil oxidative metabolism plays an important role in tumor generation, then long-chain bases might under some conditions function as "anti-tumor promoters".

The inhibition by long-chain bases of the oxidative burst appears to be a specific rather than a generalized metabolic effect. Incubation with sphinganine for the time required for the assays had no direct inhibitory effect on the NADPH-oxidase enzyme system. It may therefore be concluded that the inhibition of the oxidative burst involves the activation process rather than the oxidase itself.

That sphinganine does not have generalized effects on a variety of regulatory systems is indicated by at least three observations. First, in a system known to be cAMP-dependent, ACTH stimulation of steroidogenesis in the Y-1 tumor cell line, sphinganine did not affect the ACTH-stimulated steroidogenic rate (E. Wilson, unpublished studies). Second, sphinganine does not appear to affect $Ca^{++}$/calmodulin-dependent protein kinase, as evidenced by lack of inhibition of phosphorylation of the 20K protein in platelets using concentrations which completely abolished phosphorylation of the 40K protein known to be phosphorylated by protein kinase C. Third, long-chain bases do not significantly affect resting or FMLP-stimulated calcium levels. FMLP is thought to influence calcium levels initially via receptor-mediated activation of a phopholipase which cleaves phophatidylinositol-4,5-bisphosphate into diacylglycerol plus inositol triphosphate. The latter promotes release of intracellular calcium stores. Thus, it appears unlikely that long-chain bases exert their effects on the phopholipase or on calcium levels.

Two lines of evidence from the present studies implicate protein kinase C as a specific site of inhibition by long-chain bases. First, the inventors have shown that sphinganine can displace [$^3$H]-phorbol dibutyrate from the phorbol ester binding site. Phorbol esters have been shown to bind to and activate protein kinase C. According to data shown elsewhere in this section, sphinganine and phorbol esters compete for binding to protein kinase C. Secondly, PMA-stimulated phosphorylation is inhibited by sphinganine. Thus, long-chain bases appear specifically to block activation of protein kinase C. It is possible that sphinganine may have additional as yet unknown modulatory effects on other enzymatic systems. Nevertheless, the combination of data presented herein strongly implicates protein kinase C as the affected site.

The mechanism(s) of activation of the oxidative burst by what appears to be a diverse array of stimuli is (are) poorly understood. Sphinganine has been used in the present studies as a general probe of these mechanism(s) in human neutrophils. More specifically, the inventors wished to determine whether protein kinase C participates in some or all of the activation processes. Probably the best understood of the chemical activators are the phorbol esters such as PMA, which are potent activators of the enzyme. Also, synthetic diacylglycerols have been shown to be direct activators of protein kinase C. These compounds appear to activate by binding to protein kinase C. In the above experiments, it has been shown that activation of the oxidative burst by these compounds is inhibited by identical concentrations of sphinganine.

More complex in its mechanism, the chemotactic peptide FMLP functions by first binding to a plasma membrane surface receptor, thus promoting the hydrolysis of phosphatidylinositol-4,5 bisphosphate in a pertussus toxin-inhibitable process. Furthermore, stimulation with FMLP causes an increase in the concentrations of both calcium and diacylglycerol. Thus, a direct pathway for protein kinase C involvement in the oxidative burst can be postulated for FMLP activation via the generated diacylglycerol, but an elevation in cytosolic calcium has also been proposed to mediate the effects. In the present studies, sphinganine inhibited the oxidative burst without affecting the cytoplasmic FMLP-dependent rise in calcium concentrations. Thus a direct mediator role for calcium in activation of the oxidative burst seems unlikely. In measurements of $O_2^-$ production, the inventors have shown that the half maximal concentration of sphinganine required to inhibit superoxide production was virtually the same when either FMLP or PMA was used as the activator, implicating a common inhibition site (i.e. protein kinase C).

Likewise, activation of the oxidative burst by opsonized particles (e.g., zymosan) is inhibited by sphinganine in the same concentration range which inhibited PMA activation. The inventors conjecture that concurrent with phagocytosis, a protein kinase C activator (e.g. diacylglycerol or arachidonate) is generated, resulting in the observed oxidative burst. Thus, while phagocytosis itself is not inhibited by sphinganine, the concurrent activation of the oxidative burst is blocked, consistent with the involvement of protein kinase C in this pathway. The sphinganine-inhibited cells may therefore provide a model for some forms of chronic granulomatous disease, a condition in which the patient's neutrophils phagocytose microorganisms normally, but fail to mount an oxidative burst, thus resulting in difficulty in fighting infection.

In the present studies calcium has not been implicated as a direct activator of the oxidative burst. Data relating to this ion are contradictory, with two calcium ionophores giving different results. Iononmycin apparently does not activate while A23187 does. This apparent discrepancy may be explained by the finding that A23187 appears to activate the hydrolysis of phosphatidylinositols, and may therefore also function by diacylglycerol/protein kinase C dependent mechanisms. In preliminary studies, the inventors find that activation by A23187 is also blocked by sphinganine, thus supporting this interpretation.

In summary, sphinganine has been shown to be a potent inhibitor of the activation of the neutrophil "oxidative burst". It has further been shown through phosphorylation and competitive binding studies that the site of inhibition by sphinganine appears to be protein kinase C. From the studies utilizing various activators, the inventors propose that the activation mechanisms for not only diacylglycerol and phorbol esters, but also FMLP, arachidonate and opsonized zymosan converge to act through protein kinase C. The latter may act directly on the NADPH oxidase, or may phosphorylate another regulatory component, such as the cytosolic factor recently reported by Curnutte (*Blood* 66, 77a, 1985).

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for inhibiting protein kinase C, which comprises contacting a cell containing protein kinase C, with an acylated protein kinase C inhibitor having the formula:

$$Q-X-Y-\underset{NR_1R_2}{CH}-CH_2-O-Z$$

wherein Q is $CH_3-(CH_2)_n-$ or $CH_3-(CH_2)_m-CH=CH-(CH_2)_p-$ wherein n is 2-30; m is 1-15 and p is 1-15;
wherein X is $-CH_2-CH_2-$ or $-CH=CH-$, or such substituted by one or more halogens or $C_1-C_3$ alkyl groups;
wherein Y is

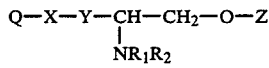

wherein W is a halogen;
wherein $R_1$ and $R_2$ are the same or different and are selected from hydrogen, lower alkyl groups having from 1 to 7 carbon atoms, aralkyl, and aryl groups wherein one of $R_1$ or $R_2$ is an in vivo enzyme-cleavable $C_1-C_8$ acyl group or an amino acid, and
wherein Z is selected from the group consisting of phosphate, H, galactosyl, sulfogalctosyl, glucosyl, lactosyl, trihexosyl, phosphorylchloine, GalNAc-Gal-Glc, Gal-Gal-Glc, Sia-Gal-Glc,

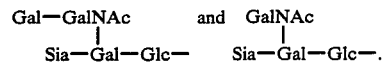

2. A method for inhibiting protein kinase C, which comprises contacting a cell containing protein kinase C, with a lysophingomyelin or a lysosphingaglycolipid having the ability of increasing the intracellular concentration of a protein kinase C inhibitory compound which produces inhibition of protein kinase C activity in vivo.

3. A unit dosage composition for inhibiting protein linase C upon routine administration in vivo, which comprises a protein kinase C inhibitory concentration of a compound having the formula:

$$Q-X-Y-\underset{NR_1R_2}{CH}-CH_2-O-Z$$

wherein Q is $CH_3-(CH_2)_n-$ or $CH_3(CH_2)_m-CH=CH-(CH_2)_p-$ wherein n is 2-30; m is 1-15 and p is 1-15;
wherein X is $-CH_2-CH_2-$ or $-CH=CH-$, or such substituted by one or more halogens or $C_1-C_3$ alkyl groups;
wherein Y is

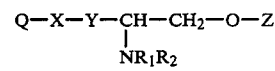

wherein W is a halogen;
wherein $R_1$ and $R_2$ are the same or different and are selected from hydrogen, lower alkyl groups having from 1 to 7 carbon atoms, aralkyl, and aryl groups, and
wherein Z is selected from the group consisting of phosphate, H, galactosyl, sulfogalctosyl, glucosyl, lactosyl, trihexosyl, phosphorycholine, GalNAc-Gal-Glc, Gal-GaI-Gla, Sia-Gal-Glc,

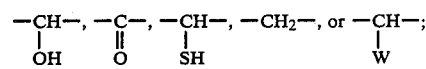

and a physiologically acceptable carrier.

4. The composition of claim 3, wherein said compound is sphingosine.

5. The composition of claim 3, wherein said compound us sphinganine.

6. The composition of claim 3, wherein said compound is psychosine.

7. The composition of claim 3, wherein Y is

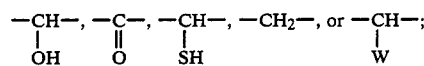

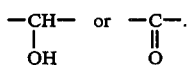

8. The composition of claim 3, wherein said physiologically acceptable carrier is a sterile liquid or cream.

9. A composition for inhibiting protein kinase C upon routine administration in vivo, which comprises a protein kinase C inhibitory concentration of a compound having the formula:

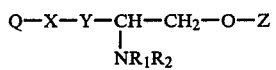

wherein Q is $CH_3-(CH_2)_n-$ or $CH_3-(CH_2)_m-CH=CH-(CH_2)_p-$ wherein n is 2-30; m is 1-15 and p is 1-15;

wherein X is $-CH_2-CH_2-$ or $-CH=CH-$, or such substituted by one or more halogens or $C_1-C_3$ alkyl groups;

wherein Y is

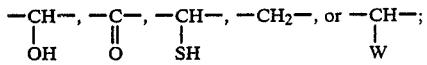

wherein w is a halogen;

wherein $R_1$ and $R_2$ are the same or different and are selected from hydrogen, lower alkyl groups having from 1 to 7 carbon atoms, aralkyl, and aryl groups, and wherein Z is selected from the group consisting of phosphate, H, galactosyl, sulfogalactosyl, glucosyl, actosyl, trihexosyl, phosphorylcholine, GalNAc-Gal-Glc, al-Gal-Glc, Sia-GalGlc, $$\begin{matrix} Gal-GalNAc \\ | \\ Sia-Gal-Glc- \end{matrix} \quad \text{and} \quad \begin{matrix} GalNAc \\ | \\ Sia-Gal-Glc- \end{matrix}.$$

with the proviso that $R_1$ and $R_2$ are not both hydrogen, and a physiologically acceptable carrier.

10. The composition of claim 9, wherein Y is

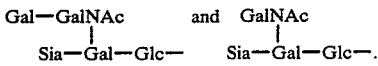

11. The composition of claim 9, wherein said physiologically acceptable carrier is a sterile liquid or cream.